(12) United States Patent
Grimm et al.

(10) Patent No.: US 7,960,409 B2
(45) Date of Patent: Jun. 14, 2011

(54) PHARMACEUTICAL PHENYLQUINOLINE AND CHROMEN-2-ONE TRIAZOLE COMPOUNDS

(75) Inventors: Erich L. Grimm, Baie d'Urfe (CA); Yves Ducharme, Montreal (CA); Richard Frenette, Laval (CA); Richard Friesen, Kirkland (CA); Marc Gagnon, Montreal (CA); Helene Juteau, Montreal (CA); Sebastien Laliberte, Ile-Perrot (CA); Bruce MacKay, Dollard-des-Ormeaux (CA); Yves Gareau, Notre-Dame de I'ile-Perrot (CA)

(73) Assignee: Merck Sharp & Dohme Corp., Rahway, NJ (US)

( * ) Notice: Subject to any disclaimer, the term of this patent is extended or adjusted under 35 U.S.C. 154(b) by 712 days.

(21) Appl. No.: 12/012,246

(22) Filed: Feb. 1, 2008

(65) Prior Publication Data

US 2008/0188521 A1    Aug. 7, 2008

Related U.S. Application Data

(60) Provisional application No. 60/899,471, filed on Feb. 5, 2007, provisional application No. 60/900,353, filed on Feb. 8, 2007.

(51) Int. Cl.
*A61K 31/47*     (2006.01)
*A61K 31/4192*   (2006.01)
*C07D 487/04*    (2006.01)
*C07D 401/06*    (2006.01)

(52) U.S. Cl. .......... 514/314; 546/167; 548/256; 514/359
(58) Field of Classification Search ............... 546/167; 548/256; 514/314, 359
See application file for complete search history.

(56) References Cited

U.S. PATENT DOCUMENTS

| 5,552,437 | A  | 9/1996 | Delorme et al. |
| 2006/0116406 | A1 | 6/2006 | Gareau et al. |
| 2007/0149579 | A1 | 6/2007 | Blouin et al. |

FOREIGN PATENT DOCUMENTS

| CA | 2125824 | | 12/1994 |
| CA | 2167317 | A1 | 2/1995 |
| WO | WO2007/016784 | A1 | 2/2007 |

*Primary Examiner* — Rebecca L Anderson
*Assistant Examiner* — Samantha L Shterengarts
(74) *Attorney, Agent, or Firm* — Mollie M. Yang; Valerie J. Camara

(57) ABSTRACT

The instant invention provides compounds of Formula I which are leukotriene biosynthesis inhibitors.

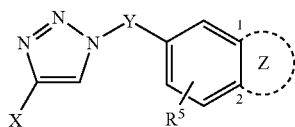

Compounds of Formula I are useful as anti-atherosclerotic, anti-asthmatic, anti-allergic, anti-inflammatory and cytoprotective agents.

20 Claims, 4 Drawing Sheets

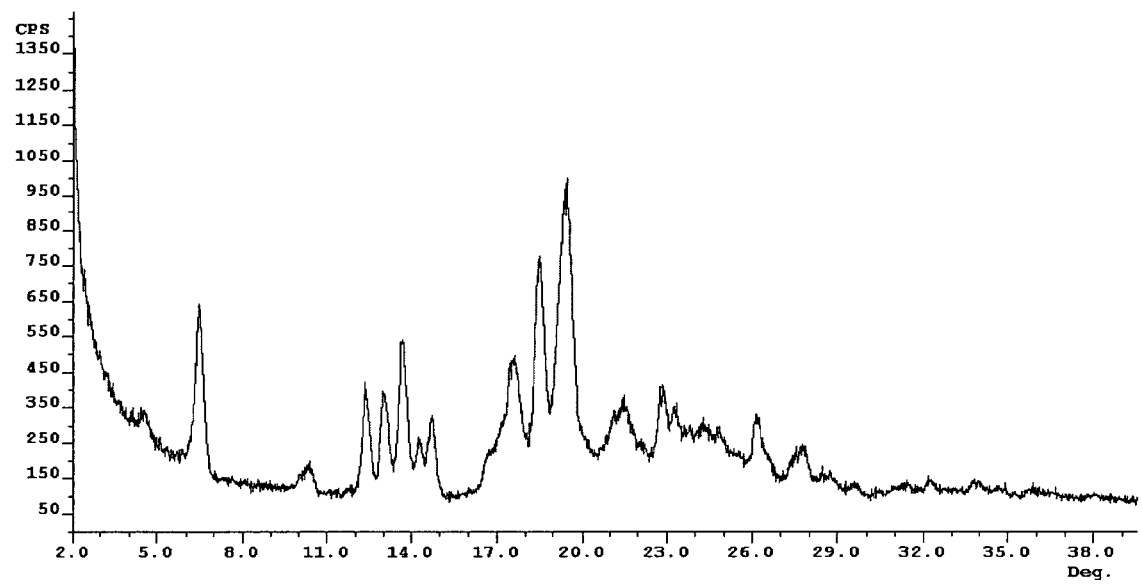
FIG. 1 Diffractograms of Compound of Example 1, Form A

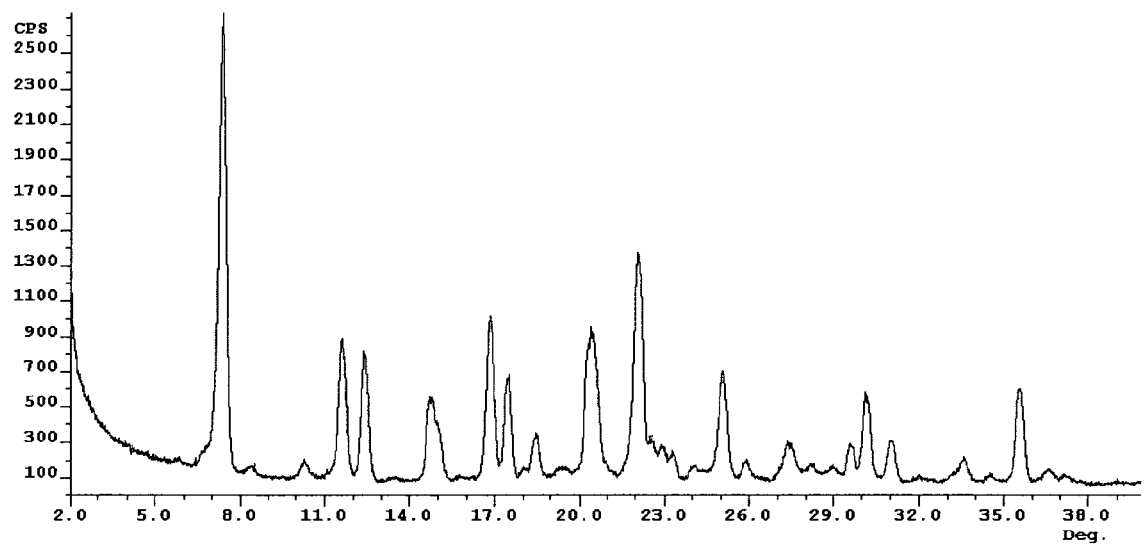
FIG. 2 Diffractograms of Compound of Example 1, Form B

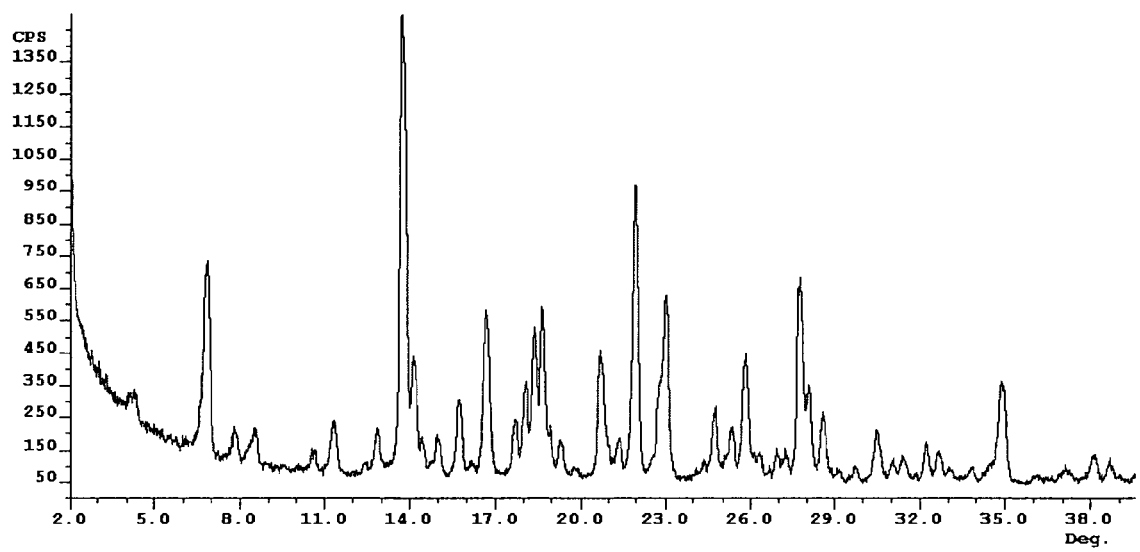
FIG. 3 Diffractograms of Compound of Example 1, Form C

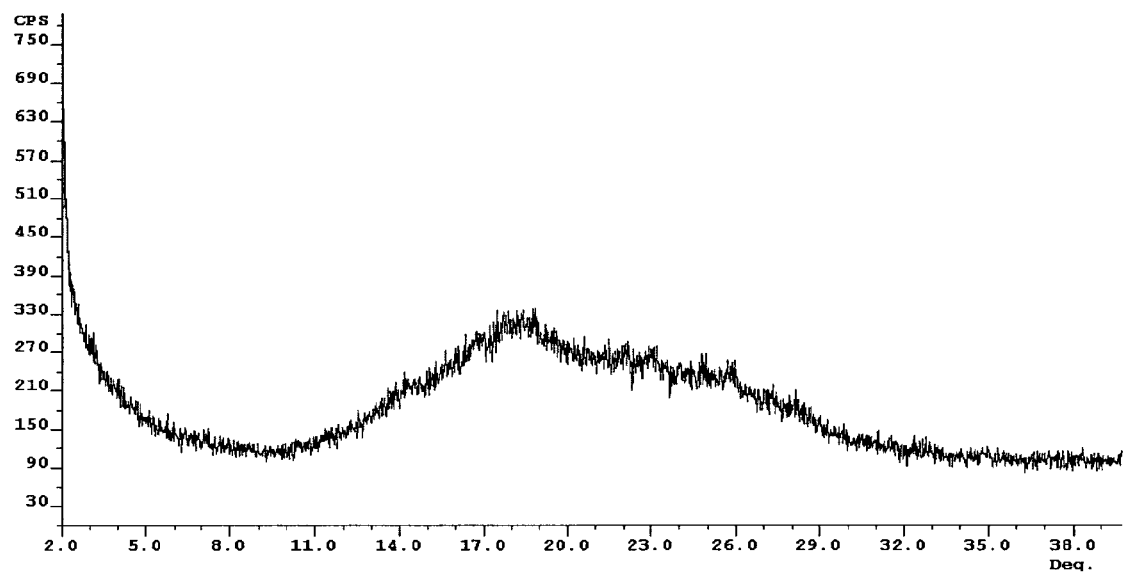
FIG. 4 Diffractograms of Compound of Example 1, Amorphous form

PHARMACEUTICAL PHENYLQUINOLINE AND CHROMEN-2-ONE TRIAZOLE COMPOUNDS

CROSS REFERENCE TO RELATED APPLICATIONS

This application claims priority from U.S. Provisional Application Ser. No. 60/900,353, filed Feb. 8, 2007, and U.S. Provisional Application Ser. No. 60/899,471, filed Feb. 5, 2007.

FIELD OF THE INVENTION

The instant invention involves novel compounds which are useful as inhibitors of leukotriene biosynthesis.

BACKGROUND OF THE INVENTION

Inhibition of leukotriene biosynthesis has been an active area of pharmaceutical research for many years. The leukotrienes constitute a group of locally acting hormones, produced in living systems from arachidonic acid. Leukotrienes are potent contractile and inflammatory mediators derived by enzymatic oxygenation of arachidonic acid by 5-lipoxygenase. One class of leukotriene biosynthesis inhibitors are those known to act through inhibition of 5-lipoxygenase (5-LO).

The major leukotrienes are Leukotriene $B_4$ (abbreviated as $LTB_4$), $LTC_4$, $LTD_4$ and $LTE_4$. The biosynthesis of these leukotrienes begins with the action of the enzyme 5-lipoxygenases on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book Leukotrienes and Lipoxygenases, ed. J. Rokach, Elsevier, Amsterdam (1989). The actions of the leukotrienes in living systems and their contribution to various diseases states are also discussed in the book by Rokach.

In general, 5-LO inhibitors have been sought for the treatment of allergic rhinitis, asthma and inflammatory conditions including arthritis. One example of a 5-LO inhibitor is the marketed drug zileuton (ZYFLO®) which is indicated for the treatment of asthma. More recently, it has been reported that 5-LO may be an important contributor to the atherogenic process; see Mehrabian, M. et al., Circulation Research, 2002 Jul. 26, 91(2):120-126.

Despite significant therapeutic advances in the treatment and prevention of conditions affected by 5-LO inhibition, further treatment options are needed. The instant invention addresses that need by providing novel 5-LO inhibitors which are useful for inhibiting leukotriene biosynthesis.

SUMMARY OF THE INVENTION

The instant invention relates to compounds of Formula I which are leukotriene biosynthesis inhibitors, methods for their preparation, and methods and pharmaceutical formulations for using these compounds in mammals, especially humans.

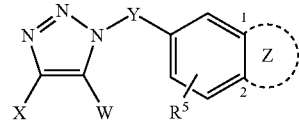

The compounds of Formula I are useful as pharmaceutical agents to slow or halt atherogenesis. Therefore, the instant invention provides a method for treating atherosclerosis, which includes halting or slowing the progression of atherosclerotic disease once it has become clinically evident, comprising administering a therapeutically effective amount of a compound of Formula I to a patient in need of such treatment. The instant invention also provides methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

Additionally, the instant invention involves the use of compounds of Formula I as anti-asthmatic, anti-allergic, anti-inflammatory and cytoprotective agents. They are also useful in treating angina, cerebral spasm, glomerular nephritis, hepatitis, endotoxemia, uveitis, and allograft rejection. The instant invention provides methods of treatment comprising administering a therapeutically effective amount of a compound of Formula I to a patient in need of the above-described treatments.

The instant invention further provides the use of a compound of Formula I in combination with other therapeutically effective agents. Additional embodiments will be evident from the following detailed description.

BRIEF DESCRIPTION OF THE DRAWINGS

FIG. 1 shows the XRPD of Form A of the compound of Example 1.

FIG. 2 shows the XRPD of Form B of the compound of Example 1.

FIG. 3 shows the XRPD of Form C of the compound of Example 1.

FIG. 4 shows the XRPD of amorphous form of the compound of Example 1.

DETAILED DESCRIPTION OF THE INVENTION

The novel leukotriene biosynthesis inhibitors of the instant invention are compounds of structural Formula I

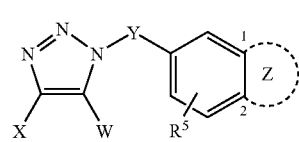

and the pharmaceutically acceptable salts thereof wherein:

is selected from the group consisting of

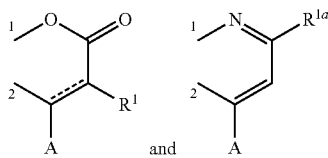

wherein the numbers "1" and "2" indicate the points of attachment within structural Formula I;
----- is selected from a single and a double bond;
A is selected from the group consisting of:
(a) a 5-membered heteroaryl ring containing (i) one or more carbon atoms, (ii) one heteroatom selected from oxygen and sulfur, and (iii) zero, one, two or three nitrogen atoms,
(b) a 5-membered heteroaryl ring containing one or more carbon atoms and from one to four nitrogen atoms,
(c) a 6-membered heteroaryl ring containing carbon atoms and one, two or three nitrogen atoms,
(d) a bicyclic ring system selected from benzothienyl, indolyl, quinolinyl and naphthalenyl,
(e) morpholinyl,
(f) phenyl,
(g) benzyl,
(h) chloro, and
(i) —C(O)C$_{1-3}$alkyl,
and wherein A is optionally mono- or di-substituted with a substituent independently selected at each occurrence from the group consisting of (i) fluorine, (ii) chlorine, (iii) —C$_{1-3}$ alkyl optionally substituted with one to five fluorines, (iv) —C$_{1-3}$ alkoxy optionally substituted with one to five fluorines, (v) C$_{3-6}$ cycloalkyloxy, (vi) —C$_{1-3}$alkyl-OH, (vii) —COOR$^8$, (viii) —CN, (ix) —NR$^7$R$^8$, and (x) —SO$_2$C$_{1-3}$alkyl;
W is H or methyl;
X is selected from the group consisting of pyridinyl, —Ph, and —C(R$^2$)(R$^3$)(R$^4$);
Y is selected from —CH$_2$— and —CH$_2$CH$_2$—;
R$^1$ is selected from the group consisting of —H, —C$_{1-6}$alkyl and —C$_{3-6}$cycloalkyl;
R$^{1a}$ is selected from the group consisting of: (a) —H, (b) —Cl, (c) —CN, (d) —COOR$^8$, (e) —CONR$^7$R$^8$, (f) —C(S)NR$^7$R$^8$, (g) —S(O)$_p$—C$_{1-3}$alkyl, (h) —NR$^7$R$^9$, (i) —C(=N—OH)—CH$_3$, (j) —C(=N—OCH$_3$)—CH$_3$, (k) —C(=NH)—OCH$_3$, (l) —C$_{1-6}$alkyl optionally mono- or di-substituted with a substituent independently selected at each occurrence from the group consisting of —OH and —F, (m) —C$_{1-3}$alkyl-O—C$_{1-3}$alkyl, (n) —C$_{1-3}$alkoxy optionally substituted with one to five fluorines, (o) —C$_{1-3}$alkoxy, (P) —C$_{3-6}$cycloalkyl, (q) phenyl optionally mono- or di-substituted with a substituent independently selected at each occurrence from the group consisting of —OH and —F, (r) pyridinyl optionally substituted with —C$_{1-3}$alkyl, particularly methyl, (s) 1-pyrrolidinyl, (t) 4-morpholinyl, and (u) 1-piperazinyl optionally 4N-substituted with —C$_{1-3}$alkyl particularly methyl;
p is an integer selected from zero, 1 and 2;
R$^2$ is selected from the group consisting of —H, —OH, —F, —C$_{1-3}$alkyl, —OC$_{1-3}$alkyl, —OC(O)—C$_{1-3}$alkyl, and —OC(O)-phenyl wherein phenyl is optionally substituted with a group selected from —OH and —NO$_2$; and —O-cyclic alkyl ether wherein the cyclic alkyl ether is comprised of one oxygen and 2-5 carbon atoms;

R$^3$ is selected from the group consisting of —H, —C$_{1-6}$alkyl, —C$_{1-6}$alkyl substituted with one or more of fluoro including for example but not limited to —C$_{1-6}$perfluoroalkyl including for example —CF$_3$ and —CF$_2$CF$_3$, —C$_{1-6}$alkyl substituted with R$^6$, phenyl, —C$_{2-6}$alkenyl, —C$_{3-6}$cycloalkyl, and —C$_{5-7}$cycloalkenyl;
R$^4$ is selected from the group consisting of —H, —C$_{1-6}$alkyl, —C$_{1-6}$alkyl substituted with one or more of fluoro including for example but not limited to —C$_{1-6}$perfluoroalkyl such as —CF$_3$ and —CF$_2$CF$_3$, —C$_{1-6}$alkyl substituted with R$^6$, phenyl, —C$_{2-6}$alkenyl, —C$_{3-6}$cycloalkyl, and —C$_{5-7}$cycloalkenyl;
or R$^3$ and R$^4$ are joined together with the carbon to which they are attached to form a ring selected from —C$_{3-6}$cycloalkyl, and a 3-6 membered cyclic alkyl ether comprised of one oxygen and 2-5 carbon atoms; C$_{5-7}$ cycloalkenyl, provided that there is no double bond at the C-1 position in the ring;
or R$^2$, R$^3$ and R$^4$ are joined together with the carbon to which they are attached to form 1-cyclopentenyl or 1-cyclohexenyl;
R$^5$ is independently selected at each occurrence from the group consisting of —H, —C$_{1-6}$ alkyl and —C$_{3-6}$cycloalkyl;
R$^6$ is independently selected at each occurrence from the group consisting of —COOR$^8$, —C(O)H, —CN, —CR$^5$R$^5$OH, —OR$^5$, —S—C$_{1-6}$alkyl and —S—C$_{3-6}$cycloalkyl;
R$^7$ is selected from the group consisting of —H, —C$_{1-6}$ alkyl, —C$_{3-6}$ cycloalkyl and —COOR$^8$;
R$^8$ is selected from the group consisting of —H, —C$_{1-6}$ alkyl and —C$_{3-6}$ cycloalkyl; and
R$^9$ is independently selected from the group consisting of —H, —C$_{1-6}$ alkyl, and —C$_{3-6}$ cycloalkyl, phenyl and benzyl.

In one embodiment of this invention are compounds within the scope of Formula I having structural Formula Ia wherein the variables are as defined in Formula I:

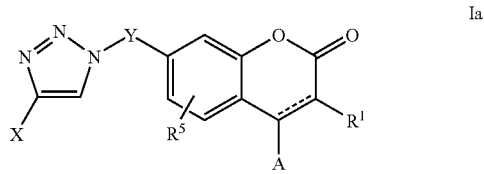

and the pharmaceutically acceptable salts thereof.

In another embodiment of this invention are compounds within the scope of Formula Ia having structural Formula Ib wherein the variables are as defined in Formula I:

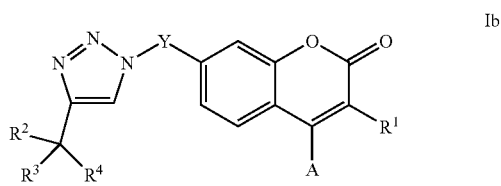

and the pharmaceutically acceptable salts thereof.

In another embodiment of this invention are compounds within the scope of Formula I having structural Formula Ic wherein the variables are as defined in Formula I:

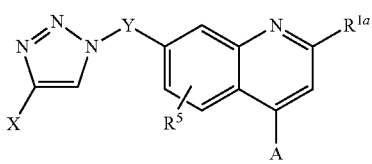

and the pharmaceutically acceptable salts thereof.

In another embodiment of this invention are compounds within the scope of Formula Ic having structural Formula Id wherein the variables are as defined in Formula I:

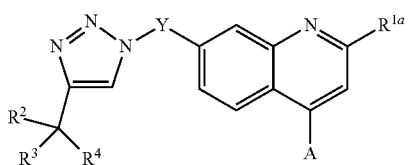

and the pharmaceutically acceptable salts thereof.

Additional embodiments of this invention include, but are not limited to, the following.

Within each of Formulas I, Ia, Ib, Ic and Id is a class of compounds (for convenience referred to as "Class A") wherein "A" is selected from (a) a 5-membered aromatic ring containing 3-4 carbon atoms and 1-2 heteroatoms selected from nitrogen, oxygen and sulfur, (b) pyridinyl, and (c) phenyl; wherein A is optionally mono- or di-substituted, and particularly wherein the 1-2 optional substituents are independently selected at each occurrence from —F, —Cl, $C_{1-3}$alkyl optionally substituted with one to five fluorines, and —$C_{1-3}$alkoxy optionally substituted with one to five fluorines. In a subclass of this class are compounds wherein A is phenyl optionally mono- or di-substituted, and particularly wherein the 1-2 optional substituents on the phenyl are independently selected at each occurrence from —F, —Cl, $C_{1-3}$alkyl optionally substituted with one to five fluorines, and —$C_{1-3}$alkoxy optionally substituted with one to five fluorines, and more particularly wherein the phenyl is mono- or di-substituted with —F.

Within each of Formulas I, Ia and Ib and compounds of Class A wherein $R^1$ is present, is a class of compounds (for convenience referred to as "Class B") wherein $R^1$ is selected from —H and —$C_{1-6}$ alkyl, and more particularly wherein $R^1$ is —H.

Within each of Formulas I, Ic and Id and compounds of Class A wherein $R^{1a}$ is present, is a class of compounds (for convenience referred to as "Class C") wherein $R^{1a}$ is selected from the group consisting of —H, cyano, and —$CONR^7R^8$ particularly —$CONH_2$, and more particularly wherein $R^{1a}$ is cyano.

Within each of Formulas I, Ia, Ib, Ic and Id and Classes A, B and C is a class of compounds (for convenience referred to as "Class D") wherein X is —$CR^2R^3R^4$.

Within each of Formulas I, Ia, Ib, Ic and Id and Classes A, B, C and D is a class of compounds (for convenience referred to as "Class E") wherein Y is —$CH_2$—.

Within each of Formulas I and Ia and Classes A, B, D and E wherein "-----" is present, is a class of compounds (for convenience referred to as "Class F") wherein "-----" is a double bond.

Within each of Formulas I, Ia, Ib, Ic and Id and Classes A, B, C, D, E and F, is a class of compounds (for convenience referred to as "Class G") wherein $R^2$ is selected from the group consisting of —H, —OH, —F, —$C_{1-3}$alkyl, —$OCH_3$, and —$OC(O)CH_3$. In a sub-class of this class are compounds wherein $R^2$ is selected from —H and —OH. In another sub-class of this class are compounds wherein $R^2$ is —OH.

Within each of Formulas I, Ia, Ib, Ic and Id and Classes A, B, C, D, E, F and G, is a class of compounds (for convenience referred to as "Class H") wherein $R^3$ is selected from the group consisting of —H, —$C_{1-6}$alkyl, —$C_{3-6}$cycloalkyl, phenyl and —$C_{1-6}$alkyl substituted with one or more of fluoro. In a sub-class of this class are compounds wherein $R^3$ is selected from —$CH_3$, —$C_2H_5$, —$C_{1-2}$alkyl substituted with fluoro particularly —$CF_3$ and —$CF_2CF_3$, and cyclopropyl. In another sub-class of this class are compounds wherein $R^3$ is selected from —$CH_2CH_3$ and cyclopropyl.

Within each of Formulas I, Ia, Ib, Ic and Id and Classes A, B, C, D, E, F, G and H, is a class of compounds (for convenience referred to as "Class I") wherein $R^4$ is selected from the group consisting of —H, —$C_{1-6}$alkyl, —$C_{3-6}$cycloalkyl, —$C_{1-6}$alkyl substituted with one or more of fluoro, and —$C_{1-6}$alkyl substituted with $R^6$. In a sub-class of this class are compounds wherein $R^4$ is selected from —$CH_3$, —$CH_2CH_3$, cyclopropyl, —$CH_2COOC_{1-4}$alkyl, and —$C_{1-2}$alkyl substituted with fluoro particularly —$CF_3$ and —$CF_2CF_3$. In another sub-class of this class are compounds wherein $R^4$ is selected from —$CF_3$, —$CH_2CH_3$ and cyclopropyl.

Within each of Formulas I, Ia and Ic and Classes A, B, C, D, E, F, G, H and I wherein $R^5$ is present, is a class of compounds (for convenience referred to as "Class J") wherein $R^5$ is selected from —H and —$C_{1-6}$ alkyl, and more particularly $R^5$ is —H.

Within each of Formulas I, Ia, Ib, Ic and Id and Classes A, B, C, D, E, F, G, H, I and J, is a class of compounds (for convenience referred to as "Class K") wherein: $R^2$ is selected from the group consisting of —H, —OH, —F, —$C_{1-3}$alkyl, —$OCH_3$, and —$OC(O)CH_3$; $R^3$ is selected from the group consisting of —H, —$C_{1-6}$alkyl, —$C_{3-6}$cycloalkyl, phenyl and —$C_{1-6}$alkyl substituted with one or more of fluoro; and $R^4$ is selected from the group consisting of —H, —$C_{1-6}$alkyl, —$C_{3-6}$cycloalkyl, —$C_{1-6}$alkyl substituted with one or more of fluoro, and —$C_{1-6}$alkyl substituted with $R^6$. In a sub-class of this class are compounds wherein $R^2$ is selected from —H and —OH; $R^3$ is selected from —$CH_3$, —$C_2H_5$, —$C_{1-2}$alkyl substituted with fluoro particularly —$CF_3$ and —$CF_2CF_3$, and cyclopropyl; and $R^4$ is selected from —$CH_3$, —$CH_2CH_3$, cyclopropyl, —$CH_2COOC_{1-4}$alkyl, and —$C_{1-2}$alkyl substituted with fluoro particularly —$CF_3$ and —$CF_2CF_3$. In a further sub-class within each of Formulas I, Ia, Ib, Ic and Id and each of Classes A through J are compounds wherein $R^2$ is —OH, $R^3$ is selected from —$CH_2CH_3$ and cyclopropyl, and $R^4$ is selected from —$CF_3$, —$CH_2CH_3$ and cyclopropyl. In yet a further sub-class within each of Formulas I, Ia, Ib, Ic and Id and each of Classes A through J are compounds wherein $R^2$ is —OH, $R^3$ is —$CH_2CH_3$ and $R^4$ is —$CF_3$.

The compounds of this invention, including compounds referenced as those of "Formula I," "Formula Ia," "Formula Ib," "Formula Ic," "Formula Id," or any other generic structural formulas used herein to describe the compounds of this invention, are intended to encompass compounds falling within the scope of each of these structural formulas including pharmaceutically acceptable salts, esters and solvates thereof where such salts, esters and solvates are possible.

Herein, the term "pharmaceutically acceptable salts" refers to non-toxic salts of the compounds employed in this invention which can generally be prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, morpholine, 2,4,4-trimethyl-2-pentamine and tris(hydroxymethyl) aminomethane. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Also, in the case of a carboxylic acid (—COOH) or alcohol group being present in the compounds of this invention, pharmaceutically acceptable esters of carboxylic acid derivatives can be employed. Examples of pharmaceutically acceptable esters include, but are not limited to, —$C_{1-4}$ alkyl (e.g., methyl, ethyl), pivaloyloxymethyl and —$C_{1-4}$ alkyl substituted with phenyl, dimethylamino and acetylamino. Acyl derivatives of alcohol groups, such as —O-acetyl, —O-pivaloyl, —O-benzoyl and —O-aminoacyl can similarly be employed. Included are those esters and acyl groups known in the art for modifying the solubility or hydrolysis characteristics of pharmaceutical compounds for use as pro-drugs or sustained-release or formulations.

Some of the compounds described herein contain one or more asymmetric centers and can thus occur as racemates, racemic mixtures, single enantiomers, diastereoisomeric mixtures and individual diastereoisomers. The present invention includes all such possible isomers in racemic, racemic mixture and resolved, enantiomerically pure forms and the pharmaceutically acceptable salts thereof. Furthermore, some of the crystalline forms of compounds of the present invention may exist as polymorphs and as such are intended to be included in the present invention. In addition, some of the compounds of the instant invention may form solvates with water or common organic solvents. Such solvates and hydrates are likewise encompassed within the scope of this invention. Some of the compounds described herein contain olefinic double bonds. The invention includes both E and Z geometric isomers.

Compounds of this invention may be separated into their individual diastereoisomers by, e.g., fractional crystallization from suitable solvents, e.g., methylene chloride/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, any stereoisomer of a compound of this invention may be obtained by stereospecific synthesis using optically pure starting materials or reagents of known absolute configuration.

As used herein "alkyl" is intended to include both branched- and straight-chain saturated aliphatic hydrocarbon groups having the specified number of carbon atoms, e.g., methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), isopentyl, isohexyl and the like. "Cycloalkyl" means a monocyclic saturated carbocyclic ring, having the specified number of carbon atoms, e.g., 3, 4, 5 or 6 carbon atoms. Examples of cycloalkyl include cyclopropyl, cyclobutyl, cyclopentyl and cyclohexyl.

The term "$C_{2-6}$alkenyl" as used herein, refers to a straight or branched 2-6 carbon chain with at least one carbon-carbon double bond. Examples of alkenyl include, but are not limited to, vinyl (—CH═$CH_2$), allyl, isopropenyl, pentenyl, hexenyl, 1-propenyl, 2-butenyl, 2-methyl-2-butenyl, and the like. The term "$C_{5-7}$ cycloalkenyl" as used herein means a non-aromatic monocyclic ring having from 5 to 7 carbon atoms in the ring with at least one carbon-carbon double bond.

The term "optionally" substituted means "unsubstituted or substituted," and therefore, the generic structural formulas described herein encompass compounds containing the specified optional substituent as well as compounds that do not contain the optional substituent. Each variable is independently defined each time it occurs within the generic structural formula definitions.

The term "heterocycle," and derivatives thereof such as "heterocyclyl" and "heterocyclic ring," mean an aromatic, partially unsaturated or saturated ring containing one or more carbon atoms and one or more heteroatoms such as nitrogen, oxygen and sulfur, but may be more specifically defined where appropriate in the specification, for example with respect to degree of saturation, number of members (i.e. atoms) in the ring and/or the type and quantity of heteroatoms in the ring. The term "heteroaryl" refers to a heterocyclic ring which is aromatic. The point of attachment in a compound structure may be via any carbon or nitrogen in the heterocyclic (or heteroaryl) ring which results in the creation of a stable structure. The heterocyclic ring may be substituted on any available carbon or nitrogen in the ring which results in the creation of a stable structure.

Examples of 5-membered aromatic rings containing one or more heteroatoms (i.e., heteroaryl rings) within the definition of A include but are not limited to thienyl, furanyl, oxazolyl, isoxazolyl, thiazolyl, isothiazolyl, pyrrolyl, pyrazolyl, imidazolyl, triazolyl and tetrazolyl.

Examples of 6-membered aromatic rings containing one or more heteroatoms (i.e., heteroaryl rings) within the definition of A include but are not limited to pyridinyl, pyridazinyl, pyrimidinyl, pyrazinyl and triazinyl. The instant invention also includes pyridinyl-N-oxide analogs of compounds containing a pyridinyl ring, and such analogs are included within the scope of Formula I and all other generic structural formulas described herein which may contain such a pyridinyl ring. For example in Formula I, when X is pyridinyl, both pyridinyl and pyridinyl-N-oxide are intended to be encompassed:

The ability of the compounds of this invention to inhibit biosynthesis of the leukotrienes makes them useful for preventing or reversing the symptoms induced by the leukotrienes in a human subject. Accordingly, this invention provides a method for preventing the synthesis, the action, or the release of leukotrienes in a mammal which comprises administering to said mammal a 5-LO inhibitory effective amount of a compound of this invention. Such 5-LO inhibitory activity can be measured using the Human 5-Lipoxygenase Enzyme Assay and 5-Lipoxygenase Human Whole Blood Assay described herein. Since leukotrienes are potent inflammatory mediators, also provided is method of treating an inflammatory condition in a mammal which comprises administering a therapeutically effective amount of a compound of this invention to a mammal in need of such treatment.

The inhibition of the mammalian biosynthesis of leukotrienes also indicates that the compounds and pharmaceutical compositions thereof are useful to treat, prevent or ameliorate atherosclerosis in mammals, and especially in humans. Therefore, the compounds of this invention can be used for the treatment of atherosclerosis comprising administering a therapeutically effective amount of a compound of this invention to a patient in need of such treatment.

The method of this invention serves to prevent or slow new atherosclerotic lesion or plaque formation, and to prevent or slow progression of existing lesions or plaques, as well as to cause regression of existing lesions or plaques. Accordingly, one aspect of this invention encompassed within the scope of treatment of atherosclerosis involves a method for halting or slowing the progression of atherosclerosis, including halting or slowing atherosclerotic plaque progression, comprising administering a therapeutically effective amount of a compound of this invention to a patient in need of such treatment. This method includes halting or slowing progression of atherosclerotic plaques existing at the time the instant treatment is begun (i.e., "existing atherosclerotic plaques"), as well as halting or slowing formation of new atherosclerotic plaques in patients with atherosclerosis.

Another aspect of this invention encompassed within the scope of treatment of atherosclerosis involves a method for effecting regression of atherosclerosis, including effecting regression of atherosclerotic plaques existing at the time the instant treatment is begun, comprising administering a therapeutically effective amount of a compound of this invention to a patient in need of such treatment.

Also provided is a method comprising administering to a patient who has atherosclerosis a compound of this invention with the objective of preventing or reducing the risk of atherosclerotic plaque rupture. Therefore, this invention provides a method for preventing or reducing the risk of atherosclerotic plaque rupture comprising administering a prophylactically effective amount of a compound of this invention to a patient having atherosclerotic plaque.

This invention also involves a method for preventing or reducing the risk of developing atherosclerosis, comprising administering a prophylactically effective amount of a compound of this invention to a patient in need of such treatment, including, for example, a patient who is at risk for developing atherosclerosis.

Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A compound of the instant invention may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a compound of this invention to a patient in need of such treatment, such as a patient who is at risk for such an event. The patient in need of such treatment may already have atherosclerotic disease at the time of administration, or may be at risk for developing it.

This invention also provides a method for treating, preventing, or ameliorating angina and/or myocardial ischemia, comprising administering a therapeutically or prophylactically effective amount, as appropriate, of a compound of this invention to a patient in need of such treatment.

Additionally, the activity of the instant compounds as leukotriene biosynthesis inhibitors makes them useful for treating, preventing, or ameliorating: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, 16) multiple sclerosis, 17) proliferation of myoblastic leukemia cells, 18) pulmonary fibrosis, 19) respiratory syncytial virus, 20) acne and 21) sleep apnea.

Particularly, the compounds of this invention can be administered to patients, including adult and pediatric patients, for the prophylaxis of asthma and for chronic treatment of asthma. The compounds of this invention can be administered to patients, including adult and pediatric patients, for the treatment of asthma: (1) as an alternative to low-dose inhaled corticosteroids (ICS) for patients with mild persistent asthma, (2) as concomitant therapy with low-dose inhaled corticosteroids (ICS) for patients with mild persistent asthma, or (3) as concomitant therapy in patients with persistent asthma who are inadequately controlled on inhaled corticosteroids (ICS) or on combined ICS/long-acting beta-agonist (LABA) therapy. The compounds can be used for treatment of asthmatic patients including, but not limited to, steroid resistant/non-responder asthmatics, asthmatics for whom leukotriene modifiers have previously failed, smoking asthmatics, and aspirin sensitive asthmatics.

The compounds can be administered to patients to: (1) improve FEVI (Forced Expiratory Volume in one minute), (2) improve morning and evening PEF (Peak Expiratory flow), (3) reduce beta-agonist use (measured by puffs/day), (4) reduce inhaled/systemic steroid use. (5) improve daytime asthma symptoms, (6) reduce number of nocturnal awakenings, 7) improve asthma control days, (8) reduce number of asthma exacerbations, wherein an exacerbation is defined as: requiring systemic steroid, an emergency room visit, hospitalization, an unscheduled asthma related doctor visit, decrease in A.M. PEF by >20% or A.M. PEF <180 l/min, increased SABA (short-acting beta-agonist) use >70% from baseline (minimum increase 2 puffs), or increased symptom score of >50%, (9) reduce the number of asthma attacks (measured as % of days with at least one attack over a specified period of total days), wherein the attack is one that requires systemic steroid use, an emergency room visit, hospitalization, or an unscheduled asthma related doctor visit, (10) reduce the number of acute asthma attacks, (11) reduce blood and sputum eosinophils, and/or (12) prevent and treat EIB (exercised induced bronchoconstriction).

Additionally, the compounds of this invention can be administered to patients, including adult and pediatric patients, for the relief of symptoms of allergic rhinitis, including seasonal and perennial allergic rhinitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. Leukotriene biosynthesis inhibitors also act as inhibitors of tumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like. Two assays can be used to measure cytoprotective ability. These assays are: (A) an ethanol-induced lesion assay and (B) an indomethacin-induced ulcer assay and are described in EP 140,684. In particular, the compounds of the invention would be useful to reduce the gastric erosion caused by co-administration of a cyclooxygenase-2 selective inhibitor such as rofecoxib (VIOXX®), etoricoxib (ARCOXIA™), and celecoxib (CELEBREX®) and low-dose aspirin.

In addition, the compounds of this invention can also be used for the treatment of chronic obstructive pulmonary disease (COPD). As described in S. Kilfeather, Chest, 2002, vol 121, 197, airway neutrophilia in COPD patients is believed to be a contributing source of inflammation and is associated with airway remodeling. The presence of neutrophils is mediated in part by $LTB_4$, and treatment with the instant compounds could be used to reduce neutrophilic inflammation in patients with COPD and reduce the rate of COPD exacerbations. In particular, the compounds of this invention could be used for daily, preferably once-daily, maintenance treatment of airflow obstruction associated with COPD, including chronic bronchitis and emphysema.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by inhibition of leukotriene biosynthesis.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. A therapeutically effective amount or prophylactically effective amount, as appropriate, of a compound of Formula I is intended for use in the methods and pharmaceutical compositions of this invention.

The magnitude of prophylactic or therapeutic dose of a compound of this invention will, of course, vary with the nature of the severity of the condition to be treated and with the particular compound and its route of administration. It will also vary according to the age, weight and response of the individual patient. It is understood that a specific daily dosage amount can simultaneously be both a therapeutically effective amount, e.g., for treatment to slow progression of existing atherosclerosis, and a prophylactically effective amount, e.g., for prevention of an atherosclerotic disease event or formation of new lesions. In general, the daily dose range for anti-asthmatic, anti-inflammatory, anti-allergic or anti-atherosclerotic use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

In the case where an oral composition is employed, a suitable daily dosage range for anti-asthmatic, anti-inflammatory, anti-allergic or anti-atherosclerotic use is, e.g., from about 0.01 mg to about 100 mg of a compound of this invention per kg of body weight per day, and preferably from about 0.1 mg to about 10 mg per kg. For cytoprotective use a suitable daily dosage range is from 0.1 mg to about 100 mg, preferably from about 1 mg to about 100 mg, and more preferably from about 10 mg to about 100 mg, of a compound of this invention per kg of body weight per day.

For use where a composition for intravenous administration is employed, a suitable daily dosage range for anti-asthmatic, anti-inflammatory, anti-atherosclerotic or anti-allergic use is from about 0.001 mg to about 25 mg (preferably from 0.01 mg to about 1 mg) of a compound of this invention per kg of body weight per day and for cytoprotective use from about 0.1 mg to about 100 mg (preferably from about 1 mg to about 100 mg and more preferably from about 1 mg to about 10 mg) of a compound of this invention per kg of body weight per day. For the treatment of diseases of the eye, ophthalmic preparations for ocular administration comprising 0.001-1% by weight solutions or suspensions of the compounds of this invention in an acceptable ophthalmic formulation may be used.

The exact amount of a compound of this invention to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of this invention in avoiding future damage would be co-administration of a compound of this invention with an NSAID that might otherwise cause such damage (for example, indomethacin). For such use, the compound of this invention is administered from 30 minutes prior up to 30 minutes after administration of the NSAID. Preferably it is administered prior to or simultaneously with the NSAID, (for example, in a combination dosage form).

The pharmaceutical compositions of the present invention comprise a compound of this invention as an active ingredient and a pharmaceutically acceptable carrier and optionally other therapeutic ingredients. Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. For use in treating or preventing atherosclerosis and related disease events, oral formulation is preferred.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of this invention in suitable propellants, such as fluorocarbons or hydrocarbons.

Suitable topical formulations of a compound of this invention include transdermal devices, aerosols, creams, ointments, lotions, dusting powders, and the like.

In practical use, the compounds of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of this invention may also be administered by controlled release means and/or delivery devices such as those described in U.S. Pat. Nos. 3,845,770; 3,916,899; 3,536,809; 3,598,123; 3,630,200; 4,008,719; and 5,366,738 the disclosures of which are incorporated herein by reference.

Pharmaceutical compositions of the present invention suitable for oral administration may be presented as discrete units such as capsules, cachets or tablets, each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet, cachet or capsule contains from about 1 mg to about 500 mg of the active ingredient, for example but not limited to 10 mg, 20 mg, 30 mg, 40 mg, 50 mg and 75 mg. The following are examples of representative pharmaceutical dosage forms for the compounds of this invention:

| Injectable Suspension (I.M.) | mg/ml |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
| --- | --- |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

The instant invention also encompasses a process for preparing a pharmaceutical composition comprising combining a compound of this invention with a pharmaceutically acceptable carrier. Also encompassed is the pharmaceutical composition which is made by combining a compound of this invention with a pharmaceutically acceptable carrier.

A therapeutically effective amount of a compound of this invention can be used for the preparation of a medicament useful for treating or preventing any of the medical conditions described herein, in dosage amounts described herein. For example, a compound of this invention can be used for the preparation of a medicament useful for preventing or reducing the risk of developing atherosclerotic disease, halting or slowing the progression of atherosclerotic disease once it has become clinically manifest, and preventing or reducing the risk of a first or subsequent occurrence of an atherosclerotic disease event. Additionally, a compound of this invention can be used for the preparation of a medicament useful for the treatment of asthma, allergies and allergic conditions, inflammation, COPD or erosive gastritis. The medicament comprised of a compound of this invention may also be prepared with one or more additional active agents, such as those described below.

One or more additional active agents may be used in combination with the compounds of this invention in a single dosage formulation, or the active agents of the combination may be administered to the patient in separate dosage formulations, which allows for concurrent or sequential administration of the active agents. Unless otherwise specified, reference herein to compounds of this invention being used in combination with other active agents or used as part of combination therapy or the like encompasses both a single pharmaceutical composition comprised of a compound of this invention with one or more additional active agents, as well as a pharmaceutical composition comprised of a compound of this invention administered as part of a combination therapy with one or more other separately formulated active agents.

In addition to the compounds of this invention, the pharmaceutical compositions of the present invention can also contain other active agents (i.e., ingredients) and the pharmaceutical compositions comprised of a compound of this invention may be used for combination therapy with one or more other separately formulated active agents, such as cyclooxygenase inhibitors, non-steroidal anti-inflammatory drugs (NSAIDs), peripheral analgesic agents such as zomepirac diflunisal and the like. The weight ratio of the compound of this invention to the second active ingredient may be varied and will depend upon the effective dose of each ingredient. Generally, an effective dose of each will be used. Thus, for example, when a compound of this invention is combined with an NSAID the weight ratio of the compound of said compound to the NSAID will generally range from about 1000:1 to about 1:1000, preferably about 200:1 to about 1:200. Combinations of a compound of this invention and other active ingredients will generally also be within the aforementioned range, but in each case, an effective dose of each active ingredient should be used.

NSAIDs can be characterized into five groups: (1) propionic acid derivatives; (2) acetic acid derivatives; (3) fenamic acid derivatives; (4) oxicams; and (5) biphenylcarboxylic acid derivatives; or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group. Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group. Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g., —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group. Thus, "fenamic acid derivatives" as defined herein are non-narcotic analgesics/non-steroidal anti-inflammatory drugs which contain the basic structure:

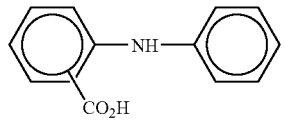

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenyl-carboxylic acid derivatives having similar analgesic and anti-inflammatory properties are also intended to be encompassed by this group. Thus, "biphenylcarboxylic acid derivatives" as defined herein are non-narcotic analgesics/non-steroidal anti-inflammatory drugs which contain the basic structure:

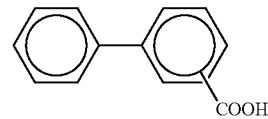

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group. Thus, "oxicams" as defined herein are non-narcotic analgesics/non-steroidal anti-inflammatory drugs which have the general formula:

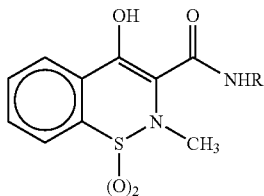

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate. The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin. Pharmaceutical compositions and combinations comprising compounds of this invention may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of this invention may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions and combinations comprising compounds of this invention may also contain as the second active ingredient, or be used in combination therapy with, prostaglandin antagonists such as those disclosed in EP 11,067 (May 28, 1980) or thromboxane antagonists such as those disclosed in U.S. Pat. No. 4,237,160. They may also contain or be used with histidine decarboxylase inhibitors such as α-fluoromethylhistidine, described in U.S. Pat. No. 4,325,961. The compounds of this invention may also be advantageously combined with an $H_1$ or $H_2$-receptor antagonist, such as for instance acetamazole, aminothiadiazoles disclosed in EP 40,696 (Dec. 2, 1981), diphenhydramine, cimetidine, famotidine, framamine, histadyl, promethazine, ranitidine, terfenadine, fexofenadine, loratadine, desloratadine and cetirazine and like compounds, such as those disclosed in U.S. Pat. Nos. 4,283,408; 4,362,736; and 4,394,508. The pharmaceutical compositions may also contain or be used in combination with a $K^+/H^+$ ATPase inhibitor such as omeprazole, disclosed in U.S. Pat. No. 4,255,431, and the like. Compounds of this invention may also be usefully combined with mast cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises compounds of this invention in combination with serotonin antagonists such as methysergide, the serotonin antagonists described in Nature, 316, 126-131 (1985), and the like. Each of the references referred to in this paragraph is hereby incorporated herein by reference.

Other advantageous pharmaceutical combinations comprise the compounds of this invention in combination with anti-cholinergics such as ipratropium bromide and tiotropium, bronchodilators such as the beta agonist salbutamol, metaproterenol, terbutaline, fenoterol, salmeterol, formoterol and the like, and the anti-asthmatic drugs theophylline, choline theophyllinate and enprofylline, the calcium antagonists nifedipine, diltiazem, nitrendipine, verapamil, nimodipine, felodipine, etc., and the corticosteroids, hydrocortisone, methylprednisolone, betamethasone, dexamethasone, beclomethasone, and the like.

Particularly, for the prophylaxis and treatment of asthma, compounds of this invention can be used in combination with orally inhaled corticosteroids, such as beclomethasone (e.g. QVAR® Inhalation Aerosol), budesonide (e.g. Pulmicort Respules), flunisolide (e.g., AEROBID® and AEROBID®-M Inhaler System), fluticasone (e.g., FLOVENT® DISKUS® inhalation powder, FLOVENT® HFA Inhalation Aerosol), mometasone (e.g., ASMANEX® TWISTHALER®), and triamcinolone (e.g., AZMACORT® Inhalation Aerosol), and also with inhaled corticosteroid/LABA products such as fluticasone propionate/salmeterol (e.g., ADVAIR DISKUS®). The instant compounds could also be used in combination with leukotriene receptor antagonists such as montelukast (e.g., SINGULAIR®), zafirlukast (ACCOLATE®), and pranlukast; phosphodiesterase 4 (PDE4) inhibitors such as roflumilast, N-Cyclopropyl-1-[3-(1-oxido-3-pyridinylethynyl)phenyl]-1,4-dihydro[1,8]naphthyridin-4-one-3-carboxamide and the compounds disclosed in PCT Publication WO2003/018579; and Very Late Antigen 4 (VLA4) inhibitors such as the compounds disclosed in U.S. Pat. No. 6,229,011, particularly R411 (N-(2-Chloro-6-methylbenzoyl)-4-[(2,6-dichlorobenzoyl)amino]-L-phenylalanine-2-(diethylamino)-ethyl ester which is an ester pro-drug of the active moiety, N-(2-chloro-6-methylbenzoyl)-4-[(2,6-dichlorobenzoyl)amino]-L-phenylalanine), and the compounds disclosed in PCT publication WO2006/023396.

Furthermore, additional active agents such as anti-atherosclerotic agents, anti-diabetes agents, anti-obesity agents and agents used for the treatment of metabolic syndrome, may be used in combination with the compounds of this invention. The additional active agent or agents can be lipid altering compounds such as HMG-CoA reductase inhibitors, or agents having other pharmaceutical activities, or agents that have both lipid-altering effects and other pharmaceutical activities. Examples of HMG-CoA reductase inhibitors useful for this purpose include statins in their lactonized or dihydroxy open acid forms and pharmaceutically acceptable salts and esters thereof, including but not limited to lovastatin (MEVACOR®; see U.S. Pat. No. 4,342,767); simvastatin (ZOCOR®; see U.S. Pat. No. 4,444,784); dihydroxy open-acid simvastatin, particularly the ammonium or calcium salts thereof, pravastatin, particularly the sodium salt thereof (PRAVACHOL®; see U.S. Pat. No. 4,346,227); fluvastatin particularly the sodium salt thereof (LESCOL®; see U.S. Pat. No. 5,354,772); atorvastatin, particularly the calcium salt thereof (LIPITOR®; see U.S. Pat. No. 5,273,995); pitavastatin also referred to as NK-104 (see PCT international publication number WO 97/23200); and rosuvastatin (CRESTOR®; see U.S. Pat. No. 5,260,440). Additional active agents which may be employed in combination with a compound of this invention include but are not limited to HMG-CoA synthase inhibitors; cholesterol absorption inhibitors such as ezetimibe (ZETIA®) which is 1-(4-fluorophenyl)-3 (R)-[3(S)-(4-fluorophenyl)-3-hydroxypropyl)]-4(S)-(4-hydroxyphenyl)-2-azetidinone, described in U.S. Pat. Nos. Re. 37721 and 5,846,966 as well as a fixed dose combination of ezetimibe and simvastatin (VYTORIN®); HDL-raising agents such as cholesterol ester transfer protein (CETP) inhibitors, for example JTT-705 (Japan Tobacco Company) and torcetrapib (Pfizer); squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example troglitazone, pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate and gemfibrozil; PPAR dual α/γ agonists such as muraglitazar; vitamin $B_6$ (also known as pyridoxine) and the pharmaceutically acceptable salts thereof such as the HCl salt; vitamin B12 (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan and losartan with hydrochlorothiazide; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib, etoricoxib and celecoxib. Anti-obesity agents can be employed in combination with a compound of this invention including, but not limited to, sibutramine, orlistat, topiramate, naltrexone, bupriopion, phentermine, and phentermine/topiramate combination (QNEXA®); NPY5 antagonists; Acetyl-CoA Carboxylase-1 and -2 (ACC) inhibitors; MCH1R antagonists; and CB1 antagonists/inverse agonists such as those described in WO03/077847 and WO05/000809. Additional anti-diabetes agents which may be employed in combination with a compound of this invention include but are not limited to DPP-4 (dipeptidylpeptidase-4) inhibitors such as sitagliptin (JANUVIA®) and vildagliptin (GALVUS®); sulfonylureas e.g., chlorpropamide, tolazamide, glyburide, glipizide, and glimepiride; biguanides, e.g., metformin; alpha-glucosidase inhibitors e.g., acarbose and miglitol; meglitinides e.g., repaglinide; glucagon-receptor agonists; and glucokinase activators.

Compounds of this invention can be tested using the following assays to determine their mammalian leukotriene biosynthesis inhibiting activity. Representative tested compounds of this invention were shown to be inhibitors of leukotriene biosynthesis, with most having an $IC_{50}$ less than or equal to 4 μM in the Human 5-Lipoxygenase Enzyme Assay, described below, with preferred compounds tested in this assay having an $IC_{50}$ less than or equal to 0.100 μM. To illustrate, $IC_{50}$ (in nM) of several exemplified compounds are provided: Example 1: 38; Example 2: 50; Example 3: 1215; Example 5: 45; Example 8: 50; Example 12 324; Example 16: 442; Example 22: 951; Example 26: 98; Example 27: 298; Example 30: 37; Example 37: 351; Example 39: 34; Example 40: 54; Example 41: 51; Example 43: 275; Example 46: 103; Example 47: 62; Example 48: 82; Example 57: 86; Example 58: 52; Example 69: 35; Example 71: 55; Example 87: 17; Example 88: 41. The representative tested compounds were also shown to have activity as 5-LO inhibitors in the 5-Lipoxygenase Human Whole Blood Assay, described below, with most having an $IC_{50}$ less than or equal to 5 μM, and preferred compounds having an $IC_{50}$ of less than or equal to 0.500 μM.

Human 5-Lipoxygenase Enzyme Assay

The activity of 5-lipoxygenase was measured using a spectrophotometric assay and recombinant human 5-lipoxygenase as a source of enzyme. Human 5-lipoxygenase was purified from Sf9 cells infected with the recombinant baculovirus rvH5LO (8-1) containing the coding sequence for human 5-lipoxygenase as described by Percival et al., (Eur. J. Biochem 210, 109-117, 1992). The enzymatic activity was measured using a spectrophotometric assay from the optimal rate of conjugated diene formation (absorbance at 238 nm) using the procedure described in Riendeau et al. (Biochem. Pharmacol. 38, 2313-2321, 1989) with minor modifications. The incubation mixture contained 25 mM potassium phosphate, pH 7.5, 0.1 mM EDTA, 0.3 mM $CaCl_2$, 24 μg/ml phosphatidylcholine, 0.1 mM ATP, 0.5 mM DTT, 20 μM arachidonic acid (2 μl from a 100-fold solution in ethanol), inhibitor (2 μl aliquot from a 100-fold solution in DMSO) and an aliquot of purified 5-lipoxygenase. Reactions were initiated by the addition of the purified 5-lipoxygenase and the rate of conjugated diene production was followed for 5 minutes at room temperature. The reaction was performed in a Costar UV plate (Cat. # 3635) and the absorbance changes at 238 nm were recorded with a Molecular Devices UV/VIS 96 well spectrophotometer (Spectra Max 190) using SOFTmax PRO software. Enzymatic activity was calculated from the optimal rate of the reaction by a linear fit of the increase in absorbance at 238 nm over 36 seconds. When the rate of diene formation is low (<0.01 Absorbance Unit/min) the linear fit is performed over 180 seconds. The results are expressed as percentage of inhibition of the reaction rate relative to controls (typically between 0.001-0.005 Absorbance Unit/min) containing the DMSO vehicle.

5-Lipoxygenase Human Whole Blood Assay

Fresh blood is collected in heparinized tubes by venipuncture from volunteers with consent. The subjects have no apparent inflammatory conditions and have not taken any nonsteroidal anti-inflammatory drugs for at least 4 days prior to blood collection. 250 μl aliquots of blood are pre-incubated with either 0.5 μl of vehicle (DMSO) or test compound at 37° C. for 15 minutes. This is followed by incubation of the blood with 5 μl of either plasma or a 1.25 mM solution of the calcium ionophore A23187 (Sigma, St Louis, Mo., USA) in plasma. The latter solution is prepared by centrifuging approximately 10 mls of blood from each donor and collecting the plasma. A 50 mM stock solution of A23187 in DMSO is diluted 40-fold in plasma to yield a 1.25 mM working solution. Five μls of this working solution is added to each appropriate 250 μl-aliquot of blood of the same donor from which the plasma was prepared to give a final concentration of 25 μM of A23187. The blood is then incubated at 37° C. for 30 minutes. Following incubation, the blood is centrifuged at 1500 g at 4° C. for 10 minutes. Plasma is then collected from all samples and stored at 4° C. until time of enzyme immunosorbent assay (EIA). All samples are tested for the production of leukotriene B4 (LTB4) using the LTB4 EIA kit from Assay Designs (Ann Arbor, Mich., USA) according to the manufacturer's instructions.

Compounds of this invention may be prepared employing general synthetic procedures known in the art. The synthetic routes outlined in the following methods, reaction schemes and Examples are provided for illustrative purposes.

Some abbreviations used herein include: Ac=acyl; AIBN=2,2'-azobisisobutyronitrile; BuLi=butyllithium; Bz or bz=benzyl; CAN=cerium ammonium nitrate; CDI=1,1'-carbonyl diimidazole; cy=cyclohexyl; DAST=diethylaminosulfur trifluoride; DBU=1,8-diazabicyclo[5.4.0]undec-7-ene; DCC=1,3-dicyclohexylcarbodiimide; DCM=dichloromethane; DIAD=diisopropyl azodicarboxylate; DIBAL=diisobutylaluminum hydride; DIPEA=N,N-diisopropylethylamine; DMAP=4-(dimethylamino) pyridine; DME=ethylene glycol dimethyl ether; DMF=N,N-dimethylformamide; DMSO=dimethyl sulfoxide; eq=equivalent; EtOH=ethanol; Et$_2$O=diethyl ether; Et$_3$N=triethylamine; EtOAc=ethyl acetate; h=hours; $^1$H NMR is proton nuclear magnetic resonance; HOAc=acetic acid; HPLC=high performance liquid chromatography; KHMDS=potassium bis(trimethylsilyl)amide; LAH=lithium aluminum hydride; LDA=lithium diisopropylamide; m-CPBA (or MCPBA)=3-chloroperoxybenzoic acid; MS=mass spectrum; MS-APCI=mass spectrum-Atmospheric Pressure Chemical Ionization; MsCl=methanesulphonyl chloride; MeOH=methanol; MTBE=methyl t-butyl ether; NBS=N-bromosuccinimide; NCS=N-chlorosuccinimide; NMO=4-methylmorpholine N-oxide; NMP=1-methyl-2-pyrrolidinone; OTf=trifluoromethanesulfonate=triflate; O-THP=O-tetrahydropyran-2-yl; Ph=phenyl; PPTS=pyridinium p-toluenesulfonate; Py=pyridine; rt=room temperature; TBAF=tetrabutylammonium fluoride; Tf$_2$O=triflic anhydride (also known as trifluoromethanesulfonic anhydride); TFA=trifluoro acetic acid; TFAA=trifluoroacetic anhydride; THF=tetrahydrofuran; TMS=trimethylsilyl; TMSCN=trimethylsilyl cyanide.

7-Bromo-4-trifluoromethanesulfonyloxycoumarin 4 can be prepared as shown below in Scheme 1. Description of how to make 4 is also found in the procedures described in U.S. Pat. No. 5,552,437 in Scheme 1 at columns 17-18 (see structure V) therein and in the section titled "Preparation Of Coumarins" starting at column 58 therein. Bromophenol 1 can be acetylated by treating a mixture of 1 and acetyl chloride in the presence of a base such as pyridine in a solvent such as dichloromethane to yield the corresponding acetate which, upon heating neat with a Lewis acid such as aluminum chloride, gives the acyl derivative 2. Reaction of 2 with first an inorganic base such as sodium hydride in an organic solvent such as benzene followed by addition of a carbonate such as diethylcarbonate furnishes the intermediate 3. The intermediate 3 is then transformed using trifluoromethanesulfonic anhydride, in the presence of an amine such as triethylamine, in a neutral solvent such as dichloromethane, to the corresponding bromocoumarin triflate 4.

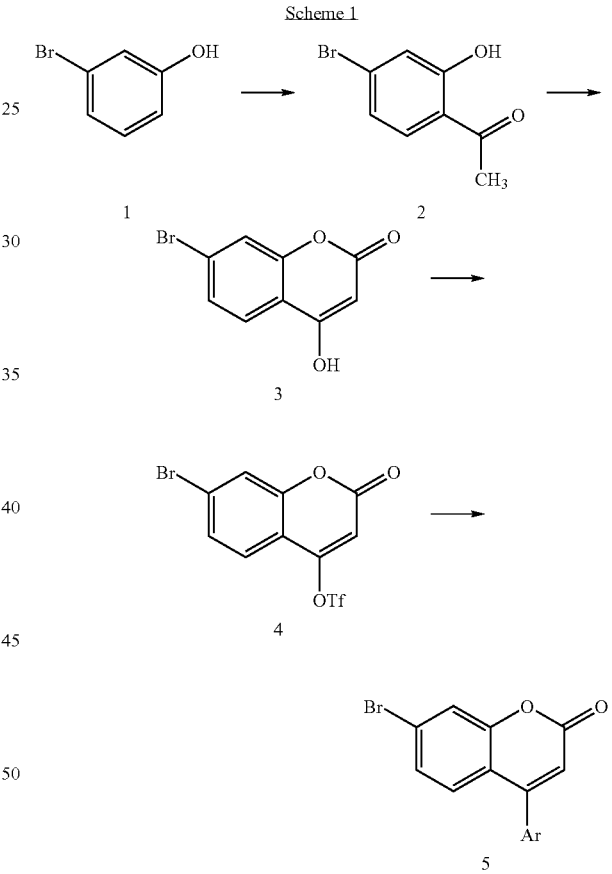

Cross coupling of 4 with an aryl lithium species resulting from reaction of an aryl halide (Br or I) with an alkyl lithium such as n-BuLi in a mixture of THF/hexanes, in the presence of trimethyl borate and catalyzed by a Pd(0) species such as (Ph$_3$P$_4$)Pd, in a mixture of THF/water as solvent, affords derivatives 5, wherein Ar represents aryl (e.g., phenyl), heteroaryl and heterocyclic groups as described within the scope of Formula I.

The starting material shown in Coumarin Scheme A can be prepared from the meta-cresol 6, which is converted in several steps to 8 using the same protocol as described in Scheme 1 for the conversion of 1 to 5.

Scheme 2

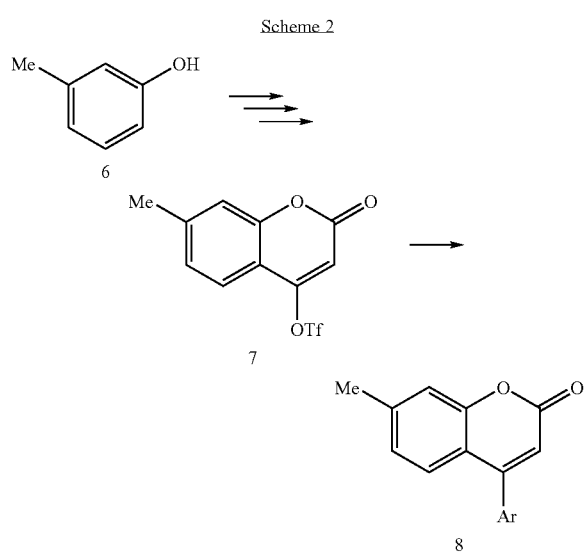

Description of how to make 4, 5, 7 and 8 is also found in the procedures described in U.S. Pat. No. 5,552,437 in Schemes 1 and 2 therein (see columns 12, 13, 17-19) and in the section titled "Preparation Of Coumarins" starting at column 58 therein.

Coumarin Method A:

The starting coumarin derivatives are prepared according to literature procedures (U.S. Pat. No. 5,552,437, WO 2006/099735). The methyl group is brominated with NBS and heating in an inert solvent such as $CCl_4$ in the presence of a radical initiator such as benzoyl peroxide, AIBN, or light. The bromide is converted to the azide with sodium azide in ethanol and reacted with an alkyne in the presence of copper(I) iodide and Hünig's base in THF to furnish the corresponding triazole derivative. Hydrolysis of the ester can be accomplished with lithium hydroxide in THF. The alkyne derivatives are prepared by reacting the lithio derivative of TMS protected acetylene with ketones at low temperature in THF. Treatment with tetrabutylammonnium fluoride in THF liberates the unprotected alkyne. Alternatively, the tertiary alcohol of the primary adduct with trifluoromethylethylketone can be protected with p-nitrobenzoyl chloride in DMF and this adduct can be separated into its enantiomers by chiral HPLC methods.

Coumarin Scheme A:

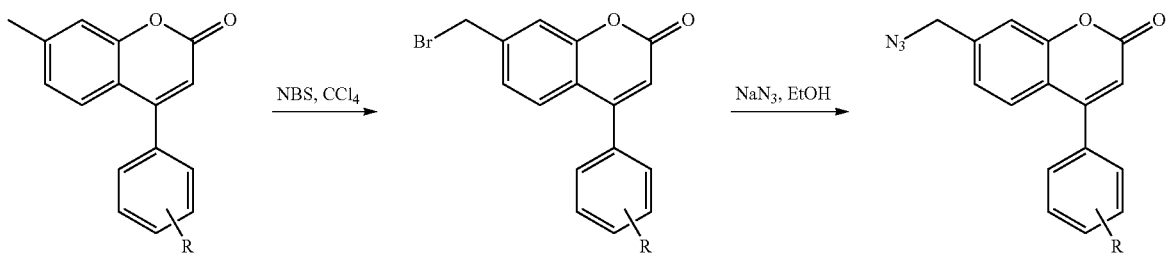

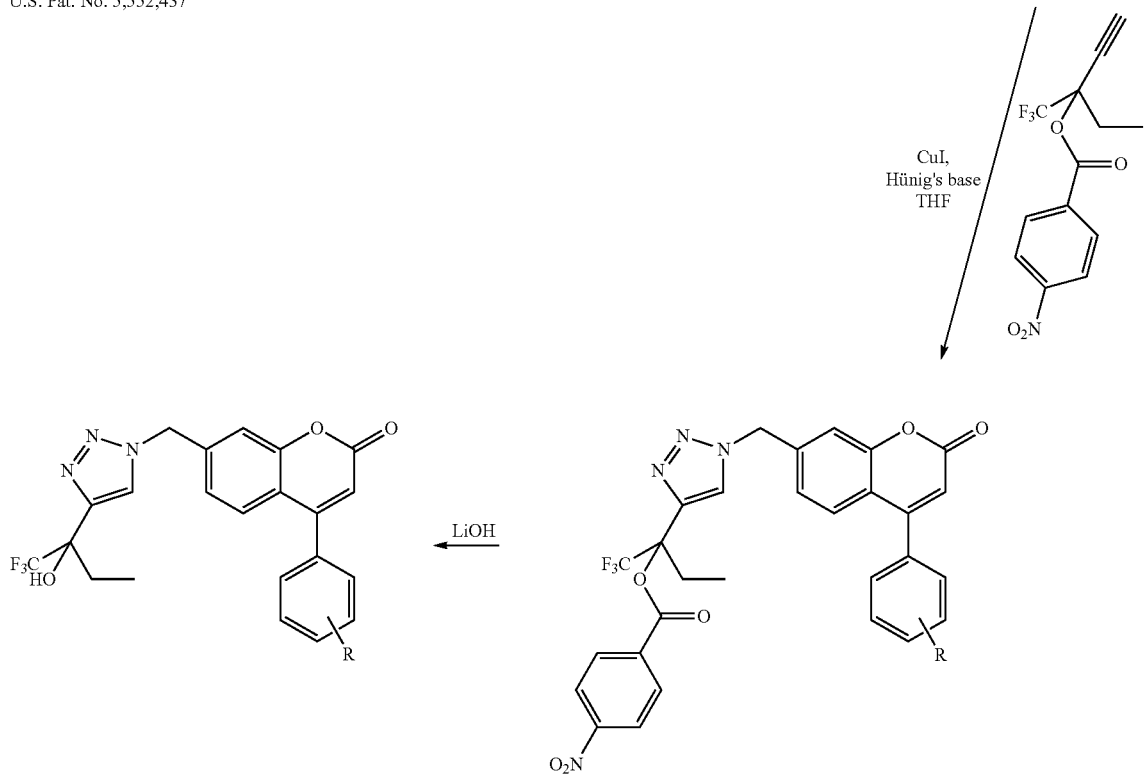

-continued

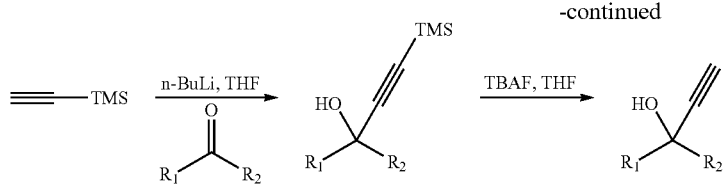

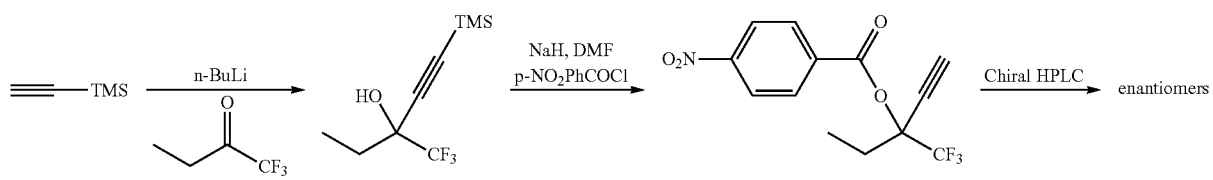

Coumarin Method B:

The bromocoumarin triflate can be reacted with boronic acids in the presence of a palladium catalyst under Suzuki coupling conditions to give the 4-substituted coumarin derivative. Carbonylation under carbon monoxide atmosphere with a palladium catalyst and methanol/DMF as solvent gives rise to the methylester. Reduction of the ester to the alcohol can be accomplished via saponifaction of the ester with LiOH in THF and subsequent reaction with isobutyl-chloroformate (IBCF), triethylamine in THF followed by treatment with NaBH$_4$. The alcohol is converted to the azide with PPh$_3$, an activating agent such as diisopropyl azodicarboxylate (DIAD) and zinc azide. The azide derivative can be reacted with an alkyne in the presence of copper(I) iodide and Hünig's base in THF to furnish the corresponding triazole derivative.

Coumarin Scheme B:

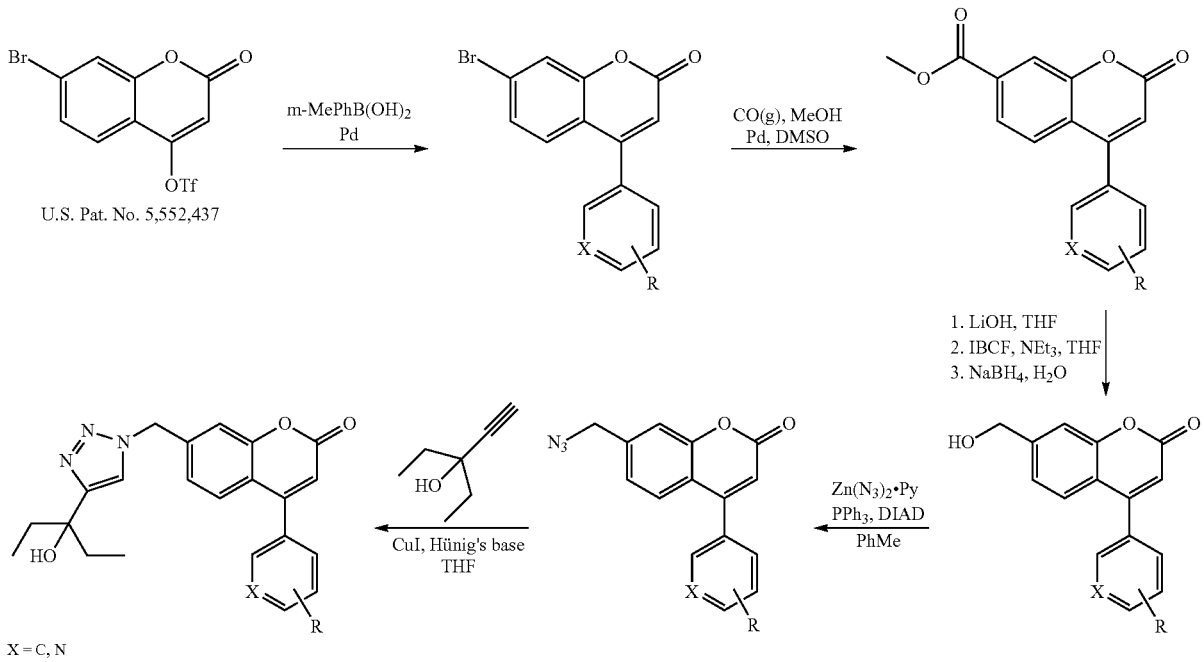

Coumarin Method C:

The cresol derivative can be ortho-metalated with a strong base such as t-BuLi and reacted with a carbonyl compound to give the corresponding ketone. After deprotection of the phenol, cyclization to the coumarin can be accomplished with a Wittig reagent in toluene. This is followed by bromination, azide displacement, and triazole formation as described above. Treatment of the ester with LiOH in THF gives the corresponding tertiary alcohol.

Coumarin Scheme C:

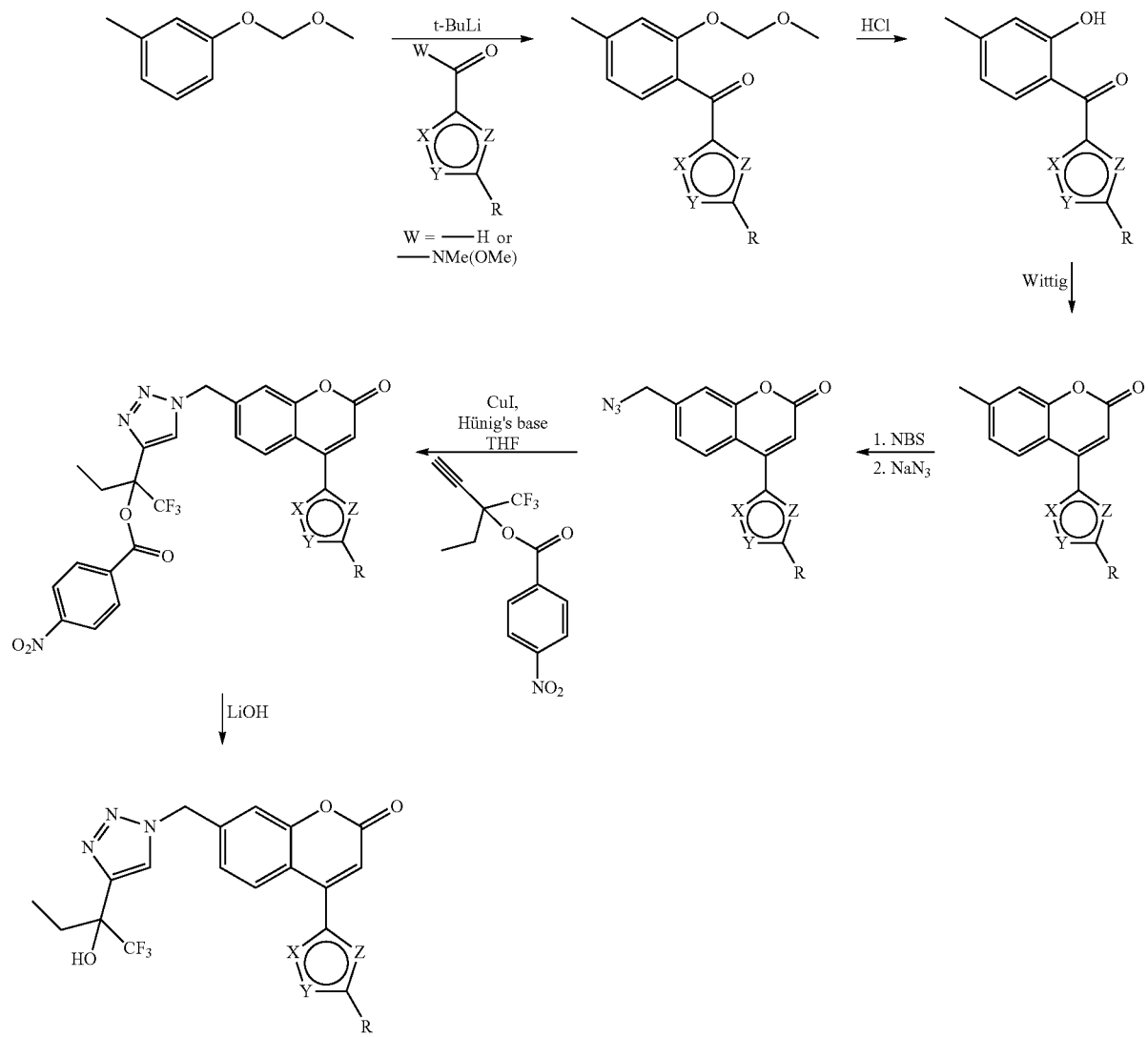

Coumarin Method D:

The triflate (U.S. Pat. No. 5,552,437) can be reacted with tributyl(1-ethoxyvinyl)tin and a catalyst such as Pd(PPh$_3$)$_4$ under Stille coupling conditions to give the vinyl ether. Bromination can be achieved with a bromide source such as NBS.

This bromoketone can be converted to an oxazole by treatment with acetamide in DMF at elevated temperature. This is followed by bromination, azide displacement, and triazole formation as described above. Treatment of the ester with LiOH in THF gives the corresponding tertiary alcohol.

Coumarin Scheme D:

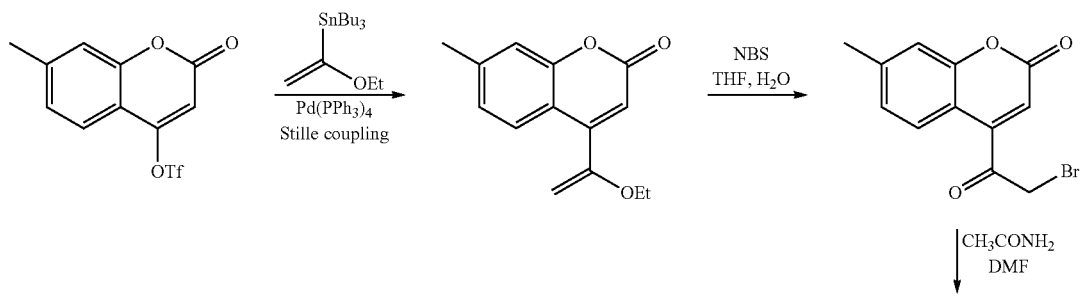

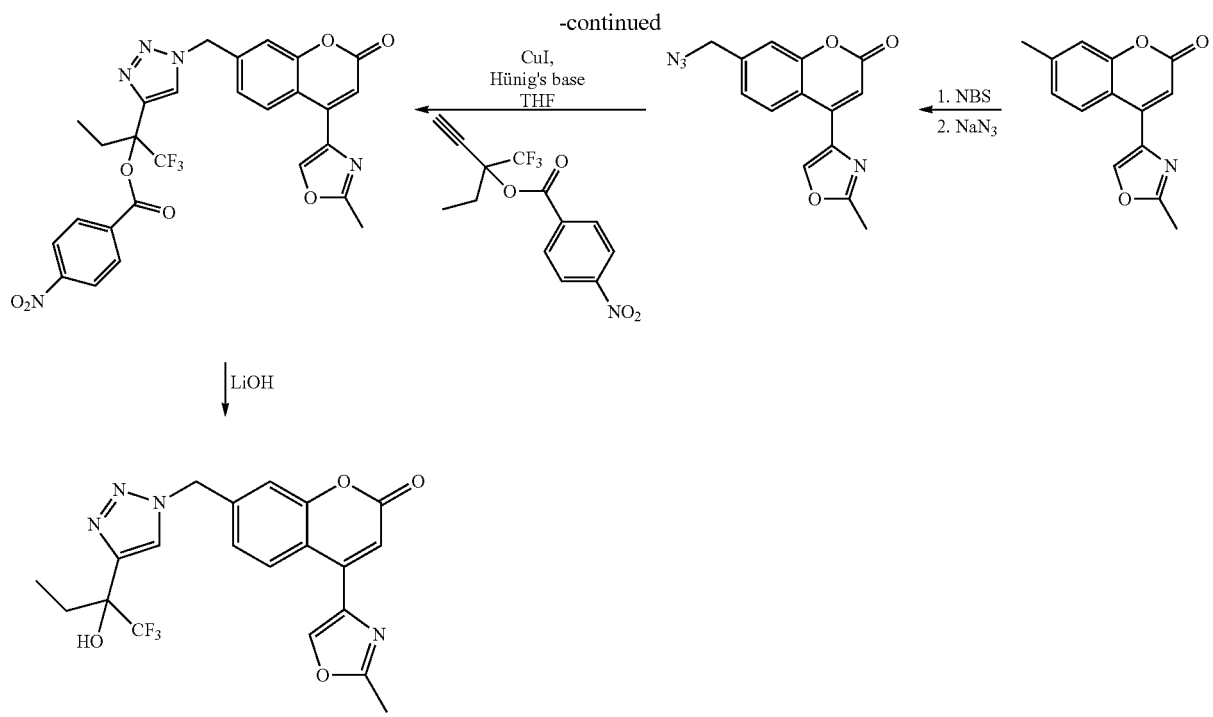

Coumarin Method E:

The bromocoumarin triflate (U.S. Pat. No. 5,552,437) can be reacted with tributyl (1-ethoxyvinyl)tin and a catalyst such as Pd(PPh$_3$)$_4$ under Stille coupling conditions to give the vinyl ether. Bromination can be achieved with a bromide source such as NBS. This bromoketone can be converted to a thiazole by treatment with thioacetamide in DMF at elevated temperature. This is followed by a one carbon homologation to the methyl ester, reduction of the ester to an alcohol, azide formation, and triazole formation as described above. Treatment of the ester with LiOH in THF gives the corresponding tertiary alcohol.

Coumarin Scheme E:

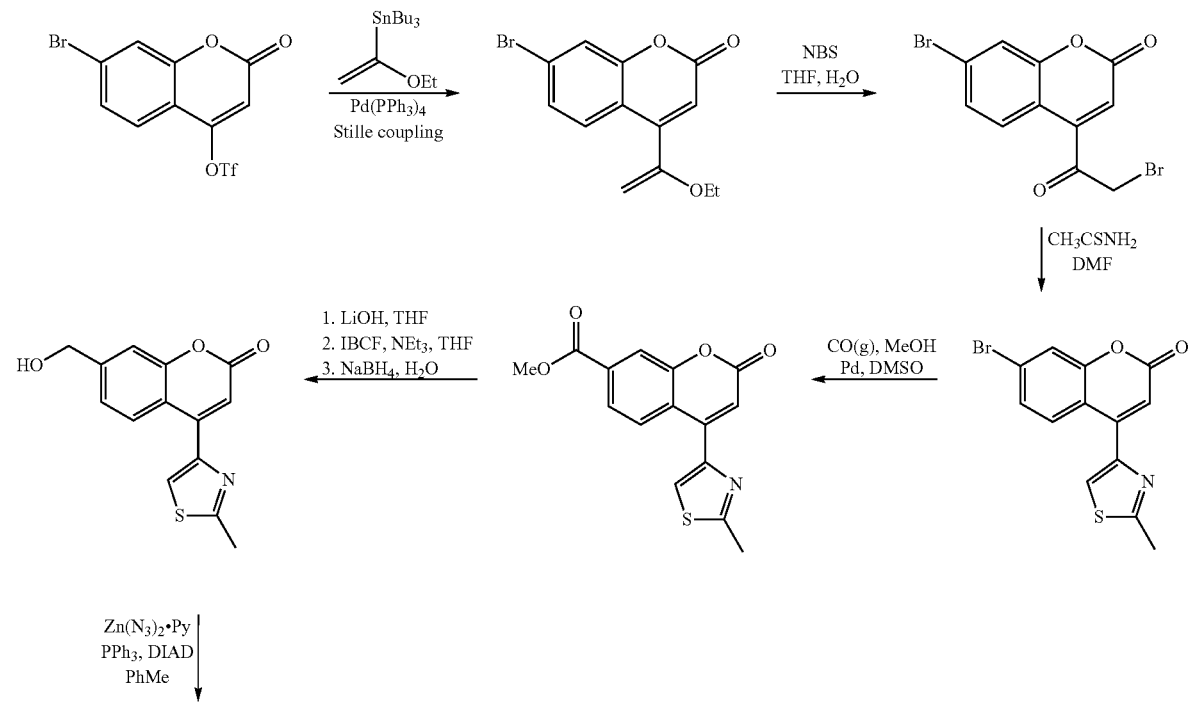

-continued

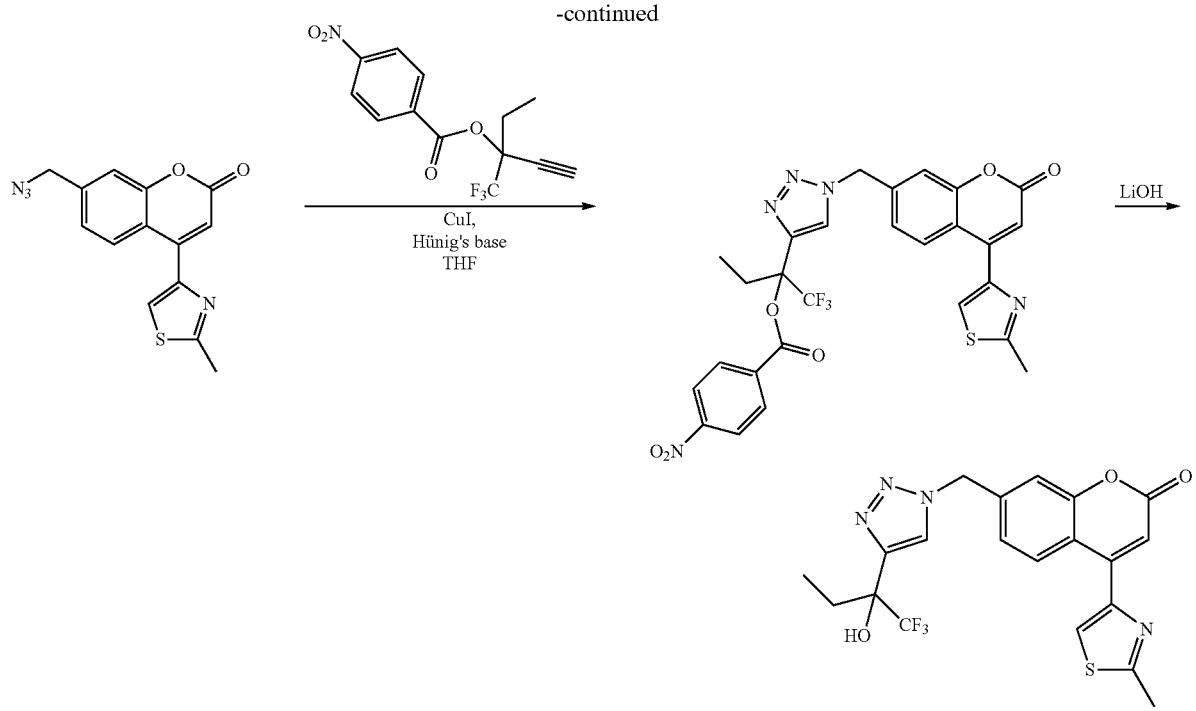

The following examples were prepared according to Coumarin Method A.

EXAMPLE 1

(S)-4-(3-fluorophenyl)-7-({4-[1-hydroxy-1-(trifluoromethyl)propyl]-1H-1,2,3-triazol-1-yl}methyl)-2H-chromen-2-one

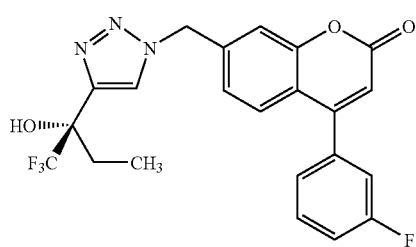

Step 1: 3-(trifluoromethyl)-1-(trimethylsilyl)pent-1-yn-3-ol

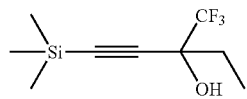

To a solution of trimethylsilylacetylene (6.0 g, 61.1 mmol) in THF (80 mL) cooled at −78° C., a 1.6M n-butyllithium in hexanes (38 mL, 61.1 mmol) was added dropwise. The solution was then stirred 1 hour, before a solution trifluoromethylethylketone (10 g, 79.4 mmol) in 25 mL of THF was added slowly. The reaction was stirred at −78° C. for 4 hours. The reaction was then poured into a saturated ammonium chloride solution and the aqueous layer was extracted (4×) with diethyl ether. The combined organic layers were washed with brine, dried over MgSO$_4$, filtered and concentrated under reduced pressure. The crude residue obtained was used as such for the next step. $^1$H NMR (400 MHz, acetone-d$_6$): 5.83 (s, 1H), 1.80 (q, 2H), 1.14 (t, 3H), 0.18 (s, 9H).

Step 2: 1-ethyl-1-(trifluoromethyl)prop-2-yn-1-yl 4-nitrobenzoate

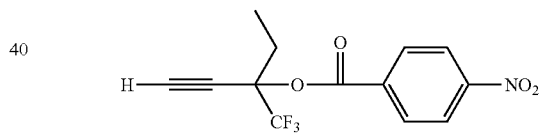

To a stirred solution of 3-(trifluoromethyl)-1-(trimethylsilyl)pent-1-yn-3-ol (10.5 g, 46.9 mmol) in DMF (140 mL), sodium hydride (60% in oil, 1.9 g, 46.9 mmol) was added portionwise. After 25 min stirring, a solution of 4-nitrobenzoyl chloride (8.7 g, 46.9 mmol) in 50 mL DMF was added slowly. The reaction mixture was then stirred at room temperature for 2 hours. The reaction mixture was quenched with pH 7 buffer 25% NH$_4$OAc aq solution (500 mL) and the product was extracted with diethyl ether (4×), washed with water (3×) and brine, dried over MgSO$_4$, filtered and concentrated. The crude residue obtained was purified by column chromatography (Ethyl acetate/hexanes, 15:85). $^1$H NMR (400 MHz, acetone-d$_6$): 8.45 (d, 2H), 8.27 (d, 2H), 3.69 (s, 1H), 2.60-2.40 (m, 2H), 1.16 (t, 3H).

The racemic material obtained was resolved by chiral HPLC (OD Chiralcel 2.5×50 cm column, solvent system: 2% i-PrOH/Hexanes, flow rate: 40 mL/min, 280 nm detection).

First enantiomer retention time: 10.06 min. $^1$H NMR (400 MHz, acetone-d$_6$): 8.45 (d, 2H), 8.27 (d, 2H), 3.69 (s, 1H), 2.60-2.40 (m, 2H), 1.16 (t, 3H).

Second enantiomer retention time 15.1 min. $^1$H NMR (400 MHz, acetone-d$_6$): 8.45 (d, 2H), 8.27 (d, 2H), 3.69 (s, 1H), 2.60-2.40 (m, 2H), 1.16 (t, 3H).

Step 3: 4-hydroxy-7-methyl-2H-chromen-2-one

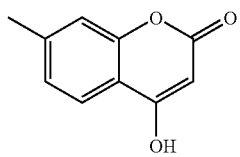

To a mechanically stirred suspension of sodium hydride (60% in oil, 30 g, 749 mmol) in toluene (400 mL), heated at 80° C., a solution of the commercially available 2'-hydroxy-4'-methylacetophenone (50 g, 0.333 mmol) in 150 mL of toluene was added dropwise over 1 h. After complete addition, the mixture was stirred 15 min and a solution of diethyl carbonate (81 mL, 666 mmol) in toluene (500 mL) was added dropwise over 1 h. The reaction mixture was then stirred overnight at reflux. After cooling, the reaction mixture was poured into 800 mL of 2N HCl. The precipitate formed was collected by filtration, co-evaporated twice with toluene and dried under high vacuum at 55° C. $^1$H NMR (400 MHz, acetone-$d_6$): 11.1 (bs, 1H), 7.76 (d, 1H), 7.18 (d, 1H), 7.14 (s, 1H), 5.60 (s, 1H), 2.47 (s, 3H).

Step 4: 7-methyl-2-oxo-2H-chromen-4-yl trifluoromethanesulfonate

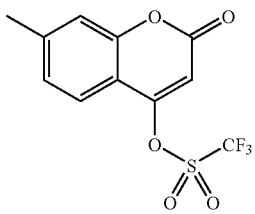

To a solution of 4-hydroxy-7-methyl-2H-chromen-2-one (32.5 g, 184 mmol) and triethylamine (44 ml, 313 mmol) in dichloromethane (750 mL) cooled at −30° C., a solution of triflic anhydride (49.7 mL, 294 mmol) in 200 mL of dichloromethane was added dropwise (internal temperature was kept below −30° C. during addition). The reaction was stirred 1 h at −30° C. and then slowly warmed to 0° C. The reaction was quenched with an aqueous saturated ammonium chloride solution. The isolated aqueous layer was extracted twice with dichloromethane. The combined organic layers were washed with brine, dried over MgSO$_4$, filtered and concentrated. The crude residue obtained was filtered trough a short column of silica gel eluting with dichloromethane to afford the title compound. $^1$H NMR (400 MHz, acetone-$d_6$): 7.68 (d, 1H), 7.38 (d, 1H), 7.32 (s, 1H), 6.60 (s, 1H), 2.52 (s, 3H).

Step 5: 4-(3-fluorophenyl)-7-methyl-2H-chromen-2-one

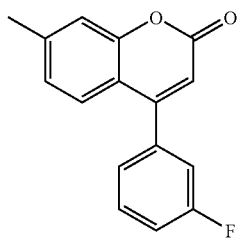

To a solution of 7-methyl-2-oxo-2H-chromen-4-yl trifluoromethanesulfonate (5 g, 16.2 mmol) and 3-fluorobenzeneboronic acid (2.5 g, 17.9 mmol) in THF (75 mL), tricyclohexylphosphine (227 mg, 0.81 mmol) and potassium fluoride (3.3 g, 56.8 mmol) were added. The reaction mixture was purged twice with nitrogen before palladium (II) acetate (146 mg, 0.65 mmol) was added. After 16 hours stirring at room temperature, the reaction mixture was filtered over celite and the filtrate was concentrated under reduced pressure. The crude residue obtained was purified by column chromatography (CH$_2$Cl$_2$/Hexanes, 70:30). To afford the title compound $^1$H NMR (400 MHz, acetone-$d_6$): 7.7-7.6 (m, 1H), 7.45-7.3 (m, 4H), 7.26 (s, 1H), 7.18 (d, 1H), 6.3 (s, 1H), 2.47 (s, 3H).

Step 6: 7-(bromomethyl)-4-(3-fluorophenyl)-2H-chromen-2-one

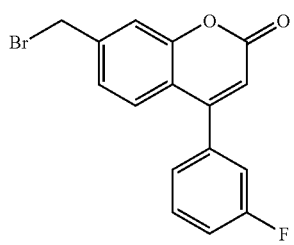

To a solution of 4-(3-fluorophenyl)-7-methyl-2H-chromen-2-one (1.25 g, 4.9 mmol) in carbontetrachloride (30 mL), N-bromosuccinimide (963 mg, 5.41 mmol) and benzoylperoxide (60 mg, 0.25 mmol) were added. The reaction was then stirred overnight at reflux. After cooling, the reaction mixture was concentrated under reduced pressure. The crude residue obtained was purified on a short column of silica gel (eluting with CH$_2$Cl$_2$). The filtrate was concentrated and the solid obtained was swished in a mixture of CH$_2$Cl$_2$/hexanes. The title product was collected by filtration. $^1$H NMR (400 MHz, acetone-$d_6$): 7.72-7.6 (m, 1H), 7.55 (s, 1H), 7.47 (s, 1H), 7.45-7.3 (m, 4H), 6.4 (s, 1H), 4.78 (s, 2H).

Step 7: 7-(azidomethyl)-4-(3-fluorophenyl)-2H-chromen-2-one

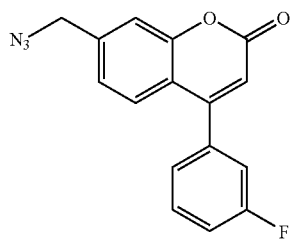

To a solution of 7-(bromomethyl)-4-(3-fluorophenyl)-2H-chromen-2-one (1.16 g, 3.5 mmol) in ethanol (35 mL), sodium azide (248 mg, 3.8 mmol) was added. The reaction mixture was then stirred overnight at reflux. After cooling, the reaction mixture was concentrated under reduced pressure and the crude residue was dissolved with CH$_2$Cl$_2$. Salts were removed by filtration and the filtrate was concentrated under reduced pressure to afford the tittle compound. $^1$H NMR (400 MHz, acetone-$d_6$): 7.72-7.6 (m, 1H), 7.65 (d, 1H), 7.47-7.32 (m, 5H), 6.42 (s, 1H), 4.67 (s, 2H).

Step 8: (S)-1-(1-{[4-(3-fluorophenyl)-2-oxo-2H-chromen-7-yl]methyl}-1H-1,2,3-triazol-4-yl)-1-(trifluoromethyl)propyl 4-nitrobenzoate To a solution of 7-(azidomethyl)-4-(3-fluorophenyl)-2H-chromen-2-one (30 mg, 0.1 mmol) and 1-ethyl-1-(trifluoromethyl)prop-2-yn-1-yl 4-nitrobenzoate (S-isomer, the second, slower eluting enantiomer from step 2) (27 mg, 0.1 mmol) in THF (5 mL) N,N-diisopropylethylamine (79 uL, 0.45 mmol) and copper iodide (26 mg, 0.14 mmol) were added. After overnight stirring, the reaction was diluted with ethyl acetate, filtered and washed with water and brine. The organic layer was then dried over $MgSO_4$, filtered and concentrated. The crude residue obtained was purified by column chromatography (acetone/$CH_2Cl_2$ 5:95) to afford the title compound. $^1H$ NMR (400 MHz, acetone-$d_6$): 8.5 (s, 1H), 8.42 (d, 2H), 8.31 (d, 2H), 7.7-7.6 (m, 1H), 7.51 (d, 1H), 7.4-7.25 (m, 5H), 6.42 (s, 1H), 5.89 (s, 2H), 3.1-2.98 (m, 1H), 2.91-2.8 (m, 1H), 1.14 (t, 3H).

Step 9: (S)-4-(3-fluorophenyl)-7-({4-[1-hydroxy-1-(trifluoromethyl)propyl]-1H-1,2,3-triazol-1-yl}methyl)-2H-chromen-2-one To a solution of (S)-1-(1-{[4-(3-fluorophenyl)-2-oxo-2H-chromen-7-yl]methyl}-1H-1,2,3-triazol-4-yl)-1-(trifluoromethyl)propyl 4-nitrobenzoate (15 mg, 0.025 mmol) in THF (2 mL), lithium hydroxide (0.125 mL of 1M solution, 0.125 mmol) was added. After 45 minutes stirring at room temperature, the reaction was quenched by the addition of 0.150 mL of a 2N HCl solution. The mixture was stirred 3 h at room temp and then heated 2 h at 40° C. After cooling, the reaction mixture was diluted with ethyl acetate, washed with brine, dried over $MgSO_4$, filtered and concentrated. The crude residue obtained was purified by column chromatography to afford the title compound. $^1H$ NMR (400 MHz, acetone-$d_6$): 8.21 (s, 1H), 7.7-7.6 (m, 1H), 7.53 (d, 1H), 7.42-7.3 (m, 5H), 6.41 (s, 1H), 5.87 (s, 2H), 5.48 (s, 1H), 2.4-2.3 (m, 1H), 2.1-2.0 (m, 1H), 0.87 (t, 3H).

EXAMPLE 1A

Alternate Method for the Preparation of (5)-4-(3-fluorophenyl)-7-({4-[1-hydroxy-1-(trifluoromethyl)propyl]-1H-1,2,3-triazol-1-yl}methyl)-2H-chromen-2-one Step 1. A 100 mL flask equipped with a mechanical stirrer, a thermocouple, a nitrogen inlet and a cooling bath was charged with trimethylsilyl acetylene (3.5 g, 1.50 eq) and MTBE (12.0 mL). The mixture was cooled to −67° C. and 2.26 M n-BuLi (11.2 mL, 1.05 eq) was added to the solution over 1 hr, keeping the reaction mixture below −50° C. The reaction mixture was aged 45 min before the addition of 1,1,1-trifluoro-2-butanone (3.3 mL, 1.00 eq) over a period of 1 hr (internal temperature was kept below −50° C.). The mixture was aged 20 min, then p-nitrobenzoyl chloride (4.7 g, 1.05 eq) was added over 1 hr as a THF solution (7.0 mL), keeping the reaction mixture below −30° C. The reaction mixture was allowed to warm to 5° C. over 3 hrs.

The reaction was quenched by careful addition of water (9.0 mL). To the reaction mixture was added Solka Floc (0.25 g, 8% wt) and the mixture was stirred 20 min. The biphasic mixture was filtered over Solka Floc, then transferred to a separatory funnel where the layers were separated. The organic layer was washed with ½ saturated solution of $NaHCO_3$ (2×15.0 mL) and with brine (15.0 mL) to provide 1-ethyl-1-trifluoromethyl-3-trimethylsilylprop-2-yn-1-yl 4-nitrobenzoate (TMS-acetylene ester).

Step 2. A 100 mL flask was charged with the TMS-acetylene ester from Step 1 (2.2 g, 1.00 eq) and DMF (4 mL/g). The mixture was cooled to 0° C. and $K_3PO_4$ (1.5 g, 1.2 eq) was added to the solution, followed by a slow addition of water (0.23 mL, 2.2 eq) over 1 hr. The mixture was aged 30 min at 0° C. then poured into a pre-cooled (2° C.) mixture of MTBE (3 mL/g) and 3N HCl (3.5 mL/g). The mixture was filtered over Solka Floc, rinse with 1 mL/g MTBE and transferred to a separatory funnel. The layers were separated and the organic layer was washed with water (2×4 mL/g), ½ saturated solution of $NaHCO_3$ (1×4 mL/g) and brine (1×4 mL/g), and concentrated to provide 1-ethyl-1-trifluoromethylprop-2-yn-1-yl 4-nitrobenzoate (H-acetylene ester).

Step 3. A 100 mL flask was charged with the H-acetylene ester of Step 2 (7.1 g, 1.00 eq) and heptane (4.5 mL/g). The mixture was heated to 65° C. to dissolve the H-acetylene ester. The solution was cooled to 0° C. over a period of 15 hrs to allow a slow crystallization of the H-acetylene ester. When the temperature reached 56° C. seeds were added. The crystallized H-acetylene ester was filtered and rinsed 2×1.0 mL/g of cold heptane, then dried on the frit for 22 hr under a flow of nitrogen.

The racemic material obtained was resolved by chiral HPLC (11×25 cm DAC column packed with Chiralpak OD). The feed was about 29 mg/mL in v/v 13/87 isopropyl alcohol/heptane, and the injection volume ranged from 1.0 to 1.2 liters with elution performed using 15% v/v isopropyl alcohol/heptane at a flow rate of 800 mL/min.; UV detection at 295 nm. The second eluting enantiomer (S-isomer) was used in the later step.

Step 4. Flask A—To a stirred thick slurry of 3-fluorobenzoic acid (1.2 g) in $CH_3CN$ (6 mL) was added CDI (2.6 g) portion-wise. The resulting hazy solution was stirred for 4 hours (temperature of the batch was raised to 22° C.).

Flask B—To a 100 mL round bottom flask was charged potassium ethyl malonate (3.17 g) and $CH_3CN$ (30 mL). $MgCl_2$ was then added (1.47 g) in portions over 15 min. The mixture was stirred at 35° C. for 30 min. and then cooled to 25° C. Triethylamine (TEA) (6 mL) was added slowly and the slurry was stirred for 30 min. The solution in flask A was then transferred to the slurry in flask B over 5 min. The reaction mixture was stirred for 1.5 hr, cooled to 7° C. and then quenched with 3 N HCl (32 mL), (internal temperature kept <20° C.). The resulting two phase solution was concentrated, and the resulting concentrate extracted with MTBE. The organic phase was collected and washed with water, 5% $NaHCO_3$ and finally 20% NaCl. The organic layer was then concentrated under reduced pressure to give ethyl 3-fluoro-β-oxobenzenepropanoate (keto ester) as an orange colored oil (2.921 g) in 97% yield.

Step 5. To a 50 mL flask was added methanesulfonic acid (16 mL) followed by m-cresol (2.35 g). To this stirred solution was added the keto ester of Step 4 (4.854 g) over 30 minutes. The mixture was stirred for 3 hours and then heated at 40-45° C. for 2 hours. Then heating was stopped and the reaction mixture was allowed to stir overnight. The reaction mixture was partitioned between $CH_2Cl_2$ and water. The aqueous layer was back extracted with $CH_2Cl_2$ and the organic layers combined. The organic phase was washed with 1 N NaOH and water. The residual oil was concentrated and recrystallized in isopropyl alcohol to give 4-(3-fluorophenyl)-7-methyl-2H-chromen-2-one (methylcoumarin) (4.050 g) in 73% isolated yield.

Step 6. To a stirred suspension of the methylcoumarin from Step 5 (4.1 g) in $CH_3CN$ (10.0 mL) was added NBS (3.3 g, 1.15 eq.) followed by benzoyl peroxide (0.19 g, 5 mol %)

and the mixture heated to reflux for 2 hours, then heating was turned off and the reaction mixture was stirred overnight. The crystallized product was then isolated by filtration and the filter cake washed with isopropyl alcohol and finally dried under a flow of nitrogen to give 7-bromomethyl-4-(3-fluorophenyl)-2H-chromen-2-one (bromomethylcoumarin) (3.213 g with 2 mol % starting material by H/F NMR) in 60% yield.

Step 7. To a stirred suspension of the bromomethylcoumarin from Step 6 (3.2 g) in ethanol (32 mL) was added $NaN_3$ (0.65 g). The mixture was heated at 60° C. for 3 hours after which time the heating was stopped and the reaction mixture was cooled to 10-15° C. Water (30 mL) was added and the reaction mixture was stirred for 1 hour. The product was isolated by filtration and the filter cake was washed with water (2×10 mL). The product was dried under a flow of nitrogen overnight and then transferred into a vacuum oven (40° C., nitrogen sweep, 4 hr) to give 7-azido-methyl-4-(3-fluorophenyl)-2H-chromen-2-one (azidomethylcoumarin) (2.6 g) in 93% isolated assay yield.

Step 8. A visually clean and dry 50 mL flask was fitted with an internal temperature probe, nitrogen inlet and outlet and a reflux condenser. The flask was charged with THF (25 mL), the azidomethylcoumarin from Step 7 (5 g, 1 eq.), the H-acetylene ester from Step 3 (the S-isomer, second eluting isomer from chiral separation, 5.4 g, 1.1 eq.), diisopropylethylamine (5.7 mL, 2 eq.) and degassed by bubbling $N_2$ for 20 min. To this solution was added CuI (63 mg, 2 mol %, milled with a mortar and pestle) in one portion and the reaction mixture was degassed for an additional 5 min. then heated up to 30° C. and stirred for 24 h. This reaction mixture was cooled to −10° C. and 4N LiOH (15 mL) was added. After 4 h at rt HPLC analysis indicated hydrolysis to be complete. To this reaction mixture at 0° C. was added 6N HCl (15 mL) and the reaction was stirred vigorously at rt for 18 hr. MTBE and water were added to this beige slurry and the layers were separated. The organic layer was washed with $Na_2CO_3$ (3×) followed by two washes with a solution of ½ brine. The crude product was recrystallized from hot ethanol to give the product as a light beige solid in 70% yield.

Three polymorphic forms (Forms A, B and C), as well as amorphous form of the compound of Example 1 have been identified. FIG. 1 shows the X-ray powder diffraction pattern (XRPD) for Form A having characteristic diffraction peaks corresponding to d-spacings of 4.55, 4.79, 6.46, 6.79, 13.57 Å. FIG. 2 shows the XRPD pattern for Form B having characteristic diffraction peaks corresponding to d-spacings of 2.53, 3.55, 4.03, 7.60, 11.97 Å. FIG. 3 shows the XRPD pattern for Form C having characteristic diffraction peaks corresponding to d-spacings of 2.57, 3.21, 4.05, 6.44, 12.88 Å. FIG. 4 shows the XRPD pattern for the amorphous form having broad amorphous peak centered around 3.4 Å.

XRPD patterns were measured using a Scintag XDS-2000, Si(Li) Peltier-cooled solid state detector, CuKα source using a generator power of 45 kV and current of 40 mA. A divergent beam of 2 mm and 4 mm and receiving beam slits of 0.5 mm and 0.2 mm were used. Scan range was set from 2-40° 2θ in step mode using a step size of 0.020 and a 2 second count time per step. The sample was measured on a quartz disk. Peak positions were verified using a standard corundum plate (NIST SRM 1976).

Differential scanning calorimeter (DSC) data were acquired using TA Instruments DSC (Q1000) or equivalent instrumentation. Between 1 and 6 mg sample is weighed into an open pan. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 200° C. The heating program is started. When the run is completed, the data are analyzed using the DSC analysis program contained in the system software. The melting endotherm is integrated between baseline temperature points that are above and below the temperature range over which the endotherm is observed. The data reported are the onset temperature, peak temperature and enthalpy. The glass transition temperature (Tg) was integrated above and below the temperature range which baseline shifted is observed on reversible heat flow curve. The data reported is the midpoint temperature.

| Thermal Properties of Compound of Example 1, Forms A, B & C | | | |
|---|---|---|---|
| Sample | $T_o$ (° C.) | $T_{pk}$ (° C.) | ΔH (kJ/mol) |
| Form A | 146.6 ± 0.1 | 153.2 ± 0.1 | 35.3 ± 0.9 |
| Form B | 142.1 ± 0.7 | 144.0 ± 0.3 | 41.0 ± 0.2 |
| Form C | 148.7 ± 0.0 | 150.8 ± 0.0 | 46.7 ± 0.5 |

Thermal Properties of Amorphous Form:

A glass transition temperature of 52.3° C. (midpoint) with an associated heat capacity change of 0.46 J/gC.

Using the procedures given in example 1, the following Examples 2-11 were prepared using the appropriate boronic acid. Examples 2, 3, 4, 5, 6, 7 and 8 were prepared with enantiopure 1-ethyl-1-(trifluoromethyl)prop-2-yn-1-yl 4-nitrobenzoate (second eluting enantiomer described in Example 1, Step 2). Examples 2A, 5A, 9, 10 and 11 were prepared with racemic 1-ethyl-1-(trifluoromethyl)prop-2-yn-1-yl 4-nitrobenzoate. Any of the compounds herein could be prepared with racemic or enantiopure 1-ethyl-1-(trifluoromethyl)prop-2-yn-1-yl 4-nitrobenzoate.

EXAMPLE 2

(S)-4-(4-Fluorophenyl)-7-[4-(1-hydroxy-1-trifluoromethyl-propyl)-[1,2,3]triazol-1-ylmethyl]-chromen-2-one

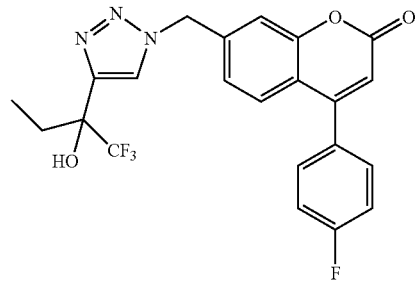

$^1$H NMR (400 MHz, acetone-$d_6$): 8.21 (s, 1H), 7.7-7.6 (m, 1H), 7.53 (d, 1H), 7.42-7.35 (m, 3H), 7.31 (d, 1H), 6.4 (s, 1H), 5.85 (s, 2H), 5.47 (s, 1H), 2.41-2.3 (m, 1H), 2.15-2.05 (m, 1H), 0.86 (t, 3H).

EXAMPLE 2A 4-(4-Fluoro-phenyl)-7-[4-(1-hydroxy-1-trifluoromethyl-propyl)-[1,2,3]triazol-1-ylmethyl]-chromen-2-one was prepared using the same procedure as for Example 2, but using racemic 1-ethyl-1-(trifluoromethyl)prop-2-yn-1-yl 4-nitrobenzoate instead of enantiopure material.

EXAMPLE 3

(S)-4-(2-Fluoro-phenyl)-7-[4-(1-hydroxy-1-trifluoromethyl-propyl)-[1,2,3]triazol-1-ylmethyl]-chromen-2-one

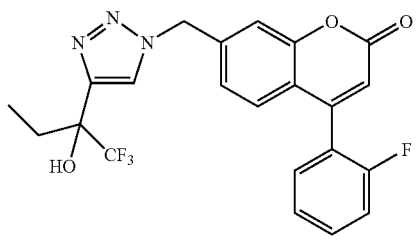

$^1$H NMR (400 MHz, acetone-$d_6$): 8.2 (s, 1H), 7.7-7.6 (m, 1H), 7.6-7.5 (m, 1H), 7.46-7.25 (m, 5H), 6.45 (s, 1H), 5.84 (s, 2H), 5.47, (s, 1H), 2.4-2.28 (m, 1H), 2.12-2.0 (m, 1H), 0.85 (t, 3H).

EXAMPLE 4

(S)-4-(3,5-Difluoro-phenyl)-7-[4-(1-hydroxy-1-trifluoromethyl-propyl)-[1,2,3]triazol-1-ylmethyl]-chromen-2-one

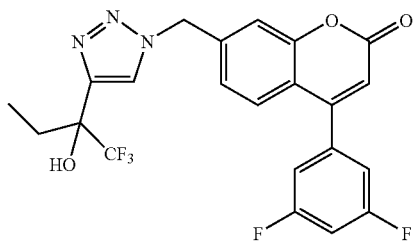

$^1$H NMR (400 MHz, acetone-$d_6$): 8.2 (s, 1H), 7.55 (d, 1H), 7.41 (d, 1H), 7.35-7.24 (m, 4H), 6.45 (s, 1H), 5.85 (s, 2H), 5.49 (s, 1H), 2.4-2.3 (m, 1H), 2.15-2.05 (m, 1H), 0.85 (t, 3H).

EXAMPLE 5

(S)-7-[4-(1-Hydroxy-1-trifluoromethyl-propyl)-[1,2,3]triazol-1-ylmethyl]-4-phenyl-chromen-2-one

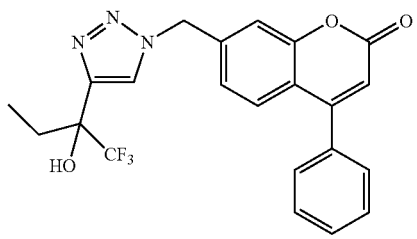

$^1$H NMR (400 MHz, acetone-$d_6$): 8.21 (s, 1H), 7.65-7.55 (m, 5H), 7.53 (d, 1H), 7.4 (s, 1H), 7.3 (d, 1H), 6.38 (s, 1H), 5.84 (s, 2H), 5.49 (s, 1H), 2.4-2.3 (m, 1H), 2.1-2.0 (m, 1H), 0.85 (t, 3H).

EXAMPLE 5A

7-[4-(1-Hydroxy-1-trifluoromethyl-propyl)-[1,2,3]triazol-1-ylmethyl]-4-phenyl-chromen-2-one was prepared using the same procedure as for Example 5, but using racemic 1-ethyl-1-(trifluoromethyl)prop-2-yn-1-yl 4-nitrobenzoate instead of enantiopure material.

EXAMPLE 6

(S)-4-(3-Chlorophenyl)-7-[4-(1-hydroxy-1-trifluoromethyl-propyl)-[1,2,3]triazol-1-ylmethyl]-chromen-2-one

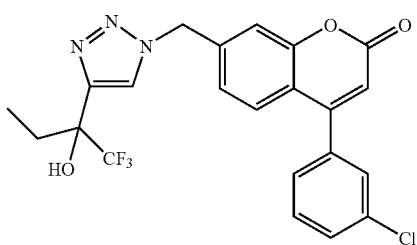

$^1$H NMR (400 MHz, acetone-$d_6$): 8.2 (s, 1H), 7.65-7.6 (m, 3H), 7.55-7.47 (m, 2H), 7.4 (s, 1H), 7.3 (d, 1H), 6.41 (s, 1H), 5.85 (s, 2H), 5.48 (s, 1H), 2.4-2.3 (m, 1H), 2.1-2.0 (m, 1H), 0.85 (t, 3H).

EXAMPLE 7

(S)-4-(4-Chlorophenyl)-7-[4-(1-hydroxy-1-trifluoromethyl-propyl)-[1,2,3]triazol-1-ylmethyl]-chromen-2-one

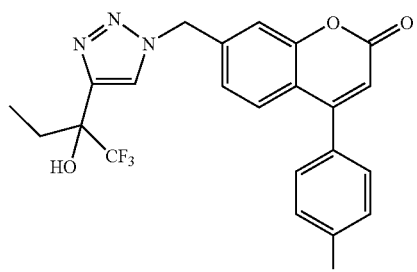

$^1$H NMR (400 MHz, acetone-$d_6$): 8.2 (s, 1H), 7.65 (d, 2H), 7.62 (d, 2H), 7.51 (d, 1H), 7.4 (s, 1H), 7.3 (d, 1H), 6.4 (s, 1H), 5.85 (s, 2H), 5.48 (s, 1H), 2.4-2.3 (m, 1H), 2.1-2.0 (m, 1H), 0.85 (t, 3H).

EXAMPLE 8

(S)-7-[4-(1-Hydroxy-1-trifluoromethyl-propyl)-[1,2,3]triazol-1-ylmethyl]-4-thiophen-3-yl-chromen-2-one

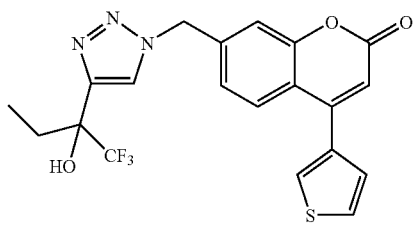

$^1$H NMR (400 MHz, acetone-d$_6$): 8.22 (s, 1H), 7.95 (s, 1H), 7.81-7.74 (m, 2H), 7.45 (d, 1H), 7.4 (s, 1H), 7.32 (s, 1H), 6.45 (s, 1H), 5.85 (s, 2H), 5.47 (s, 1H), 2.4-2.3 (m, 1H), 2.1-2.0 (m, 1H), 0.85 (t, 3H).

EXAMPLE 9

4-(3-Ethoxy-phenyl)-7-[4-(1-hydroxy-1-trifluoromethyl-propyl)-[1,2,3]triazol-1-ylmethyl]-chromen-2-one

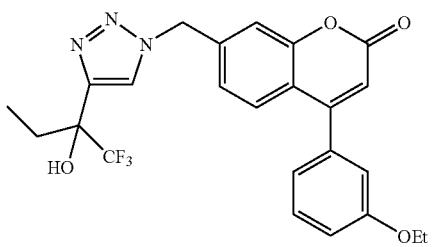

$^1$H NMR (400 MHz, acetone-d$_6$): 8.22 (s, 1H), 7.56 (d, 1H), 7.5 (t, 1H), 7.4 (s, 1H), 7.3 (d, 1H), 7.15-7.05 m, 3H), 6.37 (s, 1H), 5.85 (s, 2H), 5.47 (s, 1H), 4.14 (q, 2H), 2.4-2.3 (m, 1H), 2.1-2.0 (m, 1H), 1.38 (t, 3H), 0.87 (t, 3H).

EXAMPLE 10

7-[4-(1-Hydroxy-1-trifluoromethyl-propyl)-[1,2,3]triazol-1-ylmethyl]-4-(3-trifluoromethoxy-phenyl)-chromen-2-one

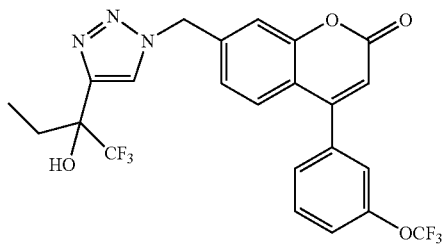

$^1$H NMR (400 MHz, acetone-d$_6$): 8.22 (s, 1H), 7.77 (t, 1H), 7.64 (d, 1H), 7.57-7.53 (m, 1H), 7.5 (d, 1H), 7.42 (s, 1H), 7.3 (d, 1H), 6.47 (s, 1H), 5.85 (s, 2H), 5.47 (s, 1H), 2.4-2.3 (m, 1H), 2.1-2.0 (m, 1H), 0.85 (t, 3H).

EXAMPLE 11

7-[4-(1-Hydroxy-1-trifluoromethyl-propyl)-[1,2,3]triazol-1-ylmethyl]-4-(3-methoxy-phenyl)-chromen-2-one

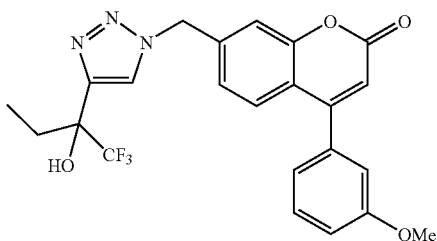

$^1$H NMR (400 MHz, acetone-d$_6$): 8.21 (s, 1H), 7.68 (d, 1H), 7.5 (t, 1H), 7.4 (s, 1H), 7.3 (d, 1H), 7.2-7.05 (m, 3H), 6.38 (s, 1H), 5.82 (s, 2H), 5.48 (s, 1H), 3.9 (s, 3H), 2.4-2.3 (m, 1H), 2.1-2.0 (m, 1H), 0.85 (t, 3H).

EXAMPLE 12

7-[4-(1-Ethyl-1-hydroxy-propyl)-[1,2,3]triazol-1-ylmethyl]-4-(3-fluoro-phenyl)-chromen-2-one

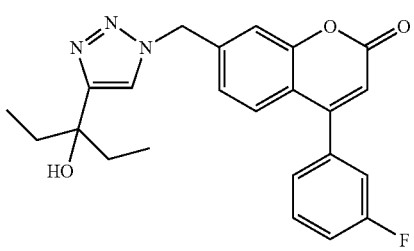

To a solution of 7-(azidomethyl)-4-(3-fluorophenyl)-2H-chromen-2-one (343 mg, 0.78 mmol) and 3-ethyl-1-pentyn-3-ol (80 mg, 0.71 mmol) in THF (7 mL) N,N-diisopropylethylamine (622 uL, 3.6 mmol) and copper iodide (204 mg, 1.07 mmol) were added. After overnight stirring, the reaction was diluted with ethyl acetate, filtered and washed with water and brine. The organic layer was then dried over MgSO$_4$, filtered and concentrated. The crude residue obtained was purified by column chromatography (acetone/CH$_2$Cl$_2$ 10:90) to afford the title compound. $^1$H NMR (400 MHz, acetone-d$_6$): 7.89 (s, 1H), 7.7-7.6 (m, 1H), 7.53 (d, 1H), 7.45-7.32 (m, 4H), 7.27 (d, 1H), 6.42 (s, 1H), 5.79 (s, 2H), 3.78 (s, 1H), 2.0-1.74 (m, 4H), 0.78 (t, 6H).

Using the procedures given in examples 1 and 12 above, the following additional examples 13-18 were prepared using the appropriate boronic acid and ethynyl derivative.

EXAMPLE 13

7-[4-(1-Ethyl-1-hydroxy-propyl)-[1,2,3]triazol-1-ylmethyl]-4-(3-methoxy-phenyl)-chromen-2-one

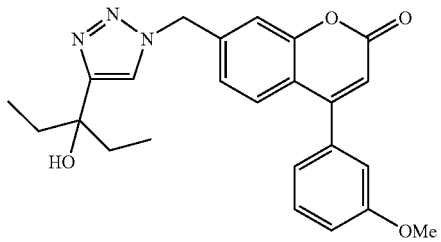

$^1$H NMR (400 MHz, acetone-$d_6$): 7.92 (s, 1H), 7.56 (d, 1H), 7.5 (t, 1H), 7.34 (d, 1H), 7.27-7.20 (m, 1H), 7.15-7.05 (m, 3H), 6.37 (s, 1H), 5.78 (s, 2H), 3.9 (s, 3H), 3.80 (s, 1H), 1.95-1.75 (m, 4H), 0.78 (t, 6H).

EXAMPLE 14

7-[4-(1-Ethyl-1-hydroxy-propyl)-[1,2,3]triazol-1-ylmethyl]-4-(4-methoxy-phenyl)-chromen-2-one

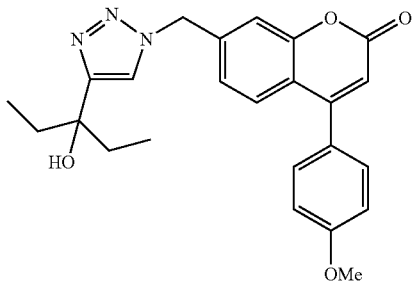

$^1$H NMR (400 MHz, acetone-$d_6$): 7.92 (s, 1H), 7.60 (d, 1H), 7.53 (d, 2H), 7.34 (s, 1H), 7.25 (d, 1H), 7.15 (d, 2H), 6.33 (s, 1H), 5.78 (s, 2H), 3.94 (s, 3H), 3.78 (s, 1H), 1.95-1.75 (m, 4H), 0.78 (t, 6H).

EXAMPLE 15

7-[4-(1-Ethyl-1-hydroxy-propyl)-[1,2,3]triazol-1-ylmethyl]-4-phenyl-chromen-2-one

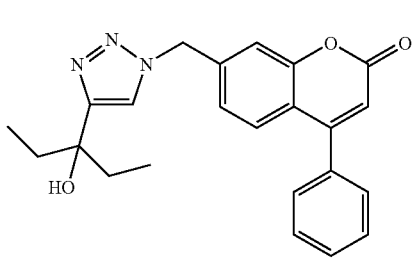

$^1$H NMR (400 MHz, acetone-$d_6$): 7.91 (s, 1H), 7.64-7.54 (m, 5H), 7.51 (d, 1H), 7.34 (s, 1H), 7.26 (d, 1H), 6.38 (s, 1H), 5.79 (s, 2H), 3.8 (s, 1H), 1.95-1.75 (m, 4H), 0.78 (t, 6H).

EXAMPLE 16

7-[4-(1-Ethyl-1-hydroxy-propyl)-[1,2,3]triazol-1-ylmethyl]-4-(4-fluoro-phenyl)-chromen-2-one

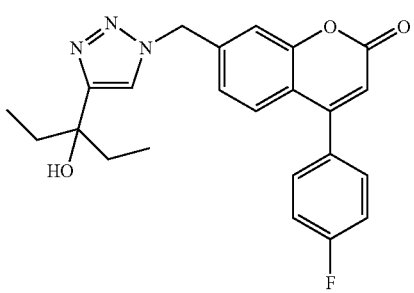

$^1$H NMR (400 MHz, acetone-$d_6$): 7.9 (s, 1H), 7.7-7.6 (m, 2H), 7.53 (d, 1H), 7.4-7.32 (m, 3H), 7.25 (d, 1H), 6.37 (s, 1H), 5.80 (s, 2H), 3.80 (s, 1H), 1.95-1.75 (m, 4H), 0.78 (t, 6H).

EXAMPLE 17

4-(4-Fluoro-phenyl)-7-[4-(tetrahydro-pyran-2-yloxymethyl)-[1,2,3]triazol-1-ylmethyl]-chromen-2-one

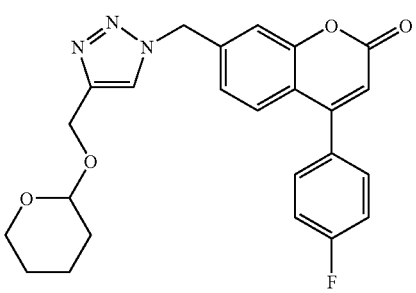

$^1$H NMR (400 MHz, acetone-$d_6$): 8.09 (s, 1H), 7.7-7.6 (m, 2H), 7.52 (d, 1H), 7.45-7.35 (m, 3H), 7.3 (d, 1H), 6.38 (s, 1H), 5.80 (s, 2H), 4.76 (t, 2H), 4.57 (d, 1H), 3.9-3.8 (m, 1H), 3.54-3.44 (m, 1H), 1.82-1.58 (m, 2H), 1.58-1.4 (m, 4H).

EXAMPLE 18

4-(4-Fluoro-phenyl)-7-[4-(1-hydroxy-1-phenyl-ethyl)-[1,2,3]triazol-1-ylmethyl]-chromen-2-one

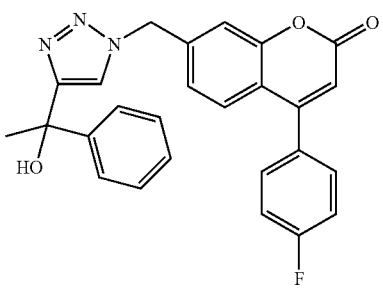

$^1$H NMR (400 MHz, acetone-d$_6$): 7.92 (s, 1H), 7.64-7.54 (m, 4H), 7.5 (d, 1H), 7.4-7.24 (m, 6H), 7.18 (t, 1H), 6.37 (s, 1H), 5.84 (s, 2H), 1.95 (s, 3H).

EXAMPLE 19

4-(4-Fluoro-phenyl)-7-[4-(4-hydroxy-tetrahydropyran-4-yl)-[1,2,3]triazol-1-ylmethyl]-chromen-2-one

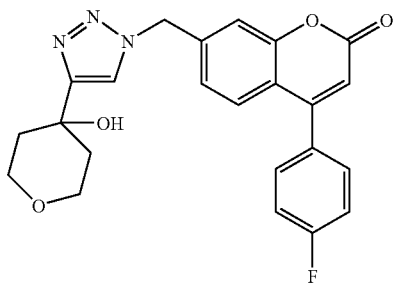

Step 1: 4-{(trimethylsilyl)ethynyl}tetrahydropyran-4-ol

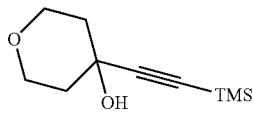

To a solution of trimethylsilylacetylene (5 mL, 35.4 mmol) in THF (100 mL) cooled at −78° C., a 1.6M n-butyllithium in hexanes (22.1 mL, 35.4 mmol) was added dropwise. The solution was stirred for 30 min before tetrahydro-4H-pyran-4-one (3.47 mL, 37.2 mmol) was added. The temperature was slowly raised to room temperature and the reaction was stirred overnight. The reaction was quenched with a saturated ammonium chloride solution and the aqueous layer was extracted with ethyl acetate (3×). The combined organic layers were washed with brine, dried over MgSO$_4$, filtered and concentrated under reduced pressure. The crude residue obtained was used as such for the next step. $^1$H NMR (400 MHz, acetone-d$_6$): 4.60 (s, 1H), 3.85-3.75 (m, 2H), 3.61-3.51 (m, 2H), 1.98-1.87 (m, 2H), 1.74-1.66 (m, 2H), 0.16 (s, 9H).

Step 2: 4-ethynyltetrahydropyran-4-ol

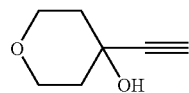

To a solution of 4-{(trimethylsilyl)ethynyl}tetrahydropyran-4-ol (1.0 g, 5.04 mmol) in THF (SnL), a 1 M solution of tetrabutyl ammonium fluoride in THF (5.29 mL, 5.29 mmol) was added and the reaction was stirred 2 hours at room temperature. The reaction mixture was then poured into an aqueous 5% NH$_4$OAc solution and diluted with ethyl acetate. The isolated organic layer was washed with brine, dried over MgSO$_4$, filtered and concentrated. The crude residue obtained was used as such for the next step. $^1$H NMR (400 MHz, acetone-d$_6$): 4.61 (s, 1H), 3.87-3.77 (m, 2H), 3.60-3.50 (m, 2H), 2.98 (s, 1H), 1.89-1.81 (m, 2H), 1.77-1.65 (m, 2H).

Step 3: Using 4-ethynyltetrahydropyran-4-ol and 7-(azidomethyl)-4-(4-fluorophenyl)-2H-chromen-2-one and following the general procedure described in example 1, the title compound was prepared. $^1$H NMR (400 MHz, acetone-d$_6$): 8.04 (s, 1H), 7.7-7.6 (m, 2H), 7.5 (d, 1H), 7.42-7.32 (m, 3H), 7.3 (d, 1H), 6.4 (s, 1H), 5.78 (s, 2H), 3.37 (s, 1H), 3.9-3.8 (m, 2H), 3.7-3.6 (m, 2H), 2.25-2.15 (m, 2H), 1.8-1.7 (m, 2H).

EXAMPLE 20

4-(4-Fluoro-phenyl)-7-[4-(4-methoxy-tetrahydropyran-4-yl)-[1,2,3]triazol-1-ylmethyl]-chromen-2-one

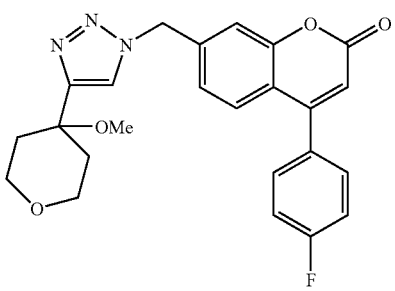

Step 1: [(4-methoxy-4-tetrahydropyranyl)ethynyl](trimethyl)silane

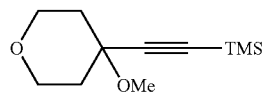

To a cooled solution (0° C.) of 4-{(trimethylsilyl)ethynyl}tetrahydropyran-4-ol prepared as described in the above example (2.5 g, 12.6 mmol) in a THF-DMF mixture (55 mL, 10:1), sodium hydride (60% suspension in oil, 0.504 g, 12.6 mmol) was added portionwise. After addition, the mixture was stirred 15 minutes before iodomethane (0.788 mL, 12.6 mmol) was added. The temperature was slowly raised to room temperature and the reaction was stirred for another 2 hours. The reaction mixture was then quenched with water and the product was extracted with ethyl acetate (2×). The combined organic layers were diluted with hexanes and washed with water and brine, dried over MgSO$_4$, filtered and concentrated. The crude residue obtained was purified by column chromatography (acetone/dichloromethane, 2:98) to afford the title compound. $^1$H NMR (400 MHz, acetone-d$_6$): 3.82-3.74 (m, 2H), 3.61-3.54 (m, 2H), 3.34 (s, 3H), 1.90-1.82 (m, 2H), 1.71-1.63 (m, 2H), 0.21 (s, 9H).

Step 2: 4-ethynyl-4-methoxytetrahydropyran

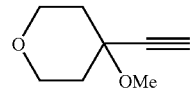

To a solution of [(4-methoxy-4-tetrahydropyranyl)ethynyl](trimethyl)silane (2.25 g, 10.6 mmol) in THF (20 mL), a 1 M solution of tetrabutyl ammonium fluoride in THF (11.12 mL, 11.12 mmol) was added and the reaction was stirred 1 hour at room temperature. The reaction mixture was then poured into an aqueous 5% NH$_4$OAc solution and diluted with ethyl acetate. The isolated organic layer was washed with brine, dried over MgSO$_4$, filtered and concentrated. The crude residue obtained was used as such for the next step. $^1$H NMR (400 MHz, acetone-d$_6$): 3.85-3.75 (m, 2H), 3.62-3.52 (m, 2H), 3.35 (s, 3H), 3.14 (s, 1H), 1.93-1.86 (m, 2H), 1.75-1.65 (m, 2H).

Step 3: Using the general procedure described in example 1, the title compound was prepared. $^1$H NMR (400 MHz, acetone-d$_6$): 8.15 (s, 1H), 7.7-7.6 (m, 2H), 7.53 (d, 1H), 7.42-7.32 (m, 3H), 7.27 (d, 1H), 6.4 (s, 1H), 5.72 (s, 2H), 3.8-3.7 (m, 2H), 3.6-3.5 (m, 2H), 3.03 (s, 3H), 2.2-2.0 (m, 4H).

Using the general procedures described in Example 1, the following Examples 21-23 were prepared using 7-(azidomethyl)-4-(3-fluorophenyl)-2H-chromen-2-one and the appropriate ethynyl starting material, i.e., TMS—C≡C—Ph, TMS—C≡C-benzyl, or TMS—C≡C-(2-pyridyl).

EXAMPLE 21

4-(3-fluorophenyl)-7-[(4-phenyl-1H-1,2,3-triazol-1-yl)methyl]-2H-chromen-2-one

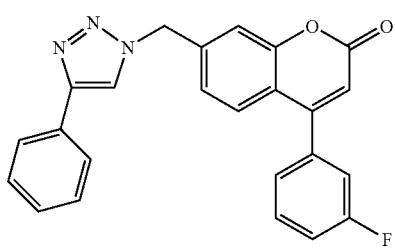

$^1$H NMR (400 MHz, acetone-d$_6$): 8.50 (1H, s), 7.90 (2H, d), 7.65 (1H, m), 7.55 (1H, d), 7.50 (1H, s), 7.50-7.30 (7H, m), 6.45 (1H, s), 5.90 (2H, s).

EXAMPLE 22

7-[(4-benzyl-1H-1,2,3-triazol-1-yl)methyl]-4-(3-fluorophenyl)-2H-chromen-2-one

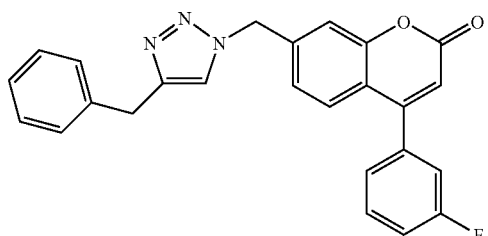

$^1$H NMR (400 MHz, acetone-d$_6$): 7.80 (1H, s), 7.68-7.62 (1H, m), 7.50 (1H, d, J=8.2 Hz), 7.42-7.34 (4H, m), 7.28 (5H, dd, J=0.0, 3.3 Hz), 7.21 (1H, t, J=4.4 Hz), 6.41 (1H, s), 5.75 (2 H, s), 4.05 (2H, s).

EXAMPLE 23

4-(4-Fluoro-phenyl)-7-(4-pyridin-2-yl-[1,2,3]triazol-1-ylmethyl)-chromen-2-one

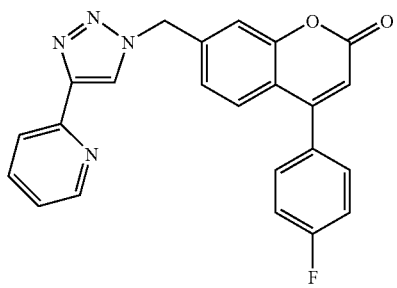

$^1$H NMR (400 MHz, CDCl$_3$): 8.57 (d, 1H), 8.23 (d, 1H), 8.16 (s, 1H), 7.82 (t, 1H), 7.51-7.41 (m, 3H), 7.38 (s, 1H), 7.30-7.22 (m, 3H), 7.18 (d, 1H), 6.39 (s, 1H), 5.70 (s, 2H).

EXAMPLE 24

4-(4-Fluoro-phenyl)-7-[4-(1-oxy-pyridin-2-yl)-[1,2,3]triazol-1-ylmethyl]-chromen-2-one

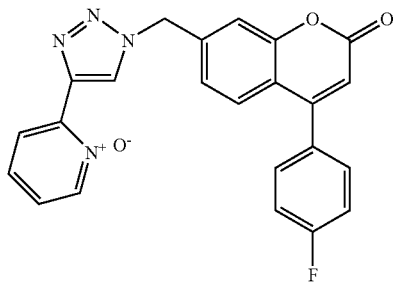

To a solution of 4-(4-fluoro-phenyl)-7-(4-pyridin-2-yl-[1,2,3]triazol-1-ylmethyl)-chromen-2-one in a mixture of dichloromethane/methanol (9:1, 2 mL) magnesium monoperoxyphthalate hexahydrate was added (62 mg, 1.2 eq). The reaction mixture was then stirred overnight at room temperature. The crude reaction mixture was then diluted with water and the product was extracted with dichloromethane (3×). The combined organic extracts were washed with water and brine, dried over MgSO$_4$, filtered and concentrated to afford the title compound. $^1$H NMR (400 MHz, CDCl$_3$): 9.04 (s, 1H), 8.54 (d, 1H), 8.33 (d, 1H), 7.50-7.40 (m, 3H), 7.37 (s, 1H), 7.30-7.20 (m, 3H), 7.17 (d, 1H), 6.39 (s, 1H), 5.73 (s, 2H).

EXAMPLE 25

7-[4-(Dicyclopropyl-hydroxy-methyl)-[1,2,3]triazol-1-ylmethyl]-4-(3-fluoro-phenyl)-chromen-2-one

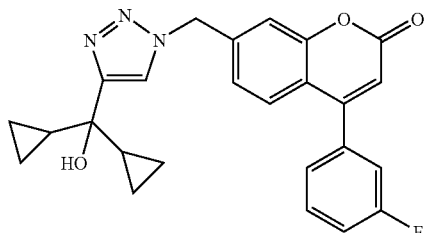

Step 1: 1,1-dicyclopropyl-3-(trimethylsilyl)prop-2-yn-1-ol

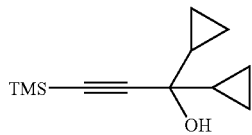

To a solution of trimethylsilylacetylene (5 mL, 35.4 mmol) in THF (100 mL) cooled at −78° C., a 1.6M n-butyllithium in hexanes (22.1 mL, 35.4 mmol) was added dropwise. The solution was stirred for 30 min before dicyclopropyl ketone (4.06 mL, 35.4 mmol) was added. The temperature was then slowly raised to room temperature and the reaction was stirred overnight. The reaction was then poured into a saturated ammonium chloride solution and the aqueous layer was extracted twice with ethyl acetate. The combined organic layers were washed with brine, dried over MgSO$_4$, filtered and concentrated under reduced pressure. The crude residue obtained was used as such for the next step. $^1$H NMR (400 MHz, acetone-d$_6$): 4.14 (s, 1H), 1.22-1.10 (m, 2H), 0.65-0.55 (m, 2H), 0.50-0.30 (m, 6H), 0.14 (s, 9H).

Step 2: 1,1-dicyclopropylprop-2-yn-1-ol

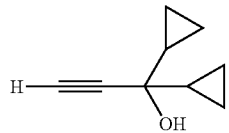

To a solution of 1,1-dicyclopropyl-3-(trimethylsilyl)prop-2-yn-1-ol (2.25 g, 10.6 mmol) in THF (100 mL), a 1M solution of tetrabutyl ammonium fluoride in THF (37.2 mL, 37.2 mmol) was added. The reaction was then stirred 1 hour at room temperature. The reaction mixture was then poured into an aqueous 5% NH$_4$OAc solution and diluted with ethyl acetate. The isolated organic layer was washed with brine, dried over MgSO$_4$, filtered and concentrated. The crude residue obtained was purified by column chromatography (ethyl acetate/hexanes, 20:80) to afford the title compound. $^1$H NMR (400 MHz, acetone-d$_6$): 4.17 (s, 1H), 2.75 (s, 1H), 1.25-1.15 (m, 2H), 0.65-0.55 (m, 2H), 0.55-0.30 (m, 6H).

Step 3: 7-[4-(Dicyclopropyl-hydroxy-methyl)-[1,2,3]triazol-1-ylmethyl]-4-(3-fluoro-phenyl)-chromen-2-one was prepared using 1,1-dicyclopropylprop-2-yn-1-ol and 7-(azidomethyl)-4-(3-fluorophenyl)-2H-chromen-2-one (example 1, step 7), following the general cycloaddition procedure described in example 12. $^1$H NMR (400 MHz, acetone-d$_6$): 7.95 (s, 1H), 7.70-7.60 (m, 1H), 7.54 (d, 1H), 7.44-7.34 (m, 4H), 7.30 (d, 1H), 6.43 (s, 1H), 5.78 (s, 2H), 3.7 (s, 1H), 1.45-1.35 (m, 2H), 0.55-0.45 (m, 4H), 0.45-0.35 (m, 2H), 0.30-0.20 (m, 2H).

EXAMPLE 26

7-[4-(Dicyclopropyl-hydroxy-methyl)-[1,2,3]triazol-1-ylmethyl]-4-(4-fluoro-phenyl)-chromen-2-one

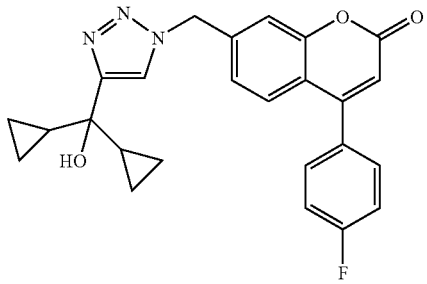

7-(Azidomethyl)-4-(4-fluorophenyl)-2H-chromen-2-one was prepared using the general procedure described in example 1, steps 3-7, but substituting 4-fluorobenzeneboronic acid in place of 3-fluorobenzeneboronic acid. The title compound was prepared using 1,1-dicyclopropylprop-2-yn-1-ol and 7-(azidomethyl)-4-(4-fluorophenyl)-2H-chromen-2-one using the general cycloaddition procedure described in example 12. $^1$H NMR (400 MHz, acetone-d$_6$): $^1$H NMR (400 MHz, acetone-d$_6$): 7.95 (s, 1H), 7.7-7.65 (m, 1H), 7.52 (d, 1H), 7.40-7.35 (m, 3H), 7.30 (d, 1H), 6.40 (s, 1H), 5.80 (s, 2H), 3.72 (s, 1H), 1.45-1.35 (m, 2H), 0.55-0.45 (m, 4H), 0.45-0.35 (m, 2H), 0.30-0.20 (m, 2H).

EXAMPLE 27

4-(3-fluorophenyl)-7-{[4-(1-hydroxy-1-(trifluoromethyl)propyl)-5-methyl-1H-1,2,3-triazol-1-yl]methyl]-2H-chromen-2-one

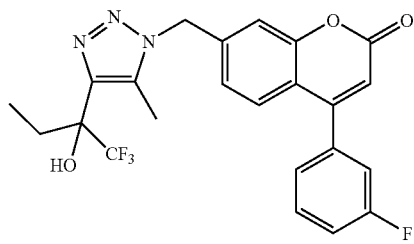

Step 1: 3-(trifluoromethyl)hex-4-yn-3-ol

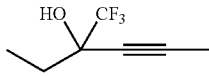

To ethyl trifluoromethyl ketone (5.00 g, 40.0 mmol) in THF (20 ml) at room temperature was added 1-propynyl magnesium bromide (0.5 M in THF, 60 mL, 30.0 mmol). The reaction mixture was allowed to stand at rt 1 h, and concentrated in vacuo. The residue was partitioned between Et$_2$O and aq. NH$_4$OAc, the phases were separated, and the organic phase washed with brine, dried over MgSO$_4$, filtered and concentrated (not to complete dryness), to afford a 50 wt. % solution (estimated by $^1$H NMR) of the title compound (remainder THF and Et$_2$O), which was used without further purification. $^1$H NMR (400 MHz, DMSO-d$_6$): 6.63 (s, 1H), 1.87 (s, 3H), 1.75-1.63 (m, 2H), 1.04 (t, 3H).

Step 2: 4-(3-fluorophenyl)-7-{[4-(1-hydroxy-1-(trifluoromethyl)propyl)-5-methyl-1H-1,23-triazol-1-yl}methyl]-2H-chromen-2-one A solution of 7-(azidomethyl)-4-(3-fluorophenyl)-2H-chromen-2-one (458 mg, 1.55 mmol) and the alkyne from step 1 (1.5 g, 50 wt. % in Et$_2$O/THF, 4.51 mmol) in toluene (15 mL) was degassed by two freeze, pump and thaw cycles. The solution was heated to 140° C. overnight, cooled and concentrated in vacuo. The residue was purified by flash chromatography (30-60% EtOAc/hexanes) to afford the title compound. MS (−APCI): 460 (M−H)$^−$.

The minor regioisomer was also isolated (2.5:1 ratio of regioisomers).

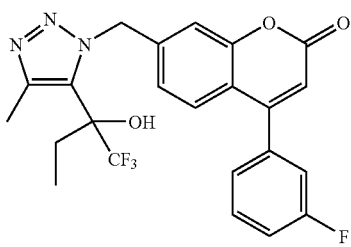

4-(3-fluorophenyl)-7-({5-[1-hydroxy-1-(trifluoromethyl)propyl]-4-methyl-1H-1,2,3-triazol-1-yl}methyl)-2H-chromen-2-one $^1$H NMR (400 MHz, acetone-$d_6$): 7.69-7.62 (m, 1H), 7.48 (d, 1H), 7.45-7.33 (m, 3H), 7.20-7.11 (m, 2H), 6.38 (s, 1H), 6.17 (s, 1H), 6.13 (d, 1H), 5.92 (d, 1H) 2.58-2.42 (m, 2H), 2.39 (s, 3H), 1.87 (t, 3H).

EXAMPLE 28

4-(3-fluorophenyl)-7-{[4-(1-hydroxy-1-(trifluoromethyl)ethyl)-1H-1,2,3-triazol-1-yl]methyl]-2H-chromen-2-one

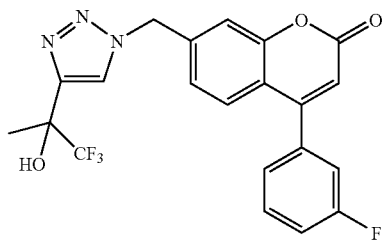

Step 1: 1,1,1-Trifluoro-2-methyl-4-(trimethylsilyl)but-3-yn-2-ol

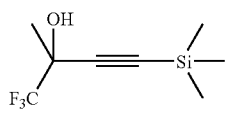

To a solution of (trimethylsilyl)acetylene (2.80 mL, 20.2 mmol) in Et$_2$O (25 mL) at –78° C., was added n-BuLi (2.5 M in hexane, 8.10 mL, 20.2 mmol), while maintaining internal temperature below –70° C. After 30 min., a solution of 1,1,1-trifluoroacetone (3.62 mL, 40.5 mmol) in Et$_2$O (10 mL) was added rapidly, keeping the internal temperature below –45° C. After 2 h at –78° C., a saturated solution of NH$_4$Cl was added. The aqueous layer was extracted with Et$_2$O, and the combined organic layers were washed with brine, dried (Na$_2$SO$_4$) and concentrated under vacuum, at 25° C., affording the title compound a liquid containing Et$_2$O (7.25 g). The crude product was used as such in Step 2. $^1$H NMR (400 MHz, acetone-$d_6$): 5.92 (br s, 1H), 1.59 (s, 3H), 0.18 (s, 9H).

Step 2: 1-Methyl-1-(trifluoromethyl)prop-2-yn-1-yl 4-nitrobenzoate

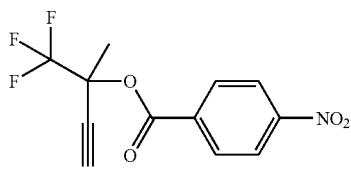

A solution of crude 1,1,1-trifluoro-2-methyl-4-(trimethylsilyl)but-3-yn-2-ol from Step 1 (~20.2 mmol) in DMF (10 mL) was added dropwise to a suspension of NaH (60% disp., 850 mg, 21.2 mmol) in DMF (25 mL) at 0° C. The mixture was allowed to reach room temperature, stirred for 30 min. and recooled to 0° C. A solution of 4-nitrobenzoyl chloride (3.94 g, 21.2 mmol) in DMF (10 mL) was added dropwise and the resulting mixture was stirred at room temperature. After 30 min., the mixture was poured in 1:1 25% NH$_4$OAc/H$_2$O and extracted with Et$_2$O (3×). The combined organic layers were washed with H$_2$O (3×) and brine, dried (Na$_2$SO$_4$) and concentrated. The residue was subjected to chromatography on silica gel (toluene/hexane 40:60 to 60:40) affording the title compound. $^1$H NMR (400 MHz, acetone-$d_6$): 8.44 (d, 2H), 8.28 (d, 2H), 3.65 (s, 1H), 2.09 (s, 3H).

Step 3: 2,2,2-Trifluoro-1-(1-{[4-(3-fluorophenyl)-2-oxo-2H-chromen-7-yl]methyl}-1H-1,2,3-triazol-4-yl)-1-methylethyl 4-nitrobenzoate The title compound was obtained following the general cycloaddition procedure (example 1, step 8). $^1$H NMR (400 MHz, acetone-$d_6$): 8.51 (s, 1H), 8.42 (d, 2H), 8.27 (d, 2H), 7.66 (m, 1H), 7.52 (d, 1H), 7.36-7.42 (m, 4H), 7.30 (dd, 1H), 6.43 (s, 1H), 5.87 (s, 2H), 2.33 (s, 3H).

Step 4: 4-(3-fluorophenyl)-7-{[4-(1-hydroxy-1-(trifluoromethyl)ethyl)-1H-1,2,3-triazol-1-yl]methyl]-2H-chromen-2-one The title compound was obtained following the general deprotection procedure (example 1, step 9). MS (+APCI): 434 (M+H)$^+$.

EXAMPLE 29

7-{[4-(1-Cyclopropyl-2,2,2-trifluoro-1-hydroxyethyl)-1H-1,2,3-triazol-1-yl]methyl}-4-(3-fluorophenyl)-2H-chromen-2-one

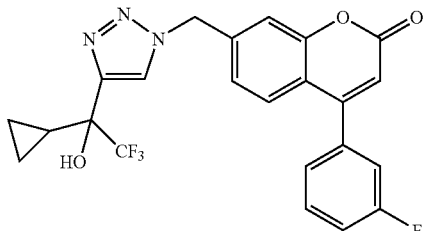

Step 1: 1,1,1-Trifluoro-4-(triisopropylsilyl)but-3-yn-2-one

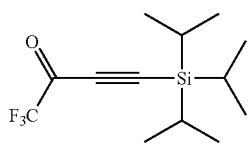

To a solution of (triisopropylsilyl)acetylene (6.50 mL, 29.0 mmol) in THF (80 mL) at −78° C. was added n-BuLi (2.5 M in hexane, 12.2 mL, 30.4 mmol) while maintaining the internal temperature below −70° C. After 30 min., ethyl trifluoroacetate (4.14 mL, 34.8 mmol) was added dropwise, keeping the internal temperature below −73° C. After 15 min. at −78° C., the mixture was allowed to reach 0° C. After 2 h, a saturated solution of NH$_4$Cl was added. The aqueous layer was extracted with EtOAc (3×), and the combined organic layers were washed with brine, dried (Na$_2$SO$_4$) and concentrated affording the title compound. $^1$H NMR (400 MHz, acetone-d$_6$): 1.27 (m, 3H), 1.16 (d, 18H).

Step 2: 2-Cyclopropyl-1,1,1-trifluoro-4-(triisopropylsilyl)but-3-yn-2-ol

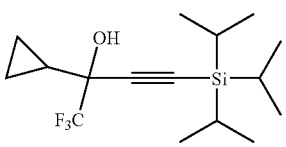

To a solution of 1,1,1-trifluoro-4-(triisopropylsilyl)but-3-yn-2-one (2.01 g, 7.22 mmol) in CH$_2$Cl$_2$ (50 mL) at 0° C. was added a THF solution of cyclopropylmagnesium bromide (0.5 M, 21.7 mL, 10.8 mmol). After 1.5 h, a saturated solution of NH$_4$Cl was added. The aqueous layer was extracted with CHCl$_3$ (3×), and the combined organic layers were washed with H$_2$O and brine, dried (Na$_2$SO$_4$) and concentrated under vacuum at 30° C. affording the title compound. $^1$H NMR (500 MHz, acetone-d$_6$): 5.97 (s, 1H), 1.36 (m, 1H), 1.10 (m, 21H), 0.74 (m, 1H), 0.65 (m, 2H), 0.60 (m, 1H).

Step 3: 1-Cyclopropyl-1-(trifluoromethyl)-3-(triisopropylsilyl)prop-2-yn-1-yl-4-nitrobenzoate

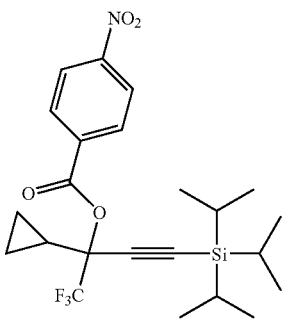

To a 0° C. solution of crude 2-cyclopropyl-1,1,1-trifluoro-4-(triisopropylsilyl)but-3-yn-2-ol from Step 2 (~8.14 mmol) in DMF (15 mL) was added NaH (60% disp., 342 mg, 8.55 mmol) portionwise. The mixture was allowed to reach room temperature and stirred for 40 min. A solution of 4-nitrobenzoyl chloride (1.59 g, 8.55 mmol) in DMF (5 mL) was added dropwise while maintaining internal temperature below 32° C., and the resulting mixture was stirred at room temperature. After 2 h, the mixture was poured in 1:1 25% NH$_4$OAc/H$_2$O and extracted with EtOAc (3×). The combined organic layers were washed with H$_2$O (3×) and brine, dried (Na$_2$SO$_4$) and concentrated, affording the title compound contaminated with a trace of desilylated material. $^1$H NMR (400 MHz, acetone-d$_6$): 8.44 (d, 2H), 8.29 (d, 2H), 1.52 (m, 1H), 1.11 (m, 21H), 0.75-0.97 (m, 4H).

Step 4: 1-Cyclopropyl-1-(trifluoromethyl)prop-2-yn-1-yl 4-nitrobenzoate

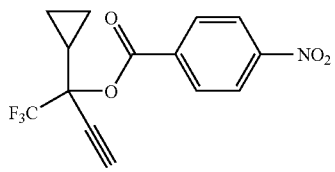

To a solution of crude 1-cyclopropyl-1-(trifluoromethyl)-3-(triisopropylsilyl)prop-2-yn-1-yl 4-nitrobenzoate from Step 3 (~8.14 mmol) in THF (30 mL) at room temperature was added a THF solution of tetrabutylammonium fluoride (1.0 M, 9.77 mL, 9.77 mmol). After 1.5 h the reaction mixture was poured in H$_2$O and extracted with EtOAc (3×). The combined organic layers were washed with H$_2$O and brine, dried (Na$_2$SO$_4$) and concentrated. The residue was subjected to chromatography on silica gel (toluene/hexane 40:60 to 60:40) affording the title compound. $^1$H NMR (400 MHz, acetone-d$_6$): 8.44 (d, 2H), 8.29 (d, 2H), 3.64 (s, 1H), 1.53 (m, 1H), 1.26 (m, 1H), 0.88 (m, 2H), 0.78 (m, 1H).

Step 5: 1-Cyclopropyl-2,2,2-trifluoro-1-(1-{[4-(3-fluorophenyl)-2-oxo-2H-chromen-7-yl]methyl}-1H-1,2,3-triazol-4-yl)ethyl 4-nitrobenzoate The title compound was obtained following the general cycloaddition procedure (example 1, step 8). $^1$H NMR (500 MHz, acetone-d$_6$): 8.50 (s, 1H), 8.43 (d, 2H), 8.28 (d, 2H), 7.66 (m, 1H), 7.54 (d, 1H), 7.36-7.43 (m, 4H), 7.30 (dd, 1H), 6.44 (s, 1H), 5.88 (s, 2H), 1.95 (m, 1H), 1.08 (m, 1H), 0.98 (m, 1H), 0.89 (m, 1H), 0.82 (m, 1H).

Step 6: 7-{[4-(1-Cyclopropyl-2,2,2-trifluoro-1-hydroxyethyl)-1H-1,2,3-triazol-1-yl]methyl}-4-(3-fluorophenyl)-2H-chromen-2-one The title compound was obtained following the general deprotection procedure (example 1, step 9). MS (−ESI): 458 (M−H)$^-$.

EXAMPLE 30

4-(3-Fluorophenyl)-7-({4-[1-hydroxy-1-(trifluoromethyl)butyl]-1H-1,2,3-triazol-1-yl}methyl)-2H-chromen-2-one

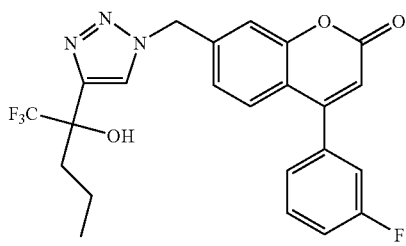

Step 1: 3-(Trifluoromethyl)-1-(triisopropylsilyl)hex-5-en-1-yn-3-ol

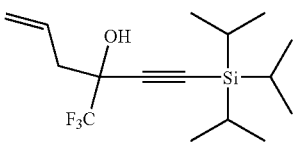

To a solution of 1,1,1-trifluoro-4-(triisopropylsilyl)but-3-yn-2-one (3.00 g, 10.8 mmol) in CH$_2$Cl$_2$ (80 mL) at 0° C., was added a THF solution of allylmagnesium chloride (2.0 M, 8.08 mL, 16.2 mmol). After 1 h, a saturated solution of NH$_4$Cl was added. The aqueous layer was extracted with CHCl$_3$ (3×), and the combined organic layers were washed with H$_2$O and brine, dried (Na$_2$SO$_4$) and concentrated under vacuum at 30° C. affording the title compound (3.63 g). $^1$H NMR (400 MHz, acetone-d$_6$): 6.02 (m, 2H), 5.20-5.27 (m, 2H), 2.62 (m, 2H), 1.10 (m, 21H).

Step 2: 1-(Trifluoromethyl)-1-[(triisopropylsilyl)ethynyl]but-3-en-1-yl 4-nitrobenzoate

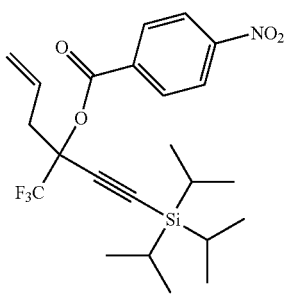

To a 0° C. solution of crude 3-(trifluoromethyl)-1-(triisopropylsilyl)hex-5-en-1-yn-3-ol from Step 1 (242 mg, 0.755 mmol) in DMF (2 mL) was added NaH (60% disp., 32 mg, 0.793 mmol) in two portions. The mixture was allowed to reach room temperature and stirred for 40 min. A solution of 4-nitrobenzoyl chloride (147 mg, 0.793 mmol) in DMF (1 mL) was added dropwise. After 1.5 h, the mixture was poured in H$_2$O and extracted with EtOAc (3×). The combined organic layers were washed with H$_2$O (3×) and brine, dried (Na$_2$SO$_4$) and concentrated, affording the title compound (342 mg).

Step 3: 1-Ethynyl-1-(trifluoromethyl)but-3-en-1-yl 4-nitrobenzoate

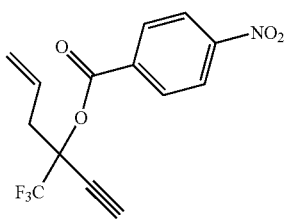

To a solution of crude 1-(trifluoromethyl)-1-[(triisopropylsilyl)ethynyl]but-3-en-1-yl 4-nitrobenzoate from Step 2 (~0.755 mmol) in THF (3 mL) at room temperature was added a THF solution of tetrabutylammonium fluoride (1.0 M, 0.906 mL, 0.906 mmol). After 2.5 h the reaction mixture was poured in H$_2$O and extracted with EtOAc (3×). The combined organic layers were washed with H$_2$O and brine, dried (Na$_2$SO$_4$) and concentrated. The residue was subjected to chromatography on silica gel (toluene/hexane 40:60 to 60:40) affording the title compound (60 mg). $^1$H NMR (500 MHz, acetone-d$_6$): 8.44 (d, 2H), 8.29 (d, 2H), 5.94 (m, 1H), 5.29 (d, 1H), 5.21 (d, 1H), 3.74 (s, 1H), 3.27 (m, 2H).

Step 4: 1-(1-{[4-(3-Fluorophenyl)-2-oxo-2H-chromen-7-yl]methyl}-1H-1,2,3-triazol-4-yl)-1-(trifluoromethyl)but-3-en-1-yl 4-nitrobenzoate

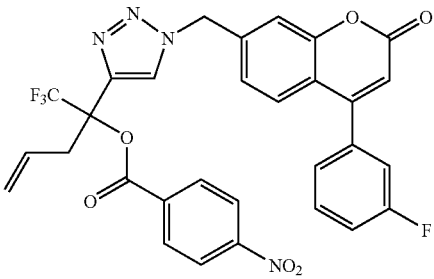

The title compound was obtained following the general cycloaddition procedure (example 1, step 8). $^1$H NMR (400 MHz, acetone-d$_6$): 8.53 (s, 1H), 8.42 (d, 2H), 8.27 (d, 2H), 7.66 (m, 1H), 7.53 (d, 1H), 7.36-7.43 (m, 4H), 7.30 (dd, 1H), 6.44 (s, 1H), 6.00 (m, 1H), 5.88 (s, 2H), 5.24 (d, 1H), 5.15 (d, 1H), 3.81 (dd, 1H), 3.55 (dd, 1H).

Step 5: 4-(3-Fluorophenyl)-7-({4-[1-hydroxy-1-(trifluoromethyl)but-3-en-1-yl]-1H-1,2,3-triazol-1-yl}methyl)-2H-chromen-2-one

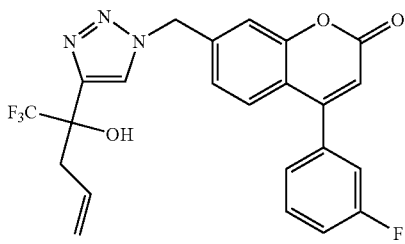

The title compound was obtained following the general deprotection procedure (example 1, step 9). $^1$H NMR (500 MHz, acetone-d$_6$): 8.22 (s, 1H), 7.66 (m, 1H), 7.54 (d, 1H), 7.36-7.44 (m, 4H), 7.30 (dd, 1H), 6.44 (s, 1H), 5.86 (s, 2H), 5.70 (m, 1H), 5.63 (s, 1H), 5.14 (d, 1H), 5.05 (d, 1H), 3.10 (dd, 1H), 2.86 (dd, 1H).

Step 6: 4-(3-Fluorophenyl)-7-({4-[1-hydroxy-1-(trifluoromethyl)butyl]-1H-1,2,3-triazol-1-yl}methyl)-2H-chromen-2-one A solution of 4-(3-fluorophenyl)-7-({4-[1-hydroxy-1-(trifluoromethyl)but-3-en-1-yl]-1H-1,2,3-triazol-1-yl}methyl)-2H-chromen-2-one from Step 5 (56 mg, 0.122 mmol) in EtOAc (2 mL) was stirred under H$_2$ (1 atm), in the presence of 10% Pd/C (12 mg), for 17 h. After H$_2$ was evacuated and the system purged with nitrogen, the reaction mixture was filtered through celite. The cake was rinsed with EtOAc and the filtrate concentrated. The residue was subjected to chromatography on silica gel (EtOAc/toluene 25:75) affording the title compound (50 mg). MS (-ESI): 460 (M-H)$^-$.

EXAMPLE 31

4-(3-Methylphenyl)-7-({4-[1-ethyl-1-hydroxypropyl]-1H-1,2,3-triazol-1-yl}methyl)-2H-chromen-2-one

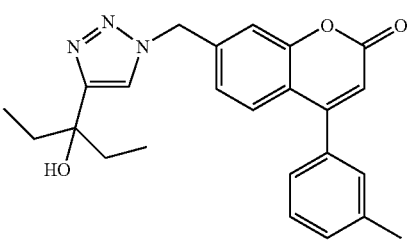

Step 1: 7-bromo-4-(3-methylphenyl)-2H-chromen-2-one

To a solution of 7-bromo-2-oxo-2H-chromen-4-yl trifluoromethanesulfonate (prepared as described in U.S. Pat. No. 5,552,437) (1.1 g, 3.0 mmol) and 3-methylbenzeneboronic acid (450 mg, 3.3 mmol) in THF (12 mL), tricyclohexylphosphine (30 mg, 0.1 mmol) and potassium fluoride (574 mg, 9.9 mmol) were added. The reaction mixture was purged twice with nitrogen before palladium (II) acetate (20 mg, 0.1 mmol) was added. After 16 hours stirring at room temperature the reaction mixture was filtered over celite and the filtrate was concentrated under reduced pressure. The crude residue obtained was purified by column chromatography ($CH_2Cl_2$/hexanes, 70:30). To afford the title compound $^1$H NMR (400 MHz, acetone-$d_6$): 7.67 (s, 1H), 7.53-7.33 (m, 6H), 6.40 (s, 1H), 2.46 (s, 3H).

Step 2: methyl 4-(3-methylphenyl)-2-oxo-2H-chromene-7-carboxylate

A solution of 7-bromo-4-(3-methylphenyl)-2H-chromen-2-one (740 mg, 2.34 mmol), [1,1'-bis(diphenylphosphino)-ferrocene]dichloropalladium (II) complexed with $CH_2Cl_2$ (383 mg, 0.47 mmol) and triethylamine (650 uL, 4.7 mmol) in a mixture of methanol (7.5 mL) and dimethylsulfoxide (14 mL) was flushed with carbon monoxide twice at 0° C. The mixture was then heated at 65° C. under a carbon monoxide atmosphere and vigorously stirred overnight. After cooling, the reaction mixture was poured into a saturated ammonium chloride solution. The product was extracted with ethyl acetate (3×) and the combined organic extracts were washed with water (3×), brine and dried over $MgSO_4$, filtered and concentrated under reduced pressure. The crude oil obtained was purified by column chromatography (ethyl acetate/hexanes, 20:80) to afford the title compound. $^1$H NMR (400 MHz, acetone-$d_6$): 7.95 (s, 1H), 7.91 (d, 1H), 7.67 (d, 1H), 7.50 (t, 1H), 7.46-7.34 (m, 3H), 6.47 (s, 1H), 3.96 (s, 3H), 2.47 (s, 3H).

Step 3: 4-(3-methylphenyl)-2-oxo-2H-chromene-7-carboxylic acid

To a solution of methyl 4-(3-methylphenyl)-2-oxo-2H-chromene-7-carboxylate (610 mg, 2.1 mmol) in THF (21 mL) a solution of lithium hydroxide (10.3 mL, 10.3 mmol) was added. The solution was then heated at 65° C. for 2 hours. After cooling, volatiles were removed under reduced pressure and the residue obtained was diluted with THF (20 mL) and 2N HCl (40 mL). After 1 h stirring, the solid formed was collected by filtration to afford the title compound. $^1$H NMR (400 MHz, DMSO-$d_6$): 13.5 (bs, 1H), 7.90 (d, 1H), 7.87 (dd, 1H), 7.59 (d, 1H), 7.48 (t, 1H), 7.43-7.33 (m, 3H), 6.55 (s, 1H), 2.41 (s, 3H).

Step 4: 7-(hydroxymethyl)-4-(3-methylphenyl)-2H-chromen-2-one

To a solution of 4-(3-methylphenyl)-2-oxo-2H-chromene-7-carboxylic acid (520 mg, 1.86 mmol) and triethylamine (1.0 mL, 7.4 mmol) in THF (15 mL), cooled at 0° C., isobutylchloroformate (726 uL, 5.6 mmol) was added dropwise. After 1 hour stirring at 0° C. a solution of sodium borohydride in water (353 mg, 9.3 mmol in 6 mL) was added slowly and the mixture was stirred for another hour. The reaction mixture was poured into a saturated ammonium chloride solution and the product was extracted (3×) with ethyl acetate, the combined organic extracts were washed with water and brine, dried over $MgSO_4$, filtered and concentrated under reduced pressure. The crude residue obtained was purified by column chromatography (ethyl acetate/hexanes, 50:50) to afford the title compound. $^1$H NMR (400 MHz, acetone-$d_6$): 7.51-7.39 (m, 5H), 7.37 (d, 1H), 7.32 (d, 1H), 6.29 (s, 1H), 4.79 (d, 2H), 4.57 (t, 1H), 2.46 (s, 3H).

Step 5: 7-(azidomethyl)-4-(3-methylphenyl)-2H-chromen-2-one

To a suspension of 7-(hydroxymethyl)-4-(3-methylphenyl)-2H-chromen-2-one (757 mg, 2.6 mmol) in toluene (12 mL) was added triphenylphosphine (922 mg, 3.5 mmol) and $Zn(N_3)_2$.2 pyridine (prepared as described in Synthesis, 1990, p. 130-132) (406 mg, 1.3 mmol). After 10 minutes of stirring, N,N-diisopropyl azodicarboxylate (692 uL, 3.5 mmol) was added dropwise. After 3 hours of stirring, the solution was concentrated under reduced pressure. The crude residue obtained was purified by column chromatography (ethyl acetate/toluene, 15:85) to afford the title compound. $^1$H NMR (400 MHz, acetone-$d_6$): 7.58 (d, 1H), 7.52-7.46 (m, 2H), 7.44-6.33 (m, 4H), 6.34 (s, 1H), 4.64 (s, 2H), 2.48 (s, 3H).

Step 6: 7-{[4-(1-ethyl-1-hydroxypropyl)-1H-1,2,3-triazol-1-yl]methyl}-4-(3-methylphenyl)-2H-chromen-2-one To a solution of 7-(azidomethyl)-4-(3-methylphenyl)-2H-chromen-2-one (100 mg, 0.34 mmol) and 3-ethyl-1-pentyn-3-ol (46 mg, 0.41 mmol) in THF (4 mL) N,N-diisopropyl-ethylamine (296 uL, 1.7 mmol) and copper iodide (97 mg, 0.51 mmol) were added. After overnight stirring, the reaction was diluted with ethyl acetate, filtered and washed with water and brine. The organic layer was then dried over $MgSO_4$, filtered and concentrated. The crude residue obtained was purified by column chromatography (acetone/$CH_2Cl_2$ 20:80) to afford the title compound. $^1$H NMR (400 MHz, acetone-$d_6$): 7.90 (s, 1H), 7.54 (d, 1H), 7.47 (t, 1H), 7.43-7.33 (m, 4H), 7.25 (d, 1H), 6.33 (s, 1H), 5.78 (s, 2H), 3.70 (s, 1H), 2.45 (s, 3H), 1.95-1.75 (m, 4H), 0.79 (t, 6H).

EXAMPLE 32

7-[4-(1-Ethyl-1-hydroxy-propyl)-[1,2,3]triazol-1-ylmethyl]-4-pyridin-3-yl-chromen-2-one

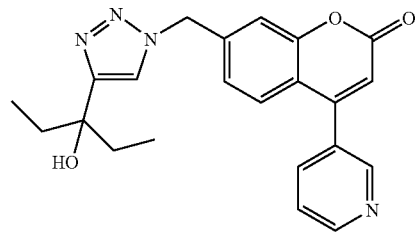

Step 1: 2-oxo-4-pyridin-3-yl-2H-chromen-7-yl trifluoromethanesulfonate

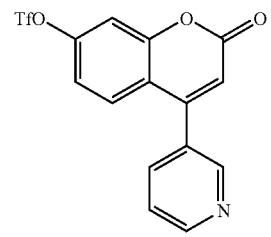

To a solution of commercially available 7-hydroxy-4-(pyridine-3-yl) coumarin (5 g, 20.9 mmol) and triethylamine (3.8 mL, 27 mmol) in dichloromethane (75 mL) cooled at −30° C. a solution of triflic anhydride in $CH_2Cl_2$ (4.24 mL, 25 mmol in 25 mL) was added dropwise (internal temperature kept below −30° C. during addition). After addition, the mixture was stirred 1 hour at −30° C. and then slowly warmed to 0° C. The reaction was poured into a saturated solution of ammonium chloride and the aqueous layer was extracted twice with dichloromethane. The combined organic extracts were washed with brine, dried over MgSO$_4$, filtered and concentrated. The crude residue obtained was used as such for the next step. $^1$H NMR (400 MHz, acetone-d$_6$): 8.90-8.80 (m, 2H), 8.11 (d, 1H), 7.75-7.65 (m, 3H), 7.47 (d, 1H), 6.61 (s, 1H).

Step 2: Methyl 2-oxo-4-(3-pyridinyl)-2H-chromene-7-carboxylate

To a mixture of 2-oxo-4-pyridin-3-yl-2H-chromen-7-yl trifluoromethanesulfonate (6.4 g, 17.24 mmol) in DMSO (100 mL) stirred at room temperature, triethylamine (4.85 mL, 34.5 mmol) was added. The reaction was then purged twice with carbon monoxide and palladium dichloride-(dppf)-dichloromethane (2.82 g, 3.45 mmol) was added. The mixture was purged once again with carbon monoxide and the reaction was stirred overnight at 65° C. under carbon monoxide atmosphere. After cooling, the reaction was quenched by the addition of an aqueous saturated ammonium chloride solution. The aqueous layer was extracted (3×) with ethyl acetate and the combined organic extracts were dried over MgSO$_4$, filtered and concentrated. The crude residue obtained was purified by column chromatography (acetone/CH$_2$Cl$_2$, 10:90). MS (+ESI) 282.2 (M+H)$^+$.

Step 3: 7-[4-(1-Ethyl-1-hydroxy-propyl)-[1,2,3]triazol-1-yl-methyl]-4-pyridin-3-yl-chromen-2-one The title compound was prepared from methyl 2-oxo-4-(3-pyridinyl)-2H-chromene-7-carboxylate, using the procedures described in the example 31, starting from step 3. $^1$H NMR (400 MHz, acetone-d$_6$): 8.78 (s, 2H), 8.04 (d, 1H), 7.90 (s, 1H), 7.64-7.36 (m, 1H), 7.48 (d, 1H), 7.35 (s, 1H), 7.27 (d, 1H), 6.47 (s, 1H), 5.80 (s, 2H), 3.80 (s, 1H), 1.95-1.75 (m, 4H), 0.77 (t, 6H).

EXAMPLE 33

(S)-7-({4-[1-hydroxy-1-(trifluoromethyl)propyl]-1H-1,2,3-triazol-1-yl}methyl)-4-(5-methylisoxazol-3-yl)-2H-chromen-2-one

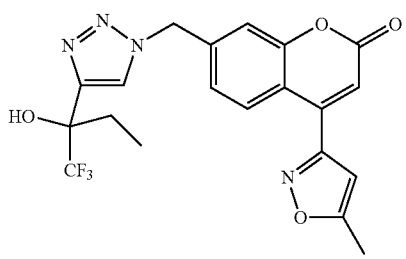

Step 1: 1-(methoxymethoxy)-3-methylbenzene

To m-cresol (19.4 mL, 188 mmol) in DMF (1 L) was added NaH (60% disp. in oil, 9.04 g, 0.226 mmol) in several portions. The mixture was stirred at rt for 30 min, chloromethyl methyl ether (11.5 mL, 151 mmol) was added in one portion, and the reaction mixture was stirred at room temperature overnight, partitioned between 1N aq. NaOH and Et$_2$O. The organic phase was washed with 1N aq. NaOH, dried over MgSO$_4$, filtered and concentrated in vacuo, to afford the title compound. $^1$H NMR (400 MHz, acetone-d$_6$): 7.18 (t, 1H), 6.86-6.77 (m, 3H), 5.18 (s, 2H), 3.43 (s, 3H), 2.29 (s, 3H).

Step 2: [2-(methoxymethoxy)-4-methylphenyl](5-methylisoxazol-3-yl)methanone

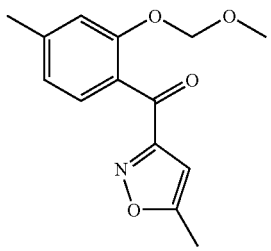

To a solution of t-BuLi (1.7 M in pentane, 9.96 mL, 16.9 mmol) was added dropwise 1-(methoxymethoxy)-3-methylbenzene from step 1 (2.34 g, 15.4 mmol), maintaining the internal temperature below 8° C. The suspension was stirred at 0° C. for 1 h, cooled to −20° C., and THF (40 mL) was added. The suspension was allowed to warm to −8° C., cooled to −78° C., and Weinreb amide (see below) was added (2.75 g, 16.2 mmol). The cooling bath was removed and the reaction mixture was allowed to warm to 0° C., partitioned between Et$_2$O and H$_2$O, and the organic phase was washed with brine, dried over MgSO$_4$, filtered and concentrated in vacuo. The residue was purified by flash chromatography (10-20% EtOAc in hexanes) to afford the title compound. $^1$H NMR (400 MHz, acetone-d$_6$): 7.45 (d, 1H), 7.08 (s, 1H), 6.94 (d, 1H), 6.51 (s, 1H), 5.13 (s, 2H), 3.33 (s, 3H), 2.53 (s, 3H), 2.38 (s, 3H).

Weinreb amide:

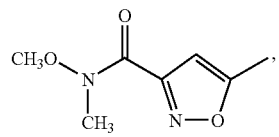

prepared using the general procedure described in Example 36, step 1.

Step 3: (2-hydroxy-4-methylphenyl)(5-methylisoxazol-3-yl)methanone

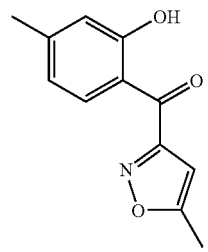

To a solution of [2-(methoxymethoxy)-4-methylphenyl](5-methylisoxazol-3-yl)methanone from step 2 (1.49 g, 5.70 mmol) in isopropanol/THF (1:1, 50 mL) was added conc. HCl (1 mL) in one portion. The reaction mixture was stirred at 60° C. for 1.2 h, and extracted with Et$_2$O from NaHCO$_3$. The organic phase was washed with brine, dried over MgSO$_4$, filtered and concentrated in vacuo, to afford the title compound. MS (+APCI): 218 (M+H)$^+$.

Step 4: 7-methyl-4-(5-methylisoxazol-3-yl)-2H-chromen-2-one

A solution of (2-hydroxy-4-methylphenyl)(5-methylisoxazol-3-yl)methanone from step 3 (0.93 g, 4.28 mmol) and methyl(triphenylphosphoranylidene)acetate (1.86 g, 5.57 mmol) in toluene (30 mL) was heated to 90° C. for 2 h, concentrated in vacuo, and the residue washed with Et₂O and hot acetone to afford the title compound. ¹H NMR (400 MHz, acetone-d₆): 8.18 (d, 1H), 7.27-7.19 (m, 2H), 6.77 (s, 1H), 6.67 (s, 1H), 2.60 (s, 3H), 2.52 (s, 3H).

Step 5: 7-(azidomethyl)-4-(5-methylisoxazol-3-yl)-2H-chromen-2-one

A mixture of 7-methyl-4-(5-methylisoxazol-3-yl)-2H-chromen-2-one from step 4 (550 mg, 2.28 mmol), N-bromosuccinimide (446 mg, 2.51 mmol), and benzoyl peroxide (28 mg, 0.114 mmol) in CCl₄ (15 mL) was heated to reflux for 7.5 h, filtered hot and concentrated in vacuo to afford the crude bromide, which was used without further purification. The crude bromide and NaN₃ (180 mg, 2.77 mmol) in EtOH (15 mL) and DMF (10 mL) was heated to reflux 5 h, cooled to room temperature, taken up in Et₂O, washed with H₂O (2×) and brine, dried over MgSO₄, filtered and concentrated in vacuo. The residue was purified by flash chromatography (20-30% EtOAc in hexanes) to afford the title compound. ¹H NMR (400 MHz, acetone-d₆): 8.37 (d, 1H), 7.49-7.42 (m, 2H), 6.80 (s, 1H), 6.77 (s, 1H), 4.68 (s, 2H), 2.59 (s, 3H).

Step 6: (S)-1-(1-{[4-(5-methylisoxazol-3-yl)-2-oxo-2H-chromen-7-yl]methyl}-1H-1,2,3-triazol-4-yl)-1-(trifluoromethyl)propyl 4-nitrobenzoate The title compound was obtained following the general cycloaddition procedure (example 1, step 8). ¹H NMR (400 MHz, acetone-d₆): 8.50 (s, 1H), 8.43 (d, 2H), 8.37 (d, 1H), 8.41 (d, 2H), 7.38-7.32 (m, 2H), 6.79 (s, 1H), 6.77 (s, 1H), 5.88 (s, 2H), 3.11-2.98 (m, 1H), 2.90-2.78 (m, 1H), 2.58 (s, 3H), 1.14 (t, 3H).

Step 7: (S)-7-({4-[1-hydroxy-1-(trifluoromethyl)propyl]-1H-1,2,3-triazol-1-yl}methyl)-4-(5-methylisoxazol-3-yl)-2H-chromen-2-one The title compound was obtained following the general deprotection procedure (example 1, step 9). MS (−ESI): 433 (M−H)⁻.

EXAMPLE 34

(S)-7-({4-[1-hydroxy-1-(trifluoromethyl)propyl]-1H-1,2,3-triazol-1-yl}methyl)-4-(1,3-thiazol-2-yl)-2H-chromen-2-one

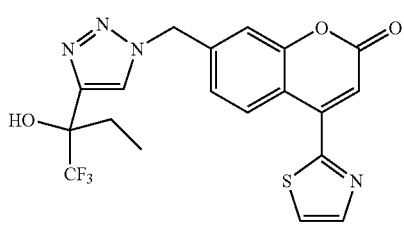

Step 1: [2-(methoxymethoxy)-4-methylphenyl](1,3-thiazol-2-yl)methanol

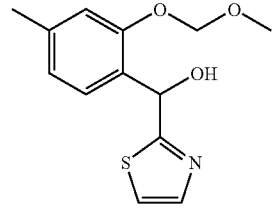

To a cooled (0° C.) solution of t-BuLi (1.7 M in pentane, 5.0 mL, 8.5 mmol), 1-(methoxymethoxy)-3-methylbenzene (see example 33, step 1) was added dropwise (1.18 g, 7.73 mmol), maintaining the internal temperature below 16° C. The suspension was stirred at 0° C. for 1 h, cooled to −78° C., and THF (15 mL) was added. A solution of 1,3-thiazole-2-carboxaldehyde (0.962 g, 8.5 mmol) was added and the cooling bath was removed. The reaction mixture was allowed to warm to 0° C., extracted twice with EtOAc from NH₄Cl, dried over MgSO₄, filtered and concentrated in vacuo. The residue was purified by flash chromatography (30-50% EtOAc in hexanes) to afford the title compound. ¹H NMR (400 MHz, acetone-d₆): 7.77 (d, 1H), 7.48 (s, 1H), 7.33 (d, 1H), 6.95 (s, 1H), 6.83 (d, 1H), 6.36 (d, 1H), 5.32 (d, 1H), 5.21 (s, 2H), 3.38 (s, 3H), 2.32 (s, 3H).

Step 2: [2-(methoxymethoxy)-4-methylphenyl](1,3-thiazol-2-yl)methanone

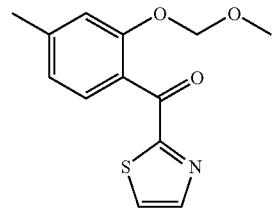

A mixture of [2-(methoxymethoxy)-4-methylphenyl](1,3-thiazol-2-yl)methanol from step 1 (3.6 g, 13.7 mmol) and MnO₂ (8.28 g, 95.2 mmol) in dichloromethane was stirred at room temperature overnight, filtered, and the insoluble material washed well with boiling EtOAc. The filtrates were combined and concentrated in vacuo to afford the title compound. ¹H NMR (400 MHz, acetone-d₆): 8.07-8.03 (m, 2H), 7.50 (d, 1H), 7.10 (s, 1H), 6.95 (d, 1H), 5.11 (s, 2H), 3.34 (s, 3H), 2.41 (s, 3H).

Step 3: (2-hydroxy-4-methylphenyl)(1,3-thiazol-2-yl)methanone

Prepared according to the general procedure for MOM-ether deprotection (example 33, step 3). ¹H NMR (400 MHz, acetone-d₆): 12.25 (s, 1H), 9.17 (d, 1H), 8.23 (s, 1H), 8.17 (s, 1H), 6.90-6.85 (m, 2H), 2.42 (s, 3H).

Step 4: 7-methyl-4-(1,3-thiazol-2-yl)-2H-chromen-2-one

Prepared according to the general procedure for coumarin formation (example 33, step 4). ¹H NMR (400 MHz, acetone-d₆): 8.58 (d, 1H), 8.18 (d, 1H), 8.00 (d, 1H), 7.27-7.23 (m, 2H), 6.77 (s, 1H), 2.47 (s, 3H).

Step 5: 7-(azidomethyl)-4-(1,3-thiazol-2-yl)-2H-chromen-2-one

Prepared according to the general procedure for azide formation (example 33, step 5). ¹H NMR (400 MHz, acetone-d₆): 8.78 (d, 1H), 8.24 (s, 1H), 8.03 (s, 1H), 7.48-7.44 (m, 2H), 6.84 (s, 1H), 4.67 (s, 2H).

Step 6: (S)-7-({4-[1-hydroxy-1-(trifluoromethyl)propyl]-1H-1,2,3-triazol-1-yl}methyl)-4-(1,3-thiazol-2-yl)-2H-chromen-2-one The title compound was prepared according to the general procedure for cycloaddition and deprotection (example 1, steps 8-9). The crude cycloaddition product was not purified, but was deprotected directly. MS (–APCI): 435 (M–H)⁻.

EXAMPLE 35

(S)-7-({4-[1-hydroxy-1-(trifluoromethyl)propyl]-1H-1,2,3-triazol-1-yl}methyl)-4-(3-methoxy-isoxazol-5-yl)-2H-chromen-2-one

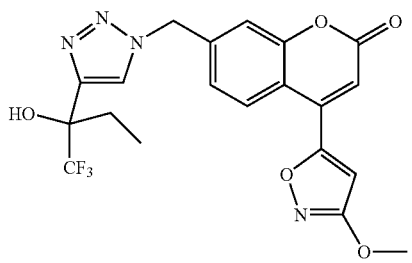

Step 1: (3-methoxylisoxazol-5-yl)[2-(methoxymethoxy)-4-methylphenyl]methanone

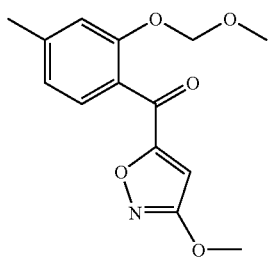

Prepared according to the general procedure for MOM ether ortho-lithiation and alkylation (example 33, steps 1-2), but using

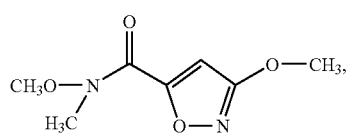

which was prepared using the general procedure described in Example 36, step 1. $^1$H NMR (400 MHz, acetone-$d_6$): 7.43 (d, 1H), 7.13 (s, 1H), 6.96 (d, 1H), 6.64 (s, 1H), 5.17 (s, 2H), 4.01 (s, 3H), 3.38 (s, 1H), 2.40 (s, 3H).

Step 2: (2-hydroxy-4-methylphenyl)(3-methoxyisoxazol-5-yl)methanone

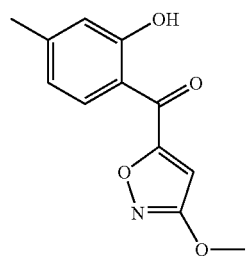

Prepared according to the general procedure for MOM ether deprotection (example 33, step 3). $^1$H NMR (400 MHz, acetone-$d_6$): 11.68 (s, 1H), 8.12 (d, 1H), 6.94-6.90 (m, 3H), 4.05 (s, 3H), 2.43 (s, 3H).

Step 3: 4-(3-methoxyisoxazol-5-yl)-7-methyl-2H-chromen-2-one

Prepared according to the general procedure for coumarin formation (example 33, step 4). $^1$H NMR (400 MHz, acetone-$d_6$): 7.96 (d, 1H), 7.30-7.26 (m, 2H), 6.90 (s, 1H), 6.73 (s, 1H), 4.06 (s, 3H), 2.50 (s, 3H).

Step 4: (S)-7-({4-[1-hydroxy-1-(trifluoromethyl)propyl]-1H-1,2,3-triazol-1-yl}methyl)-4-(3-methoxyisoxazol-5-yl)-2H-chromen-2-one Prepared according to the general procedure for azide formation, cycloaddition, and ester deprotection (example 33, steps 5-6), without isolation of intermediates. MS (–APCI): 449 (M–H)⁻.

EXAMPLE 36

(S)-7-[4-(1-Hydroxy-1-trifluoromethyl-propyl)-[1,2,3]triazol-1-ylmethyl]-4-isothiazol-5-yl-chromen 2-one

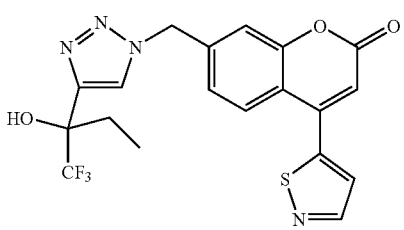

Step 1: N-methoxy-N-methylisothiazole-5-carboxamide

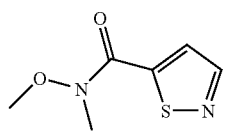

To a solution of 5-isothiazole carboxylic acid (5 g, 38.7 mmol) in dichloromethane (200 mL), 4-(dimethylamino)pyridine (473 mg, 3.87 mmol), N,O-dimethylhydroxylamine hydrochloride (4.53 g, 46.4 mmol) (N-(3-dimethylaminopropyl)-N'-ethyl-carbodiimide hydrochloride (8.17 g, 42.6 mmol) and triethylamine (13.63 µL, 97.0 mmol) were added and the reaction was stirred overnight at room temperature.

The reaction mixture was then successively washed with 1N HCl, 1N NaOH and brine. The organic layer was dried over MgSO$_4$, filtered and concentrated under reduced pressure. The crude residue obtained was used as such for the next step. $^1$H NMR (400 MHz, acetone-d$_6$): 8.59 (s, 1H), 7.97 (s, 1H), 3.94 (s, 3H), 3.38 (s, 3H).

Step 2: (S)-7-[4-(1-Hydroxy-1-trifluoromethyl-propyl)-[1,2,3]triazol-1-ylmethyl]-4-isothiazol-5-yl-chromen-2-one The title compound was prepared according to the procedures in example 33, starting from 1-(methoxymethoxy)-3-methylbenzene and N-methoxy-N-methylisothiazole-5-carboxamide. $^1$H NMR (400 MHz, acetone-d$_6$): 8.72 (s, 1H), 8.23 (s, 1H), 7.82 (s, 1H), 7.78 (d, 1H), 7.44 (s, 1H), 7.35 (d, 1H), 6.53 (s, 1H), 5.88 (s, 2H), 5.46 (s, 1H), 2.40-2.30 (m, 1H), 2.10-2.0 (m, 1H), 0.85 (t, 3H).

EXAMPLE 37

(S)-7-({4-[1-hydroxy-1-(trifluoromethyl)propyl]-1H-1,2,3-triazol-1-yl}methyl)-4-(2-methyl-1,3-oxazol-4-yl)-2H-chromen-2-one

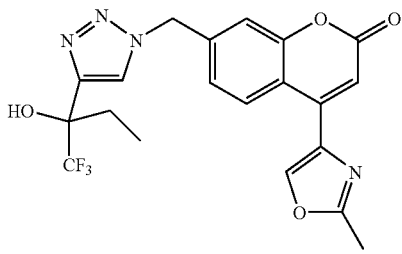

Step 1: 4-(1-ethoxyvinyl)-7-methyl-2H-chromen-2-one

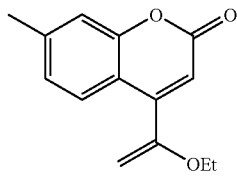

To a solution of 7-methyl-2-oxo-2H-chromen-4-yl trifluoromethanesulfonate (prepared as described in U.S. Pat. No. 5,552,437) (2.5 g, 8.1 mmol) and tributyl(1-ethoxyvinyl)tin (2.88 mL, 8.5 mmol) in 1,4-dioxane (25 mL), lithium chloride (1.03 g, 24.3 mmol) was added. The reaction flask was then purged twice with nitrogen and tetrakis(triphenylphosphine)palladium(0) (468 mg, 0.405 mmol) was added. The reaction was then heated overnight at 100° C. After cooling, the reaction mixture was concentrated under reduced pressure and the crude residue obtained was diluted with ethyl acetate, washed with a saturated ammonium chloride aq. solution, water and brine, dried over MgSO$_4$, filtered and concentrated. The crude residue obtained was purified by column chromatography (EtOAc/hexanes, 25:75 to 40:60) to afford the title compound. $^1$H NMR (400 MHz, acetone-d$_6$): 7.76 (d, 1H), 7.22 (s, 1H), 7.19 (d, 1H), 6.35 (s, 1H), 4.64 (d, 1H), 4.61 (d, 1H), 4.04 (q, 2H), 2.47 (s, 3H), 1.40 (t, 3H).

Step 2: 4-(bromoacetyl)-7-methyl-2H-chromen-2-one

To a solution of 4-(1-ethoxyvinyl)-7-methyl-2H-chromen-2-one (1.56 g, 6.77 mmol) in THF-water (27.5 mL, 10/1 mixture), N-bromosuccinimide (1.33 g, 7.45 mmol) was added. The reaction was then stirred at room temperature. After 3 hours stirring, toluene was added and the crude mixture was evaporated under reduced pressure. The crude residue obtained was purified by column chromatography (EtOAc/hexanes, 30:70) to afford the title compound. $^1$H NMR (400 MHz, acetone-d$_6$): 7.71 (d, 1H), 7.24 (s, 1H), 7.22 (d, 1H), 6.94 (s, 1H), 4.90 (s, 2H), 2.50 (s, 3H).

Step 3: 7-methyl-4-(2-methyl-1,3-oxazol-4-yl)-2H-chromen-2-one

To a solution of 4-(bromoacetyl)-7-methyl-2H-chromen-2-one (750 mg, 2.67 mmol) in N,N-dimethylformamide (2.5 mL), acetamide (158 mg, 2.67 mmol) was added. The reaction was then stirred overnight at 100° C. After cooling, the reaction mixture was dissolved with ethyl acetate and washed with water and brine, dried over MgSO$_4$, filtered and concentrated. The crude residue obtained was pre-adsorbed on silica gel and purified by column chromatography (EtOAc/hexanes, 30:70 to 80:20) to afford the title compound. $^1$H NMR (400 MHz, acetone-d$_6$): 8.52 (s, 1H), 8.21 (d, 1H), 7.23 (s, 1H), 7.21 (d, 1H), 6.52 (s, 1H), 2.57 (s, 3H), 2.49 (s, 3H).

Step 4: 7-(bromomethyl)-4-(2-methyl-1,3-oxazol-4-yl)-2H-chromen-2-one

The title compound was prepared following the general bromide preparation procedure (example 33, step 5). $^1$H NMR (400 MHz, acetone-d$_6$): 8.65 (s, 1H), 8.36 (d, 1H), 7.52-7.44 (m, 2H), 6.78 (s, 1H), 4.78 (s, 2H), 2.57 (s, 3H).

Step 5: 7-(azidomethyl)-4-(2-methyl-1,3-oxazol-4-yl)-2H-chromen-2-one

The title compound was prepared following the general azide preparation procedure (example 33, step 5). $^1$H NMR (400 MHz, acetone-d$_6$): 8.66 (s, 1H), 8.39 (d, 1H), 7.50-7.40 (m, 2H), 6.78 (s, 1H), 4.66 (s, 2H), 2.59 (s, 3H).

Step 6: (S)-1-(1-{[4-(2-methyl-1,3-oxazol-4-yl)-2-oxo-2H-chromen-7-yl]methyl}-1H-1,2,3-triazol-4-yl)-1-(trifluoromethyl)propyl 4-nitrobenzoate The title compound was prepared using 1-ethyl-1-(trifluoromethyl)prop-2-yn-1yl 4-nitrobenzoate (see example 1, step 2) by following the general triazole formation procedure (example 1, step 8). $^1$H NMR (400 MHz, acetone-d$_6$): 8.62 (s, 1H), 8.48 (s, 1H), 8.44 (d, 2H), 8.35-8.25 (m, 3H), 7.32-7.28 (m, 2H), 6.74 (s, 1H), 5.86 (s, 2H), 3.10-3.0 (m, 1H), 2.90-2.80 (m, 1H), 2.55 (s, 3H), 1.14 (t, 3H).

Step 7: (S)-7-({4-[1-hydroxy-1-(trifluoromethyl)propyl]-1H-1,2,3-triazol-1-yl}methyl)-4-(2-methyl-1,3-oxazol-4-yl)-2H-chromen-2-one The title compound was prepared following the general deprotection procedure (example 1, step 9). $^1$H NMR (400 MHz, acetone-d$_6$): 8.64 (s, 1H), 8.40 (d, 1H), 8.22 (s, 1H), 7.39 (s, 1H), 7.34 (d, 1H), 6.67 (s, 1H), 5.87 (s, 2H), 5.47 (s, 1H), 2.57 (s, 3H), 2.40-2.30 (m, 1H), 2.10-2.0 (m, 1H), 0.85 (t, 3H).

EXAMPLE 38

(S)-7-({4-[1-hydroxy-1-(trifluoromethyl)propyl]-1H-1,2,3-triazol-1-yl}methyl)-4-(2-methyl-1,3-thiazol-4-yl)-2H-chromen-2-one

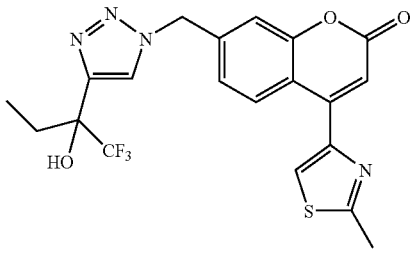

Step 1: 7-bromo-4-(1-ethoxyvinyl)-2H-chromen-2-one

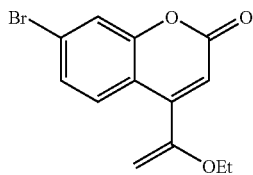

To a solution of 7-bromo-2-oxo-2H-chromen-4-yl trifluoromethanesulfonate (prepared as described in U.S. Pat. No. 5,552,437) (5 g, 13.4 mmol) and tributyl(1-ethoxyvinyl)tin (4.75 mL, 14.1 mmol) in 1,4-dioxane (50 mL), lithium chloride (1.7 g, 40.2 mmol) was added. The reaction flask was then purged twice with nitrogen and tetrakis(triphenylphosphine) palladium(0) (774 mg, 0.7 mmol) was added. The reaction was then heated 4 hours at 80° C. After cooling, the reaction mixture was concentrated under reduced pressure and the crude residue obtained was diluted with ethyl acetate, washed with a saturated ammonium chloride aq. solution, water and brine, dried over MgSO$_4$, filtered and concentrated. The crude residue obtained was purified by column chromatography (hexanes/CH$_2$Cl$_2$/acetone, 25:75:0 to 0:95:5) to afford the title compound. $^1$H NMR (400 MHz, acetone-d$_6$): 7.83 (d, 1H), 7.60 (s, 1H), 7.52 (d, 1H), 6.46 (s, 1H), 4.67 (s, 2H), 4.05 (q, 2H), 1.38 (t, 3H).

Step 2: 7-bromo-4-(bromoacetyl)-2H-chromen-2-one

To a solution of 7-bromo-2-oxo-2H-chromen-4-yl trifluoromethanesulfonate (2.71 g, 9.35 mmol) in THF-water (40 mL, 10/1 mixture), N-bromosuccinimide (1.83 g, 10.3 mmol) was added. The reaction was then stirred at room temperature. After 5 hours stirring, toluene was added and the crude mixture was evaporated under reduced pressure. The crude residue obtained was purified by column chromatography (EtOAc/hexanes, 25:75) to afford the title compound. $^1$H NMR (400 MHz, acetone-d$_6$ 7.80 (d, 1H), 7.72-7.62 (m, 1H), 7.60 (d, 1H), 7.13 (s, 1H), 4.92 (s, 2H).

Step 3: 7-bromo-4-(2-methyl-1,3-thiazol-4-yl)-2H-chromen-2-one

To a solution of 7-bromo-4-(bromoacetyl)-2H-chromen-2-one (1.45 g, 4.19 mmol) in N,N-dimethylformamide (12.5 mL), thioacetamide (346 mg, 4.6 mmol) was added. The reaction was then stirred overnight at 100° C. After cooling, the reaction mixture was dissolved with a 4:1 mixture of CH$_2$Cl$_2$/hexanes. The mixture obtained was washed (3×) with water and the organic layer was concentrated under reduced pressure. The solid obtained was swished in a 4:1 mixture of hexanes/EtOAc. The solid obtained was collected by filtration and used as such for the next step. $^1$H NMR (400 MHz, acetone-d$_6$): 8.32 (d, 1H), 8.14 (s, 1H), 7.66 (s, 1H), 7.54 (d, 1H), 6.73 (s, 1H), 2.74 (s, 3H).

Step 4: 7-methyl-4-(2-methyl-1,3-thiazol-4-yl)-2-oxo-2H-chromene-7-carboxylate To a solution of 7-bromo-4-(2-methyl-1,3-thiazol-4-yl)-2H-chromen-2-one (1.3 g, 4.04 mmol) in DMSO-MeOH (45 mL, 2:1 mixture), triethylamine (1.14 mL, 8.08 mmol) was added. The reaction flask was purged twice with carbon monoxide and palladium (II) dichloride (dppf)-CH$_2$Cl$_2$ (660 mg, 0.81 mmol) was added. The mixture was then heated at 65° C. overnight under a carbon monoxide atmosphere. After cooling, the reaction mixture was diluted with ethyl acetate, washed with water (3×) and brine, dried over MgSO$_4$, filtered and concentrated. The crude residue obtained was purified by column chromatography (acetone/CH$_2$Cl$_2$, 5:95) to afford the title compound. $^1$H NMR (400 MHz, acetone-d$_6$): 8.45 (d, 1H), 8.15 (s, 1H), 7.92 (d, 1H), 7.91 (s, 1H), 6.81 (s, 1H), 3.97 (s, 3H), 2.84 (s, 3H).

Step 5: 4-(2-methyl-1,3-thiazol-4-yl)-2-oxo-2H-chromene-7-carboxylic acid

To a solution of 7-methyl-4-(2-methyl-1,3-thiazol-4-yl)-2-oxo-2H-chromene-7-carboxylate (840 mg, 2.79 mmol) in THF (40 mL) a solution of lithium hydroxide (14 mL, 14.0 mmol) was added. The solution was then heated at 65° C. for 1.5 hours. After cooling, THF was removed under reduced pressure and 2N HCl (8.6 mL, 17.2 mmol) was added. After 1 h stirring, the solid formed was collected by filtration to afford the title compound. $^1$H NMR (400 MHz, DSMO-d$_6$): 13.6 (bs, 1H), 8.40 (d, 1H), 8.32 (s, 1H), 7.91 (d, 1H), 7.89 (s, 1H), 6.86 (s, 1H), 2.82 (s, 3H).

Step 6: 7-(hydroxymethyl)-4-(2-methyl-1,3-thiazol-4-yl)-2H-chromen-2-one

To a solution of 4-(2-methyl-1,3-thiazol-4-yl)-2-oxo-2H-chromene-7-carboxylic acid (250 mg, 0.87 mmol) in THF (10 mL) triethylamine (0.31 mL, 2.18 mmol) was added. The mixture was stirred until it became a clear solution. The reaction was then cooled to 0° C. and isobutylchloroformate was added dropwise (230 uL, 1.74 mmol). After 1 hour stirring at 0° C. a solution of sodium borohydride in water (132 mg, 3.48 mmol in 3.5 mL) was added slowly and the mixture was stirred for another hour. The reaction mixture was quenched with a saturated ammonium chloride solution and the product was extracted with ethyl acetate. The combined organic extracts were washed with water and brine, dried over MgSO$_4$, filtered and concentrated under reduced pressure. The crude residue obtained was used as such for the next step. $^1$H NMR (400 MHz, acetone-d$_6$): 8.26 (d, 1H), 8.07 (s, 1H), 7.42 (s, 1H), 7.35 (d, 1H), 6.64 (s, 1H), 4.80 (d, 2H), 4.56 (t, 1H), 2.85 (s, 3H).

Step 7: 7-(azidomethyl)-4-(2-methyl-1,3-thiazol-4-yl)-2H-chromen-2-one

To a suspension of 7-(hydroxymethyl)-4-(2-methyl-1,3-thiazol-4-yl)-2H-chromen-2-one (155 mg, 0.57 mmol), in toluene (5 mL), triphenylphosphine (297 mg, 1.13 mmol) and Zn(N$_3$)$_2$.2 pyridine (prepared as described in Synthesis, 1990, p. 130-132) (131 mg, 0.43 mmol) were added. After 10 minutes stirring, N,N-diisopropylazodicarboxylate (220 uL, 1.13 mmol) was added dropwise. The reaction was then stirred overnight at room temperature. The reaction mixture was concentrated under reduced pressure and the crude residue obtained was purified by column chromatography (acetone/CH$_2$Cl$_2$, 5:95) to afford the title compound. $^1$H NMR (400 MHz, acetone-d$_6$): 8.34 (d, 1H), 8.11 (s, 1H), 7.48 (s, 1H), 7.40 (d, 1H), 6.70 (s, 1H), 4.65 (s, 2H), 2.82 (s, 3H).

Step 8: (S)-1-(1-{[4-(2-methyl-1,3-thiazol-4-yl)-2-oxo-2H-chromen-7-yl]methyl}-1H-1,2,3-triazol-4-yl)-1-(trifluoromethyl)propyl 4-nitrobenzoate The title compound was prepared using 1-ethyl-1-(trifluoromethyl)prop-2-yn-1yl 4-nitrobenzoate (see example 1, step 2) by following the general triazole formation procedure (example 1, step 8). $^1$H NMR (400 MHz, acetone-d$_6$): 8.5 (s, 1H), 8.44 (d, 2H), 8.35-8.25 (m, 3H), 8.11 (s, 1H), 7.35-7.25 (m, 2H), 6.71 (s, 1H), 5.87 (s, 2H), 3.10-3.0 (m, 1H), 2.90-2.80 (m, 1H), 2.85 (s, 3H), 1.14 (t, 3H).

Step 9: (S)-7-({4-[1-hydroxy-1-(trifluoromethyl)propyl]-1H-1,2,3-triazol-1-yl}methyl)-4-(2-methyl-1,3-thiazol-4-yl)-2H-chromen-2-one The title compound was prepared following the general deprotection procedure (example 1, step 9). $^1$H NMR (400 MHz, acetone-d$_6$): 8.34 (d, 1H), 8.22 (d, 1H), 8.11 (s, 1H), 7.40 (s, 1H), 7.32 (d, 1H), 6.71 (s, 1H), 5.87 (s, 2H), 5.49 (s, 1H), 2.85 (s, 3H), 2.40-2.30 (m, 1H), 2.10-2.0 (m, 1H), 0.90-0.80 (t, 3H).

Quinoline Method A:

The 2,4,7-trisubstituted quinolines 9 are prepared according to procedures described in U.S. Pat. Nos. 5,552,437 and 5,576,338. For example, in U.S. Pat. No. 5,552,437 see Scheme 7 at columns 14, 15 and 26, and the preparation of 7-bromomethyl-2-cyano-4-(4-fluorophenyl)quinoline at column 72. The 7-methyl group is converted to the mono or dibromide intermediate with NBS and heating in an inert solvent such as $CCl_4$ in the presence of a radical initiator, such as benzoyl peroxide, AIBN, and light. The monobromide is treated with an azide salt in a solvent such as ethanol at elevated temperature to give the azide. The monobromide can also be treated with an excess of NMO at elevated temperatures in a solvent such as dioxane to afford the desired aldehyde. Alternatively, the dibromide can be reacted with $AgNO_3$ in aqueous dioxane at reflux also to afford the aldehyde. The aldehyde is reduced with sodium borohydride, or the like, in THF and methanol to give the primary alcohol. The alcohol is converted to an azide with triphenylphosphine, an activating agent such as diisopropyl azodicarboxylate and an azide source such as $Zn(N_3)_2 \cdot 2$ pyridine. The azide is then treated with an alkyne in presence of copper iodide and a base such as diisopropylethylamine to afford a triazole. If the alcohol is protected as an ester, it can be cleaved with a base such as lithium hydroxide in a solvent like THF to give the tertiary alcohol. The nitrile can be hydrolyzed with a strong acid like HCl to give a carboxylic acid, which can be further derivatized as desired.

Quinoline Scheme A:

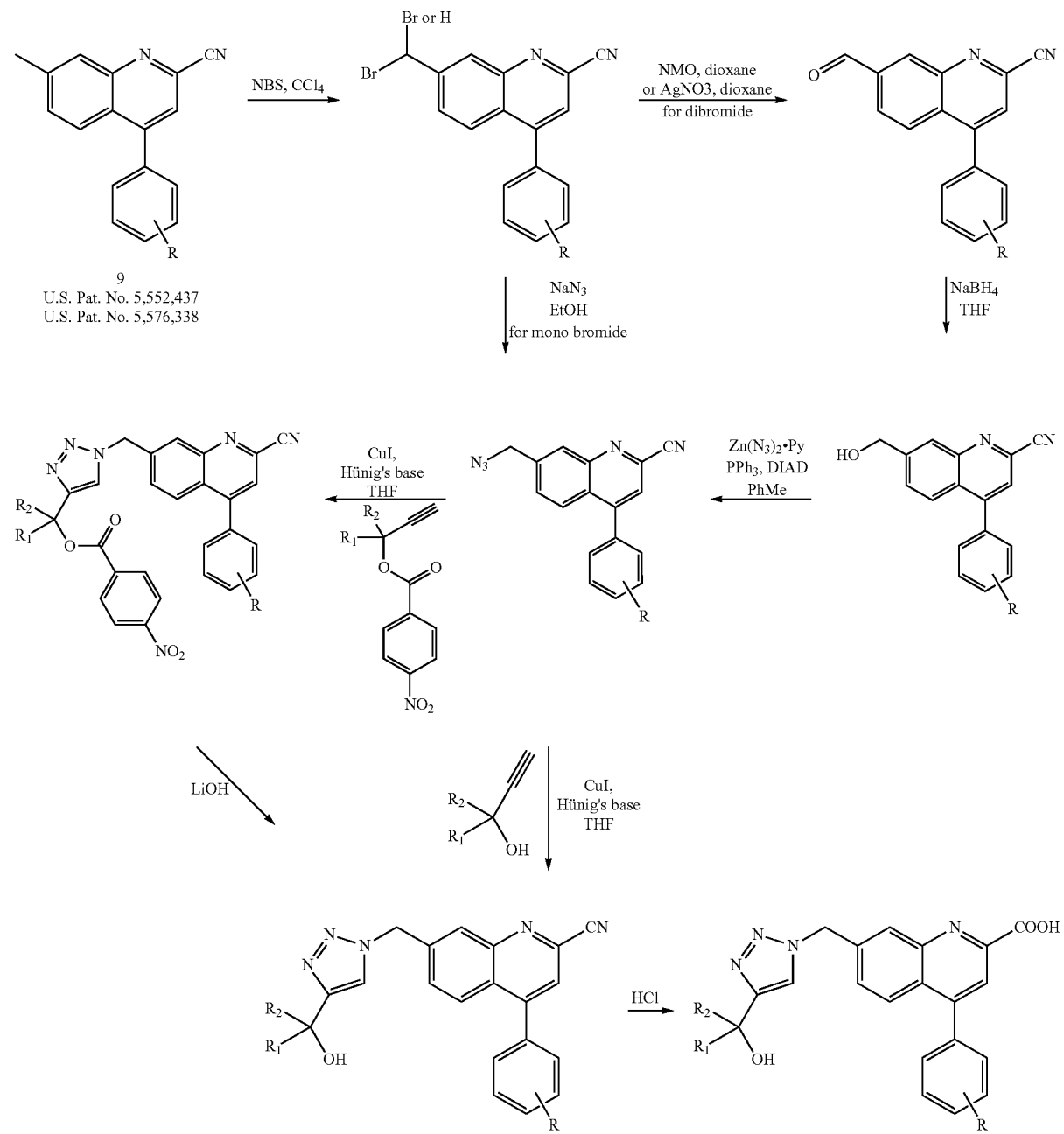

Quinoline Method B:

7-Methylquinoline is converted into 2-cyano-7-methylquinoline by treatment with an oxidizing reagent such as mCPBA in an organic solvent followed by reaction of the intermediate N-oxide with an acylating reagent such as dialkylcarbamyl chloride, and a cyanating agent such as trimethylsilyl cyanide. Oxidation with mCPBA to the N-oxide followed by treatment with an acylating agent such as phosphorus oxychloride at elevated temperature affords the trisubstituted chloroquinoline. Bromination is achieved upon treatment with a bromide source such as NBS and benzoyl peroxide. The bromide is then displaced with a nucleophile such as sodium azide in an organic solvent such as ethanol. The azide is treated with an alkyne in presence of copper iodide and a base such as diisopropylethylamine to afford the triazole. Coupling of the latter with a metalated reagent such as tributyl(1-ethoxyvinyl)tin and a catalyst such as $Pd(PPh_3)_4$ under Stille coupling conditions introduces the ethoxyvinyl substituent. Bromination is achieved upon treatment with a bromide source such as NBS. The bromo ketone can be converted to a heterocycle by treatment with a nucleophile such as acetamide in a polar solvent like DMF at elevated temperature. The ester is hydrolyzed to the tertiary alcohol with a base such as lithium hydroxide in a solvent like THF.

Quinoline Scheme B:
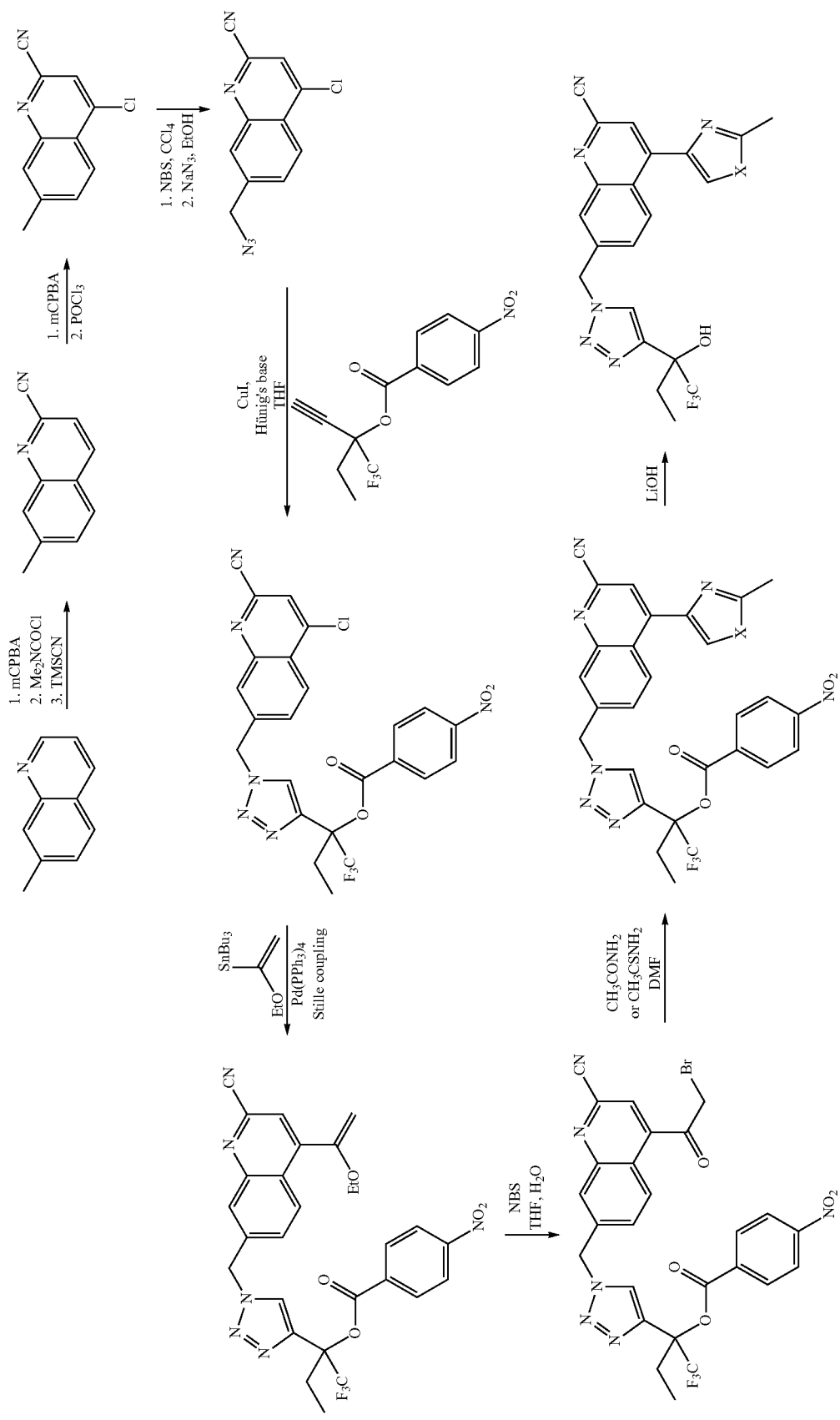

Quinoline Method C:

The 4-chloroquinoline derivative from quinoline method B can be treated with a variety of boronic acids or the like under standard aqueous Suzuki conditions followed by hydrolysis to give the desired tertiary alcohol. Alternatively, the 4-chloroquinoline derivative can be treated with a base such as lithium hydroxide in a solvent like THF to give the tertiary alcohol first which is then treated with a variety of boronic acids or the like under standard aqueous Suzuki conditions the give the desired product.

Quinoline Scheme C:

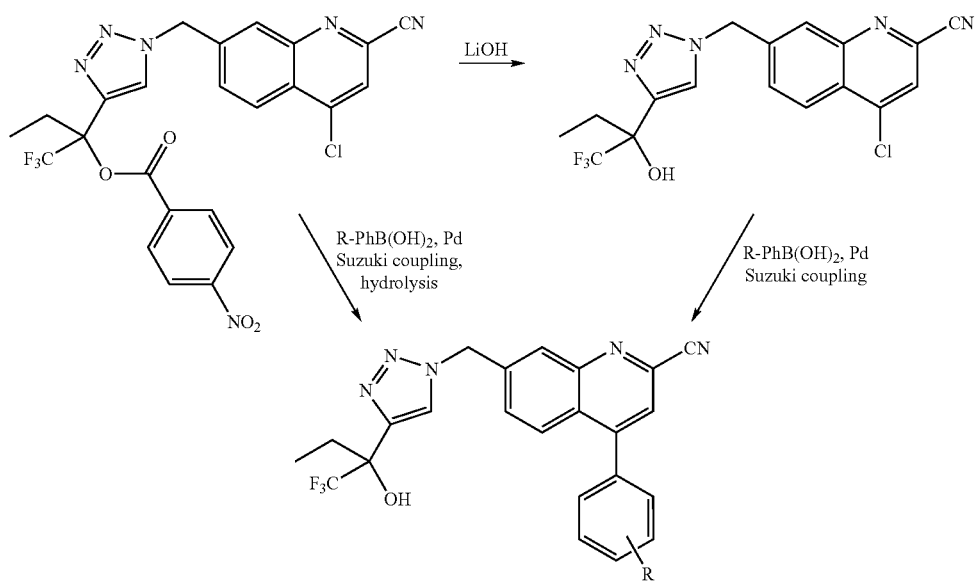

Quinoline Method D:

The 2-cyanoquinoline derivatives from quinoline methods A-C can be hydrolyzed with sodium carbonate and hydrogen peroxide to give the desired amide.

Quinoline Scheme D:

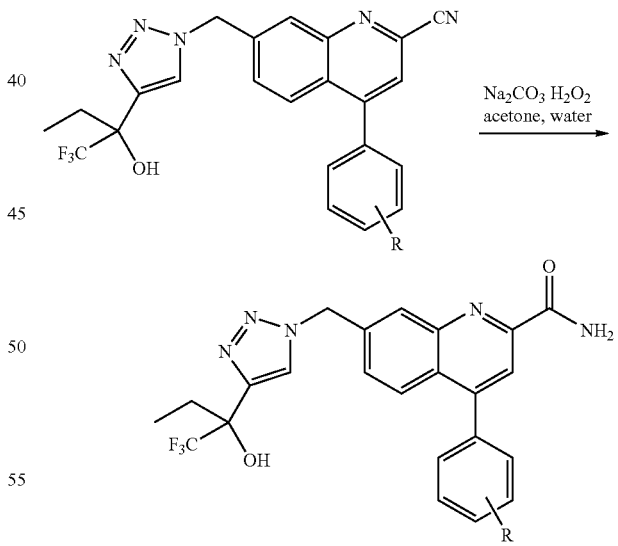

Quinoline Method E:

The trisubstituted chloroquinoline can be prepared via oxidation of the disubstituted quinoline followed by treatment with $POCl_3$. Standard transformations as described in the previous method (i.e. NBS bromination, azide and triazole formation, followed by ester hydrolysis) give the tertiary alcohol. The chloride is then displaced with a variety of nucleophiles, including (but not limited to) alcohols, amines, thiols, boronate reagents, tin reagents and Grignard reagents, in solvents like THF, DMF, and NMP.

Quinoline Scheme E:

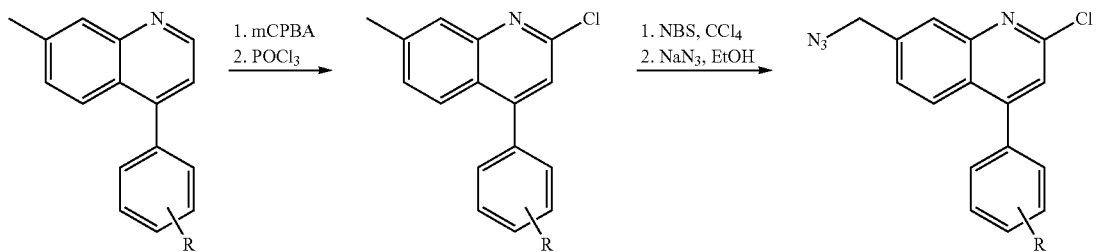

U.S. Pat. No. 5,552,437
U.S. Pat. No. 5,576,338

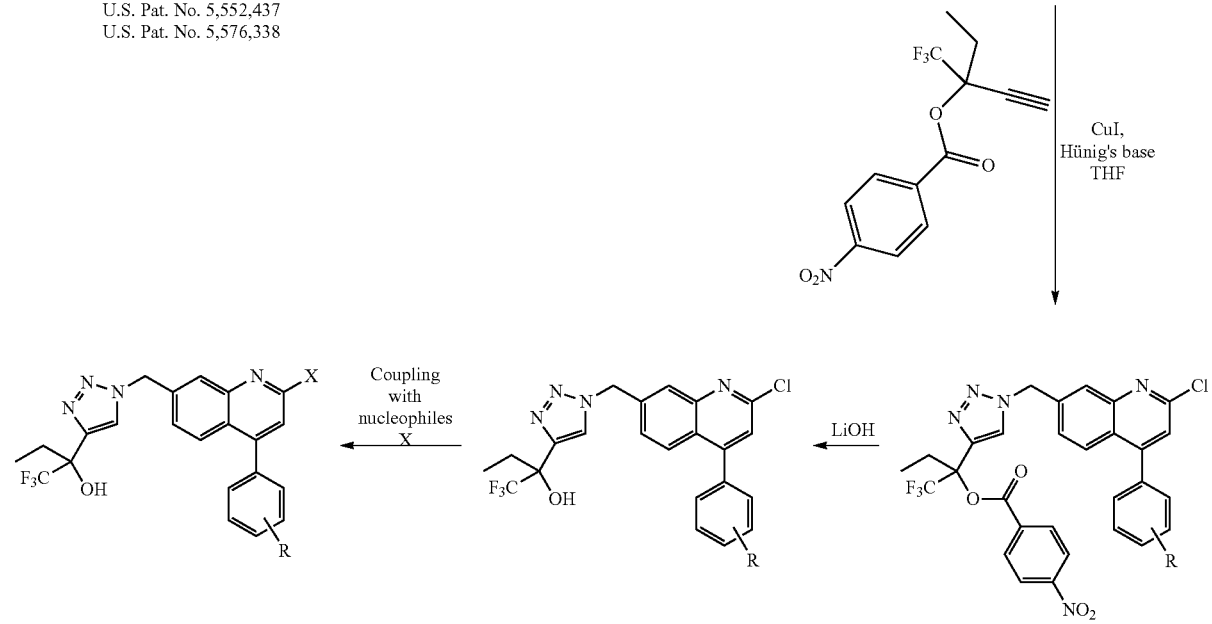

Quinoline Method F:

The methylketone is synthesized as described in quinoline method D. Addition of hydride, Grignard reagents or the like at low temperature affords alcohols. The alcohol is alkylated with an alkylating agent like MeI in presence of a base such as NaH to give an ether. Alternatively, the methylketone can be treated with an amine such as hydroxylamine in pyridine or other organic solvents and a base to give hydroximine derivatives.

Quinoline Scheme F:

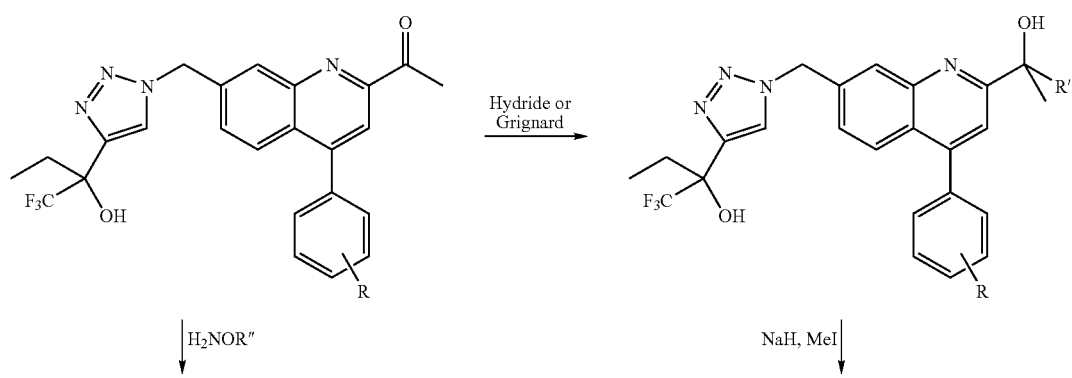

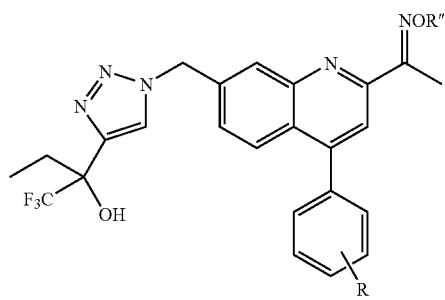
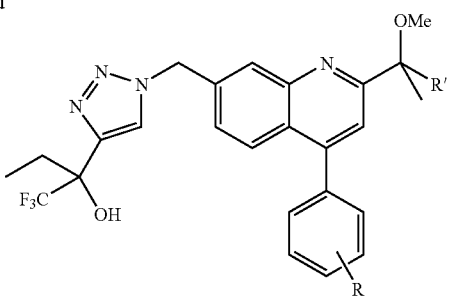

-continued

Quinoline Method G:

The chloroquinoline derivative is prepared according to procedures described in U.S. Pat. Nos. 5,552,437 and 5,576,338 for the corresponding methyl derivative. The 7-chloro group is converted to allyl intermediate with allyltributyltin under palladium catalysis and heating in an inert solvent such as toluene or dioxane. The alkene is treated with ozone and a reducing agent such as methyl sulphide to give the aldehyde. The aldehyde is reduced with sodium borohydride, or the like, in THF and methanol to give the primary alcohol. The alcohol is converted to an azide with triphenylphosphine, an activating agent such as diisopropyl azodicarboxylate and an azide source such as $Zn(N_3)_2 \cdot 2$ pyridine. The azide is then treated with an alkyne in presence of copper iodide and a base such as diisopropylethylamine to afford a triazole. If the alcohol is protected as an ester, it can be cleaved with a base such as lithium hydroxide in a solvent like THF to give the tertiary alcohol.

EXAMPLE 39

(S)-7-({4-[1-hydroxy-1-(trifluoromethyl)propyl]-1H-1,2,3-triazol-1-yl}methyl)-4-phenylquinoline-2-carbonitrile

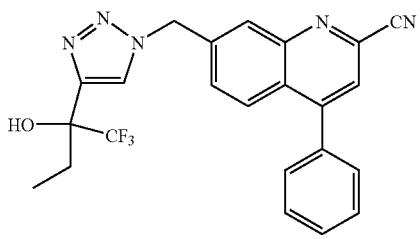

Step 1: 7-Chloro-4-phenylquinoline

A mixture of 4,7-dichloroquinoline (12.5 g, 63.1 mmol), phenylboronic acid (9.63 g, 79 mmol) and cesium fluoride (24 g, 158 mmol) in 1,2-dimethoxyethane (300 mL) was degassed and purged three times with nitrogen gas before the Quinoline Scheme G:

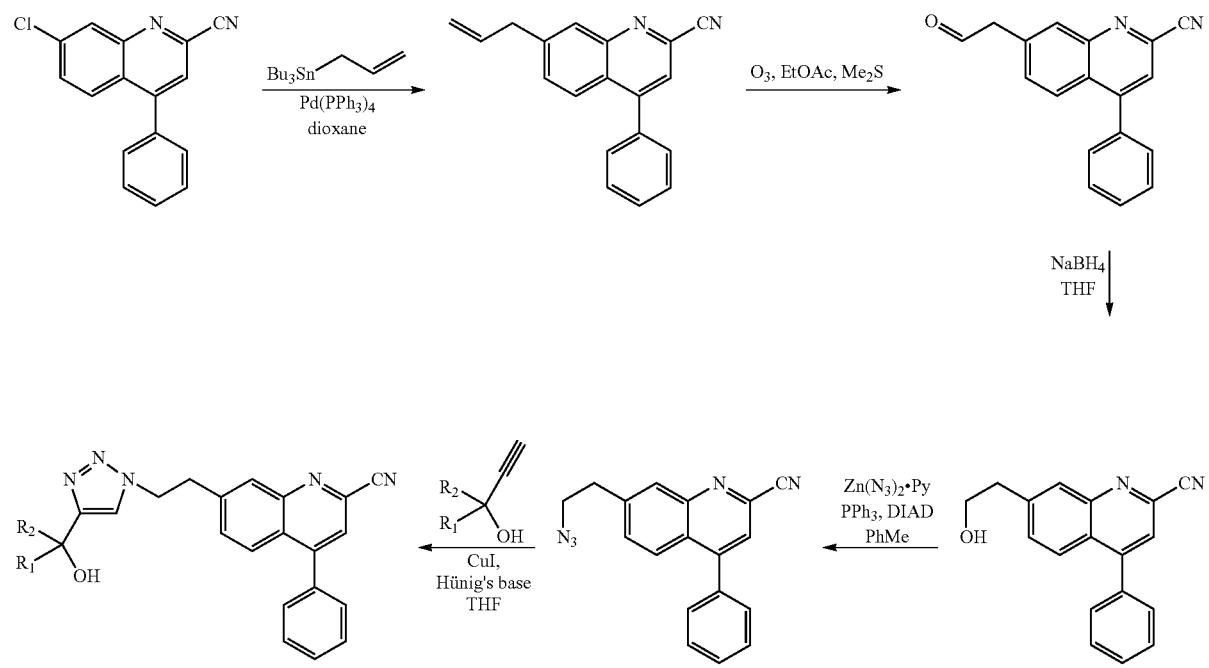

addition of the tetrakis(triphenylphosphine) palladium(0) (3.64 g, 3.15 mmol). The resultant mixture was then stirred at reflux overnight. After cooling, the reaction was filtered over celite and washed with dichloromethane. After evaporation under reduced pressure, the residue was purified by column chromatography (eluting with hexane/EtOAc, 95:5) to yield the title compound. $^1$H NMR (400 MHz, acetone-d$_6$): δ 9.0 (d, 1H), 8.15 (d, 1H), 7.95 (d, 1H), 7.65-7.55 (m, 6H), 7.5 (d, 1H).

Step 2: 7-Methyl-4-phenylquinoline

To a solution of 7-chloro-4-phenylquinoline (10.0 g, 41.7 mmol) and Ni(dppp)$_2$Cl$_2$ (2.26 g, 4.17 mmol) in ether (200 mL) was added dropwise 3.0 M MeMgBr (24.3 mL, 73 mmol) and heated at reflux for 3 h. The reaction mixture was quenched with saturated aqueous NH$_4$Cl solution and extracted with ether. The combined organic layer was washed with water and brine and then dried over anhydrous MgSO$_4$. The solvent was removed under reduced pressure, and the resulting crude product was used in the next step without further purification. $^1$H NMR (400 MHz, acetone-d$_6$): δ 8.9 (d, 1H), 7.93 (bs, 1H), 7.82 (d, 1H), 7.52-7.62 (m, 5H), 7.43 (dd, 1H), 7.35 (d, 1H), 2.60 (S, 3H).

Step 3: 7-Methyl-4-phenylquinoline-2-carbonitrile

A solution of 7-methyl-4-phenylquinoline (10.0 g, 41.7 mmol) and m-CPBA (13.5 g, 54.8 mmol) in chloroform (230 mL) was stirred at room temperature for 3 h. The reaction was quenched with saturated aqueous NaHCO$_3$ solution and extracted twice with dichloromethane. The combined organic layers were washed with water, brine, and dried over anhydrous MgSO$_4$. The solvent was removed under reduced pressure and the resulting crude product was dissolved in chloroform (220 mL). N,N-Dimethylcarbamoyl chloride (8.44 mL, 91.4 mmol) and trimethylsilyl cyanide (11.5 mL, 91.4 mmol) were added to this solution and stirred at room temperature for 2 d. Saturated aqueous NaHCO$_3$ solution was added and stirred for 30 min. The organic layer was removed, and the aqueous layer was extracted with dichloromethane. The combined organic layers were washed with water, brine, and dried over anhydrous MgSO$_4$. The solvent was removed under reduced pressure and the resulting crude product was used in the next step without further purification. $^1$H NMR (400 MHz, acetone-d$_6$): δ 8.01 (s, 1H), 7.92 (d, 1H), 7.80 (s, 1H), 7.60-7.67 (m, 6H), 2.63 (s, 3H).

Step 4: 7-(Bromomethyl)-4-phenylquinoline-2-carbonitrile

A solution of 7-methyl-4-phenylquinoline-2-carbonitrile (11.2 g, 41.7 mmol), N-bromo-succinimide (12.2 g, 68.6 mmol) and AIBN (2,2'-azobisisobutyronitrile) (200 mg) in carbon tetrachloride (200 mL) was heated at reflux overnight. The reaction was cooled to ambient temperature and the solid residue was filtered. The filtrate was concentrated under reduced pressure. The crude product was purified by flash column chromatography (eluting with 5% ethyl acetate in hexane) to give the title compound. $^1$H NMR (400 MHz, acetone-d$_6$): δ 8.30 (s, 1H), 8.06 (d, 1H), 7.90 (s, 1H), 7.87 (d, 1H), 7.6-7.7 (m, 5H), 4.95 (s, 2H).

Step 5: 7-(Dibromomethyl)-4-phenylquinoline-2-carbonitrile

A solution of 7-methyl-4-phenylquinoline-2-carbonitrile (2.0 g, 7.6 mmol), N-bromosuccinimide (2.7 g, 15.2 mmol) and AIBN (50 mg) in CCl$_4$ (40 mL) was stirred at reflux overnight. After cooling, the mixture was filtered and the solid collected was rinsed with CCl$_4$. The filtrate was concentrated under reduced pressure and the crude residue obtained was suspended overnight in a 10:1 mixture of hexanes and Et$_2$O to yield the title compound Step 6: 7-formyl-4-phenylquinoline-2-carbonitrile To a solution of 7-(dibromomethyl)-4-phenylquinoline-2-carbonitrile (2.02 g, 4.81 mmol) in 1,4-dioxane (75 mL) was added a solution of silver nitrate (3.27 g, 19.24 mmol) in 30 mL of water, and the reaction mixture stirred 1 h at reflux. After cooling to rt, the mixture was diluted with EtOAc and filtered. The solid was washed with EtOAc and the organic phases combined. The filtrate was washed twice with water and the combined aqueous layers were back-extracted twice with EtOAc. The combined organic extracts were washed with brine, dried over MgSO$_4$, filtered and concentrated. The crude residue obtained was purified by column chromatography (eluting with acetone-CH$_2$Cl$_2$-toluene, 10:40:50) to yield the title compound. $^1$H NMR (400 MHz, acetone-d$_6$): δ 10.39 (s, 1H), 8.80 (s, 1H), 8.21 (s, 2H), 8.07 (s, 1H), 7.66 (m, 5H).

Step 7: 7-(hydroxymethyl)-4-phenylquinoline-2-carbonitrile

To a solution of 7-formyl-4-phenylquinoline-2-carbonitrile (516 mg, 2.0 mmol) in THF (6 mL) and MeOH (2 mL) was added at 0° C. sodium borohydride (91 mg, 2.4 mmol). The mixture was stirred 1 h at 0° C., quenched with saturated aqueous NH$_4$Cl and extracted with EtOAc. The combined organic layers were washed with brine, dried over Na$_2$SO$_4$ and concentrated under reduced pressure. The compound was used as such for the next step. MS (+ESI): 262 (M+H)$^+$.

Step 8: 7-(azidomethyl)-4-phenylquinoline-2-carbonitrile

To a solution of 7-formyl-4-phenylquinoline-2-carbonitrile (520 mg, 2.0 mmol) in toluene (12 mL) was added triphenylphosphine (1.05 g, 4.0 mmol), Zn(N$_3$)$_2$.2 pyridine (461 mg, 1.5 mmol) and diisopropyl azodicarboxylate (787 µL, 4.0 mmol). The mixture was stirred at room temperature for 3 h, concentrated and purified on silica gel (eluting with EtOAc/hexanes, 3:7) to give the title compound. MS (+ESI): 286 (M+H)$^+$.

Step 9: (S)-1-{1-[(2-cyano-4-phenylquinolin-7-yl)methyl]-1H-1,2,3-triazol-4-yl}-1-(trifluoromethyl)propyl 4-nitrobenzoate To a solution of 7-(azidomethyl)-4-phenylquinoline-2-carbonitrile (120 mg, 0.42 mmol) and 1-ethyl-1-(trifluoromethyl)prop-2-yn-1-yl 4-nitrobenzoate (139 mg, 0.46 mmol, slower eluting enantiomer described in Example 1, step 2) in THF (5 mL) was added diisopropylethylamine (0.37 mL, 2.1 mmol) followed by copper iodide (120 mg, 0.63 mmol). The reaction was stirred at room temperature overnight and quenched with saturated aqueous NH$_4$Cl and extracted with EtOAc. The combined organic layers were washed with brine, dried over Na$_2$SO$_4$, filtered and concentrated under reduced pressure. Purification on silica gel (eluting with EtOAc/hexanes, 4:6) gave the title compound. MS (+ESI): 587 (M+H)$^+$.

Step 10: (S)-7-({4-[1-hydroxy-1-(trifluoromethyl)propyl]-1H-1,2,3-triazol-1-yl}methyl)-4-phenylquinoline-2-carbonitrile To a solution of (S)-1-{1-[(2-cyano-4-phenylquinolin-7-yl)methyl]-1H-1,2,3-triazol-4-yl}-1-(trifluoromethyl)propyl 4-nitrobenzoate (200 mg, 0.34 mmol) in THF (6 mL) was added lithium hydroxide IM (1.7 mL, 1.7 mmol). The mixture was stirred at room temperature for 1 h and quenched with saturated aqueous NH$_4$Cl and extracted with EtOAc. The combined organic layers were washed with brine, dried over Na$_2$SO$_4$, filtered and concentrated under reduced pressure. Purification on silica gel (eluting with acetone/dichloromethane, 1:9) gave the title compound. MS (+ESI): 438 (M+H)$^+$.

EXAMPLE 39A the general procedure of Example 39 was used to make 7-({4-[1-hydroxy-1-(trifluoromethyl)propyl]-1H-1,2,3-triazol-1-yl}methyl)-4-phenylquinoline-2-carbonitrile, except substituting racemic 1-ethyl-1-(trifluoromethyl)prop-2-yn-1-yl 4-nitrobenzoate in place of the enantiopure form.

Examples 40-41 were prepared using the general procedure described in Example 39, using the appropriated fluorophenylboronic acid and the slower eluting enantiomer of 1-ethyl-1-(trifluoromethyl)prop-2-yn-1-yl 4-nitrobenzoate described in Example 1, step 2.

EXAMPLE 40

(S)-4-(3-fluorophenyl)-7-({4-[1-hydroxy-1-(trifluoromethyl)propyl]-1H-1,2,3-triazol-1-yl}methyl)quinoline-2-carbonitrile

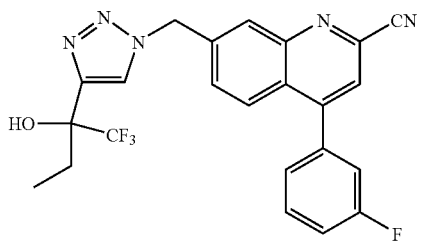

$^1$H NMR (400 MHz, acetone-$d_6$): 8.30 (s, 1H), 8.18 (d, 1H), 8.09 (d, 1H), 7.98 (s, 1H), 7.80 (d, 1H), 7.75-7.65 (m, 1H), 7.52-7.35 (m, 3H), 6.04 (s, 2H), 5.51 (s, 1H), 2.41-2.30 (m, 1H), 2.12-2.02 (m, 1H), 0.85 (t, 31H).

EXAMPLE 41

(S)-4-(4-fluorophenyl)-7-({4-[1-hydroxy-1-(trifluoromethyl)propyl]-1H-1,2,3-triazol-1-yl}methyl)quinoline-2-carbonitrile

MS (+ESI): 456 (M+H)$^+$.

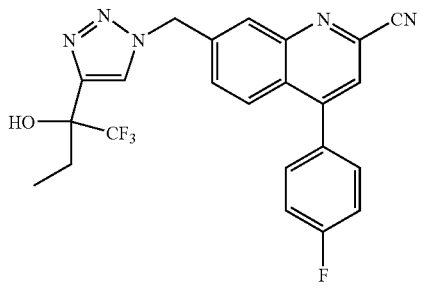

Examples 40A and 41A were prepared using the general procedures used to prepare Examples 40 and 41, respectively, except substituting racemic 1-ethyl-1-(trifluoromethyl)prop-2-yn-1-yl 4-nitrobenzoate in place of the enantiopure form.

EXAMPLE 42

(S)-7-({4-[1-hydroxy-1-(trifluoromethyl)propyl]-1H-1,2,3-triazol-1-yl}methyl)-4-phenylquinoline-2-carboxylic acid

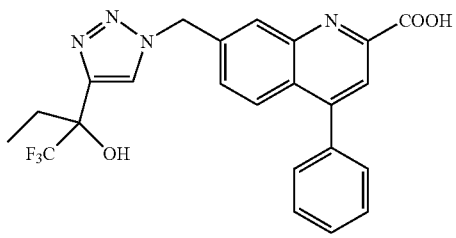

A solution of (S)-7-({4-[1-hydroxy-1-(trifluoromethyl)propyl]-1H-1,2,3-triazol-1-yl}methyl)-4-phenylquinoline-2-carbonitrile (44 mg, 0.101 mmol) in 12 M HCl (1 mL) was stirred at 110° C. overnight. The solution was concentrated, water was added and the pH was adjusted to 3 by addition of ammonium hydroxide. The aqueous phase was extracted with ethyl acetate. The combined organic layers were washed with brine, dried over $Na_2SO_4$, filtered and concentrated under reduced pressure to give the title compound. MS (+ESI): 457 (M+H)$^+$.

EXAMPLE 43

7-{[4-(1-ethyl-1-hydroxypropyl)-1H-1,2,3-triazol-1-yl]methyl}-4-phenylquinoline-2-carbonitrile

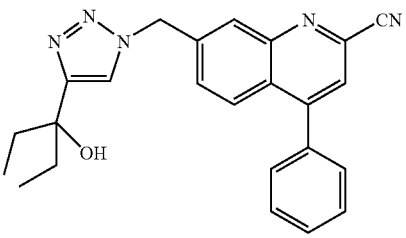

A mixture of 7-(azidomethyl)-4-phenylquinoline-2-carbonitrile (100 mg, 0.35 mmol), 3-ethylpent-1-yn-3-ol (47 mg, 0.42 mmol), copper iodide (100 mg, 0.52 mmol) and diisopropylethylamine (305 µL, 1.75 mmol) in THF (4 mL) was stirred at rt for 6 h. The reaction was quenched with saturated aqueous $NH_4Cl$ and extracted with EtOAc. The combined organic layers were washed with brine, dried over $Na_2SO_4$, filtered and concentrated under reduced pressure. Purification on silica gel (eluting with acetone/dichloromethane, 2:8) gave the title compound. MS (+ESI): 398 (M+H)$^+$.

Examples 44-49 were made using the general procedures described in Example 39, Steps 1-8 and Example 43, using the appropriate alkyne and fluoro-phenyl boronic acid.

EXAMPLE 44

7-{[4-(1-ethyl-1-hydroxypropyl)-1H-1,2,3-triazol-1-yl]methyl}-4-(4-fluorophenyl)quinoline-2-carbonitrile; MS (+ESI): 416 (M+H)+.

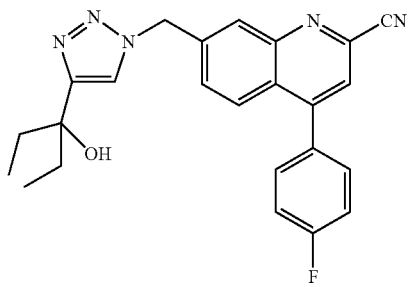

EXAMPLE 45

7-{[4-(1-ethyl-1-hydroxypropyl)-1H-1,2,3-triazol-1-yl]methyl}-4-(3-fluoro-phenyl)quinoline-2-carbonitrile;

$^1$H NMR (400 MHz, acetone-$d_6$): 8.13 (s, 1H), 8.07 (d, 1H), 7.95 (d, 2H), 7.76-7.64 (m, 2H), 7.51-7.35 (m, 3H), 5.97 (s, 2H), 3.80 (s, 1H), 1.98-1.75 (m, 4H), 0.79 (t, 6H).

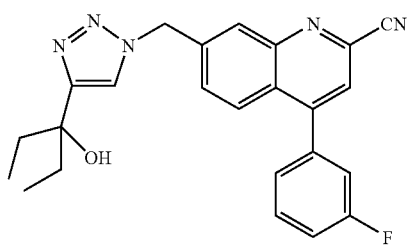

EXAMPLE 46

7-({4-[dicyclopropyl(hydroxy)methyl]-1H-1,2,3-triazol-1-yl}methyl)-4-(4-fluorophenyl)quinoline-2-carbonitrile

MS (+ESI): 439 (M+H)+.

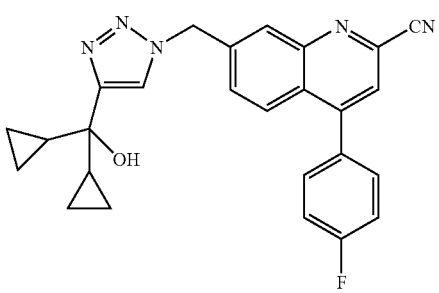

EXAMPLE 47

7-({4-[dicyclopropyl(hydroxy)methyl]-1H-1,2,3-triazol-1-yl}methyl)-4-(3-fluorophenyl)-quinoline-2-carbonitrile

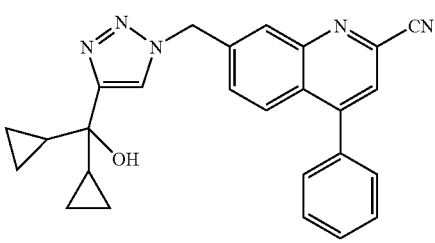

$^1$H NMR (400 MHz, acetone-$d_6$): 8.16 (s, 1H), 8.06 (d, 1H), 8.00 (s, 1H), 7.97 (s, 1H), 7.78 (d, 1H), 7.72-7.62 (m, 1H), 7.51-7.43 (m, 2H), 7.41 (t, 1H), 5.95 (s, 2H), 3.72 (s, 1H), 1.45-1.35 (m, 2H), 0.55-0.42 (m, 4H), 0.42-0.32 (m, 2H) 0.32-0.22 (m, 2H).

EXAMPLE 48

7-({4-[dicyclopropyl(hydroxy)methyl]-1H-1,2,3-triazol-1-yl}methyl)-4-phenylquinoline-2-carbonitrile;

MS (+ESI): 422 (M+H)+.

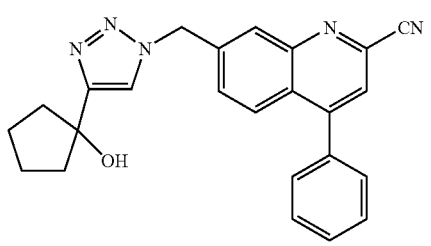

EXAMPLE 49

7-{[4-(1-hydroxycyclopentyl)-1H-1,2,3-triazol-1-yl]methyl}-4-phenylquinoline-2-carbonitrile;

MS (+ESI): 396 (M+H)+.

EXAMPLE 50

7-{[4-(1-methoxycyclopentyl)-1H-1,2,3-triazol-1-yl]methyl}-4-phenylquinoline-2-carbonitrile

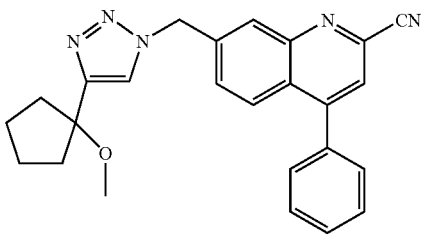

The methylether acetylene was prepared from 7-{[4-(1-hydroxycyclopentyl)-1H-1,2,3-triazol-1-yl]methyl}-4-phenylquinoline-2-carbonitrile by treatment with sodium hydride and methyl iodide.

MS (+ESI): 410 (M+H)$^+$.

EXAMPLE 51

4-Chloro-7-({4-[(1S)-1-hydroxy-1-(trifluoromethyl)propyl]-1H-1,2,3-triazol-1-yl}methyl)quinoline-2-carbonitrile

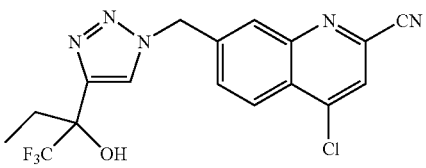

Step 1: 7-methylquinoline 1-oxide

To a solution of 7-methylquinoline (20.0 g, 140 mmol) in dichloromethane (700 mL) was added 3-chloroperoxybenzoic acid (50%, 62.6 g, 182 mmol) and stirred at room temperature for 2 h. Solid calcium hydroxide (13.4 g, 182 mmol) was added and 15 min later the mixture was filtered through celite, rinsed with dichloromethane and the liquors evaporated to dryness to give the title compound. The compound was used as such for the next step. $^1$H NMR (400 MHz, acetone-d$_6$): δ 8.45 (m, 2H), 7.93 (d, 1H), 7.80 (d, 1H), 7.55 (d, 1H), 7.35 (m, 1H), 2.60 (s, 3H).

Step 2: 7-methylquinoline-2-carbonitrile

To a solution of 7-methylquinoline-1-oxide (18.3 g, 115 mmol) in 1,2-dichloroethane (750 mL) was added trimethylsilyl cyanide (30.8 mL, 230 mmol) followed by dimethylcarbamoyl chloride (21.2 mL, 230 mmol) and stirred at room temperature overnight. The solution was quenched slowly with a sat. solution of sodium bicarbonate, diluted with water and extracted two times with dichloromethane. The combined organic extracts were dried (MgSO$_4$) and concentrated to give the crude compound. Flash chromatography of the residue on silica gel (eluting with 3% acetone in dichloromethane) provided the title compound. $^1$H NMR (400 MHz, acetone-d$_6$): δ 8.56 (d, 1H), 8.03 (d, 1H), 7.95 (s, 1H), 7.88 (d, 1H), 7.67 (d, 1H), 2.62 (s, 3H).

Step 3: 7-methylquinoline-2-carbonitrile 1-oxide

To a solution of 7-methylquinoline-2-carbonitrile (14.2 g, 84 mmol) in dichloromethane (400 mL) was added 3-chloroperoxybenzoic acid (50%, 36.4 g, 106 mmol) and stirred at room temperature overnight. Solid calcium hydroxide (7.8 g, 106 mmol) was added and 15 min later the mixture was filtered through celite, rinsed with dichloromethane and the liquors evaporated to dryness to give the crude compound. The compound was purified by flash chromatography on silica gel (eluting with 5% acetone in dichloromethane) to afford the title compound. $^1$H NMR (400 MHz, acetone-d$_6$): δ 8.40 (s, 1H), 8.05 (d, 1H), 7.97 (d, 1H), 7.75 (m, 2H), 2.65 (s, 3H).

Step 4: 4-chloro-7-methylquinoline-2-carbonitrile

A mixture of 7-methylquinoline-2-carbonitrile 1-oxide (11.5 g, 63 mmol) and phosphorus oxychloride (47 mL, 500 mmol) was heated at 100° C. for 10 min then at 200° C. for 20 min. The reaction mixture was poured into crushed ice and the precipitate was filtered. The crude material was then purified by flash chromatography on silica gel (eluting solvent: 3% acetone in dichloromethane) to provide the title compound. $^1$HNMR (400 MHz, acetone-d$_6$): δ 8.25 (d, 1H), 8.10 (s, 1H), 8.00 (d, 1H), 7.82 (dd, 1H), 2.65 (s, 3H).

Step 5: 7-(bromomethyl)-4-chloroquinoline-2-carbonitrile

To a solution of 4-chloro-7-methylquinoline-2-carbonitrile (6.66 g, 33 mmol) in CCl$_4$ (160 mL) was added NBS (6.46 g, 36.3 mmol) and benzoyl peroxide (800 mg, 3.3 mmol). The mixture was heated under reflux overnight, cooled to room temperature and evaporated to dryness. The reaction mixture was purified by flash chromatography on silica gel (eluting solvent: dichloromethane/hexane, 9/1) to provide the title compound (8.46 g). $^1$HNMR (400 MHz, acetone-d$_6$): δ 8.37 (d, 1H), 8.30 (s, 1H), 8.20 (s, 1H), 8.05 (d, 1H), 4.95 (s, 2H).

Step 6: 7-(azidomethyl)-4-chloroquinoline-2-carbonitrile

A mixture of 7-(bromomethyl)-4-chloroquinoline-2-carbonitrile (8.46 g, 30 mmol), sodium azide (2.15 g, 33 mmol) in EtOH (300 mL) was heated under reflux for 1 h. The mixture was then cooled to room temperature and evaporated to dryness. The crude material was purified by flash chromatography (eluting solvent: 100% CH$_2$Cl$_2$ to 5% acetone in CH$_2$Cl$_2$) to yield the title compound. $^1$H NMR (400 MHz, acetone-d$_6$): δ 8.40 (d, 1H), 8.20 (m, 2H), 7.97 (d, 1H), 4.85 (s, 2H).

Step 7: (S)-1-{1-[(4-chloro-2-cyanoquinolin-7-yl)methyl]-1H-1,2,3-triazol-4-yl}-1-(trifluoromethyl)propyl 4-nitrobenzoate To a solution of 7-(azidomethyl)-4-chloroquinoline-2-carbonitrile (560 mg, 2.3 mmol) and 1-ethyl-1-(trifluoromethyl)prop-2-yn-1-yl 4-nitrobenzoate (S-isomer, 728 mg, 2.42 mmol) in THF (18 mL) was added diisopropylethylamine (2.0 mL, 11.5 mmol) followed by copper iodide (655 mg, 3.45 mmol). The mixture was stirred at room temperature overnight. The reaction mixture was diluted with ethyl acetate, washed with a sat. sol. of NH$_4$Cl, Brine and dried over anhydrous MgSO$_4$. The solvent was removed under reduced pressure, and the resulting crude product was purified by flash chromatography (eluting solvent: 5% acetone in CH$_2$Cl$_2$) to afford the title compound. $^1$H NMR (400 MHz, acetone-d$_6$): δ 8.55 (s, 1H), 8.45 (d, 2H), 8.37 (d, 1H), 8.30 (d, 2H), 8.22 (s, 1H), 8.07 (s, 1H), 7.90 (d, 1H), 6.05 (s, 2H), 3.05 (m, 1H), 2.85 (m, 1H), 1.15 (t, 3H).

Step 8: (S)-4-Chloro-7-({4-[(1S)-1-hydroxy-1-(trifluoromethyl)propyl]-1H-1,2,3-triazol-1-yl}methyl)quinoline-2-carbonitrile The title compound was obtained from the ester in step 7 by hydrolysis with aq. LiOH using the general procedure described in Example 52, step 4. MS (+ESI): 396 (M+H)+.

EXAMPLE 52

(S)-7-({4-[1-hydroxy-1-(trifluoromethyl)propyl]-1H-1,2,3-triazol-1-yl}methyl)-4-(2-methyl-1,3-oxazol-4-yl)quinoline-2-carbonitrile

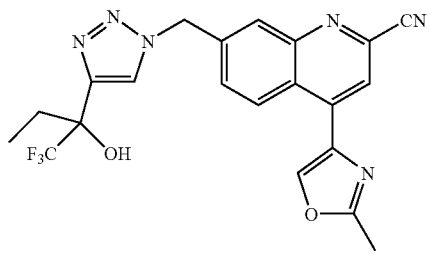

Step 1: (S)-1-(1-{[2-cyano-4-(1-ethoxyvinyl)quinolin-7-yl]methyl}-1H-1,2,3-triazol-4-yl)-1-(trifluoromethyl)propyl 4-nitrobenzoate

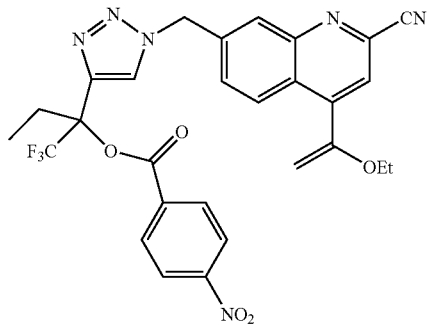

To a solution of (S)-1-{1-[(4-chloro-2-cyanoquinolin-7-yl)methyl]-1H-1,2,3-triazol-4-yl}-1-(trifluoromethyl)propyl 4-nitrobenzoate (900 mg, 1.65 mmol), tributyl (1-ethoxyvinyl)tin (0.6 ml, 1.73 mmol) in dioxane (6 mL) was added lithium chloride (210 mg, 4.96 mmol) and Pd(PPh₃)₄ (95 mg, 0.083 mmol). The reaction mixture was stirred at 100° C. overnight then cooled to room temperature. The solution was then diluted with ethyl acetate, washed with sat. sol. of ammonium chloride, brine and dried over magnesium sulfate. The crude material was purified on silica gel (eluting solvent: 3% acetone in CH₂Cl₂) to afford the title compound. ¹H NMR (400 MHz, acetone-d₆): δ 8.52 (s, 1H), 8.42 (d, 2H), 8.39 (d, 1H), 8.30 (d, 2H), 8.05 (d, 1H), 7.95 (s, 1H), 7.75 (dd, 1H), 6.02 (s, 2H), 4.75 (dd, 2H), 4.12 (q, 2H), 3.05 (m, 1H), 2.85 (m, 1H), 1.40 (t, 3H), 1.15 (t, 3H).

Step 2: (S)-1-(1-{[4-(bromoacetyl)-2-cyanoquinolin-7-yl]methyl}-1H-1,2,3-triazol-4-yl)-1-(trifluoromethyl)propyl 4-nitrobenzoate

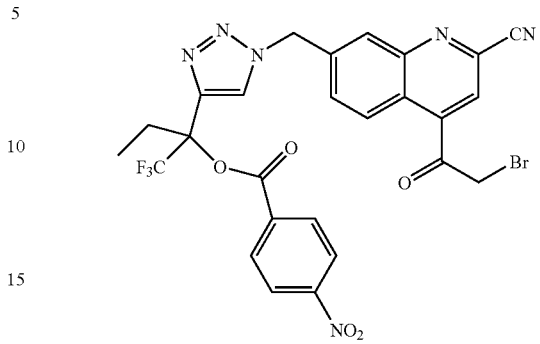

To a solution of (S)-1-(1-{[2-cyano-4-(1-ethoxyvinyl)quinolin-7-yl]methyl}-1H-1,2,3-triazol-4-yl)-1-(trifluoromethyl)propyl 4-nitrobenzoate (593 mg, 1.05 mmol) in THF (4 ml) and water (0.25 ml) was added NBS (205 mg, 1.16 mmol). The mixture was stirred at room temperature for 30 min. The solution was then evaporated to dryness and purified by flash chromatography (eluting solvent: 3% acetone in dichloromethane) to afford the title compound. ¹H NMR (400 MHz, acetone-d₆): δ 8.55 (s, 1H), 8.50 (s, 1H), 8.40 (d, 2H), 8.37 (d, 1H), 8.30 (d, 2H), 8.07 (s, 1H), 7.85 (d, 1H), 6.05 (s, 2H), 5.05 (s, 2H), 3.05 (m, 1H), 2.85 (m, 1H), 1.15 (t, 3H).

Step 3: (S)-1-(1-{[2-cyano-4-(2-methyl-1,3-oxazol-4-yl)quinolin-7-yl]methyl}-1H-1,2,3-triazol-4-yl)-1-(trifluoromethyl)propyl 4-nitrobenzoate A solution of (S)-1-(1-{[4-(bromoacetyl)-2-cyanoquinolin-7-yl]methyl}-1H-1,2,3-triazol-4-yl)-1-(trifluoromethyl)propyl 4-nitrobenzoate (0.16 g, 0.25 mmol) and acetamide (16 mg, 0.28 mmol) in DMF (0.25 mL) was stirred at room temperature for 4 h then at 100° C. overnight. The reaction mixture was diluted in ethyl acetate, washed with water, brine and dried over MgSO₄. The crude compound was purified on silica gel (eluting solvent: 2% to 5% acetone in dichloromethane) to give the desired titled product. ¹H NMR (acetone-d₆): δ 8.9 (d, 1H), 8.72 (s, 1H), 8.53 (s, 1H), 8.42 (d, 2H), 8.30 (d, 2H), 8.25 (s, 1H), 8.05 (s, 1H), 7.77 (d, 1H), 6.05 (s, 2H), 3.05 (m, 1H), 2.85 (m, 1H), 2.6 (s, 3H), 1.15 (t, 3H); and also the reduced compound 1-{1-[(4-acetyl-2-cyanoquinolin-7-yl)methyl]-1H-1,2,3-triazol-4-yl}-1-(trifluoromethyl)propyl 4-nitrobenzoate. ¹H NMR (acetone-d₆): δ 8.55 (m, 2H), 8.45 (m, 3H), 8.3 (d, 2H), 8.07 (s, 1H), 7.82 (d, 1H), 6.05 (s, 2H), 3.05 (m, 1H), 2.85 (s, 3H), 2.82 (m, 1H), 1.12 (t, 3H).

Step 4: (S)-7-({4-[1-hydroxy-1-(trifluoromethyl)propyl]-1H-1,2,3-triazol-1-yl}methyl)-4-(2-methyl-1,3-oxazol-4-yl)quinoline-2-carbonitrile To a solution of (S)-1-(1-{[2-cyano-4-(2-methyl-1,3-oxazol-4-yl)quinolin-7-yl]methyl}-1H-1,2,3-triazol-4-yl)-1-(trifluoromethyl)propyl 4-nitrobenzoate (36 mg, 0.06 mmol) in THF (1.4 mL) was added lithium hydroxide 2M (150 uL, 0.3 mmol). The mixture was stirred at room temperature for 2 h. The reaction mixture was then diluted with ethyl acetate, washed with an ammonium chloride solution, brine, dried over MgSO₄, filtered and concentrated to yield the title compound. The crude residue was purified by flash chromatography (10% acetone-90% dichloromethane) to give the desired product. ¹H NMR (400 MHz, acetone-d₆): δ 8.9 (d, 1H), 8.73 (s, 1H), 8.24 (d, 2H), 8.11 (s, 1H), 7.80 (d, 1H), 6.02 (s, 2H), 5.49 (s, 1H), 2.6 (s, 3H), 2.35 (m, 1H), 2.05 (m, 1H), 0.86 (t, 3H).

EXAMPLE 53

7-({4-[(1S)-1-hydroxy-1-(trifluoromethyl)propyl]-1H-1,2,3-triazol-1-yl}methyl)-4-(2-methyl-1,3-thiazol-4-yl)quinoline-2-carbonitrile

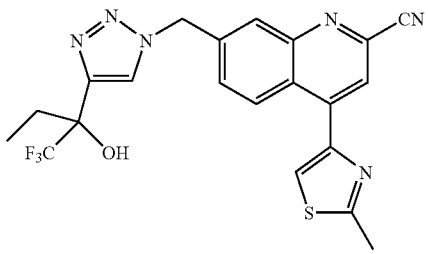

Step 1: (1S)-1-(1-{[2-cyano-4-(2-methyl-1,3-thiazol-4-yl)quinolin-7-yl]methyl}-1H-1,2,3-triazol-4-yl)-1-(trifluoromethyl)propyl 4-nitrobenzoate A solution of 1-(1-{[4-(bromoacetyl)-2-cyanoquinolin-7-yl]methyl}-1H-1,2,3-triazol-4-yl)-1-(trifluoromethyl)propyl 4-nitrobenzoate (see Example 52, Step 2) (65 mg, 0.1 mmol) and thioacetamide (9 mg, 0.11 mmol) in DMF (1 mL) was stirred at 100° C. overnight. The reaction mixture was diluted in ethyl acetate, washed with water, brine and dried over MgSO$_4$. The crude compound was purified on silica gel (eluting solvent: 3% acetone in dichloromethane) to give the desired product. $^1$H NMR (acetone-d$_6$): δ 8.85 (d, 1H), 8.52 (s, 1H), 8.42 (d, 2H), 8.30 (d, 2H), 8.17 (d, 2H), 8.05 (s, 1H), 7.75 (d, 1H), 6.05 (s, 2H), 3.05 (m, 1H), 2.85 (s, 3H), 2.85 (m, 1H), 1.15 (t, 3H).

Step 2: 7-({4-[(1S)-1-hydroxy-1-(trifluoromethyl)propyl]-1H-1,2,3-triazol-1-yl}methyl)-4-(2-methyl-1,3-thiazol-4-yl)quinoline-2-carbonitrile Following the procedure described in Example 52, Step 4, 1-(1-{[2-cyano-4-(2-methyl-1,3-thiazol-4-yl)quinolin-7-yl]methyl}-1H-1,2,3-triazol-4-yl)-1-(trifluoromethyl)propyl 4-nitrobenzoate (46 mg, 0.076 mmol) was hydrolyzed to obtain the desired compound after flash chromatography purification (10% acetone in dichloromethane). $^1$H NMR (acetone-d$_6$): δ 8.85 (d, 1H), 8.25 (s, 1H), 8.20 (d, 2H), 8.12 (s, 1H), 7.75 (d, 1H), 6.05 (s, 2H), 2.85 (s, 3H), 2.35 (m, 1H), 2.05 (m, 1H), 0.85 (t, 3H); MS (+ESI): 459 (M+H)$^+$.

EXAMPLE 54

(S)-4-Acetyl-7-({4-[1-hydroxy-1-(trifluoromethyl)propyl]-1H-1,2,3-triazol-1-yl}methyl)quinoline-2-carbonitrile

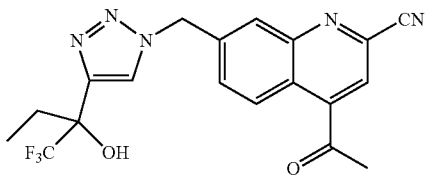

To a solution of (S)-1-{1-[(4-acetyl-2-cyanoquinolin-7-yl)methyl]-1H-1,2,3-triazol-4-yl}-1-(trifluoromethyl)propyl 4-nitrobenzoate (obtained as described in Example 52, step 4) (47 mg, 0.085 mmol) in THF (2 mL) was added lithium hydroxide 2M (210 uL, 0.42 mmol). The mixture was stirred at room temperature for 2 h. The reaction mixture was then diluted with ethyl acetate, washed with an ammonium chloride sln., brine, dried over MgSO$_4$, filtered and concentrated to yield the title compound. The crude residue was purified by flash chromatography (10% acetone-90% dichloromethane) to give the desired product. $^1$H NMR (400 MHz, acetone-d$_6$): δ 8.55 (d, 1H), 8.40 (s, 1H), 8.24 (s, 1H), 8.11 (s, 1H), 8.85 (d, 1H), 6.02 (s, 2H), 2.85 (s, 3H), 2.35 (m, 1H), 2.05 (m, 1H), 0.86 (t, 3H).

EXAMPLE 55

7-({4-[(1S)-1-hydroxy-1-(trifluoromethyl)propyl]-1H-1,2,3-triazol-1-yl}methyl)-4-(1,3-thiazol-4-yl)quinoline-2-carbonitrile

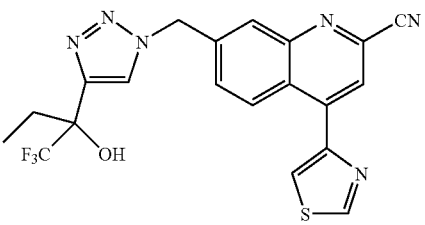

Step 1: (1S)-1-(1-{[2-cyano-4-(1,3-thiazol-4-yl)quinolin-7-yl]methyl}-1H-1,2,3-triazol-4-yl)-1-(trifluoromethyl)propyl 4-nitrobenzoate To a solution of P$_4$S$_{10}$ (34 mg, 0.08 mmol) in dioxane (1 mL) at 0° C. was added formamide (57 mg, 1.26 mmol). The reaction mixture was warmed to room temperature for 1 h. A solution of 1-(1-{[4-(bromoacetyl)-2-cyanoquinolin-7-yl]methyl}-1H-1,2,3-triazol-4-yl)-1-(trifluoromethyl)propyl 4-nitrobenzoate (see Example 52, Step 2) (160 mg, 0.25 mmol) in dioxane (1 mL) was then added and the mixture stirred at room temperature overnight. The reaction mixture was diluted in ethyl acetate, washed with water, brine and dried over MgSO$_4$. The crude compound was purified on silica gel (eluting solvent: 5% acetone in dichloromethane) to give the desired product. $^1$H NMR (acetone-d$_6$): δ 9.35 (s, 1H), 8.80 (d, 1H), 8.55 (s, 1H), 8.40 (m, 3H), 8.30 (d, 2H), 8.22 (s, 1H), 8.05 (s, 1H), 7.75 (d, 1H), 6.05 (s, 2H), 3.05 (m, 1H), 2.85 (m, 1H), 1.15 (t, 3H).

Step 2: 7-({4-[(1S)-1-hydroxy-1-(trifluoromethyl)propyl]-1H-1,2,3-triazol-1-yl}methyl)-4-(1,3-thiazol-4-yl)quinoline-2-carbonitrile Following the general procedure described in Example 52, Step 4, 1-(1-{[2-cyano-4-(1,3-thiazol-4-yl)quinolin-7-yl]methyl}-1H-1,2,3-triazol-4-yl)-1-(trifluoromethyl)propyl 4-nitrobenzoate (46 mg, 0.08 mmol) was hydrolyzed to obtain the desired compound after flash chromatography purification (10% acetone in dichloromethane). $^1$H NMR (acetone-d$_6$): δ 9.37 (s, 1H), 8.80 (d, 1H), 8.45 (s, 1H), 8.25 (d, 2H), 8.15 (s, 1H), 7.80 (d, 1H), 6.05 (s, 2H), 5.50 (s, 1H), 2.35 (m, 1H), 2.05 (m, 1H), 0.85 (t, 3H); MS (+APCI): 445 (M+H)$^+$.

EXAMPLE 56

(S)-4-(3,4-difluorophenyl)-7-({4-[1-hydroxy-1-(trifluoromethyl)propyl]-1H-1,2,3-triazol-1-yl}methyl)quinoline-2-carbonitrile

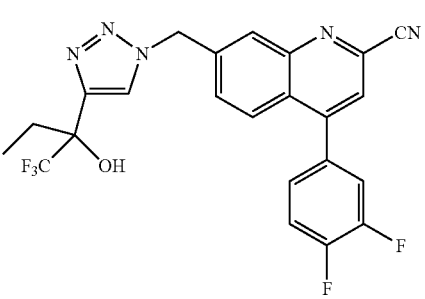

To a solution of 4-chloro-7-({4-[1-hydroxy-1-(trifluoromethyl)propyl]-1H-1,2,3-triazol-1-yl}methyl)quinoline-2-carbonitrile (100 mg, 0.25 mmol) in DME (3 mL) was added tetrakis(triphenylphosphine)palladium (14 mg, 0.013 mmol), 3,4-difluorophenylboronic acid (59 mg, 0.38 mmol) and aq. 2M $Na_2CO_3$ (0.38 mL, 0.75 mmol). After 2 h at 100° C., the reaction was quenched with water and extracted with EtOAc. The combined organic layers were washed with brine, dried over $Na_2SO_4$, filtered and concentrated under reduce pressure. Purification on silica gel (eluting with EtOAc/hexanes, 4:6) gave the title compound. MS (+ESI): 474 (M+H)+.

EXAMPLE 57

(S)-4-(3,5-dichlorophenyl)-7-({4-[1-hydroxy-1-(trifluoromethyl)propyl]-1H-1,2,3-triazol-1-yl}methyl)quinoline-2-carbonitrile

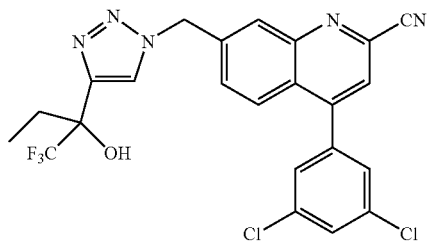

To a solution of (S)-1-{1-[(4-chloro-2-cyanoquinolin-7-yl)methyl]-1H-1,2,3-triazol-4-yl}-1-(trifluoromethyl)propyl 4-nitrobenzoate (150 mg, 0.28 mmol) in DME (3 mL) was added tetrakis(triphenylphosphine)palladium (16 mg, 0.014 mmol), 3,5-dichlorophenylboronic acid (80 mg, 0.42 mmol) and aq. 2M $Na_2CO_3$ (0.42 mL, 0.84 mmol). After 1.5 h at 100° C., the reaction was quenched with water and extracted with EtOAc. The combined organic layers were washed with brine, dried over $Na_2SO_4$, filtered and concentrated under reduce pressure. To this crude product was added THF (4 mL) and LiOH IM (1.4 mL, 1.4 mmol). After 2 h at rt, the reaction was quenched with saturated aqueous $NH_4Cl$ and extracted with EtOAc. The combined organic layers were washed with brine, dried over $Na_2SO_4$, filtered and concentrated under reduce pressure. Purification on silica gel (eluting with EtOAc/hexanes, 3:7) gave the title compound. MS (+ESI): 506 (M+H)+.

Examples 58-67 were made using the general procedures described in Example 57 using the appropriate phenyl- or heteroaryl-boronic acid.

EXAMPLE 58

(S)-4-(3,5-difluorophenyl)-7-({4-[1-hydroxy-1-(trifluoromethyl)propyl]-1H-1,2,3-triazol-1-yl}methyl)quinoline-2-carbonitrile

MS (+ESI): 474 (M+H)+.

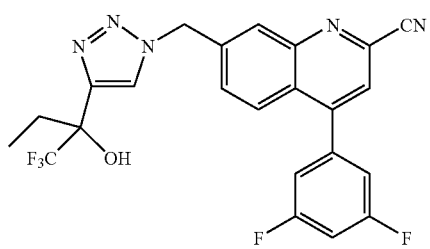

EXAMPLE 59

(S)-4-(4-chlorophenyl)-7-({4-[1-hydroxy-1-(trifluoromethyl)propyl]-1H-1,2,3-triazol-1-yl}methyl)quinoline-2-carbonitrile

MS (+ESI): 472 (M+H)+.

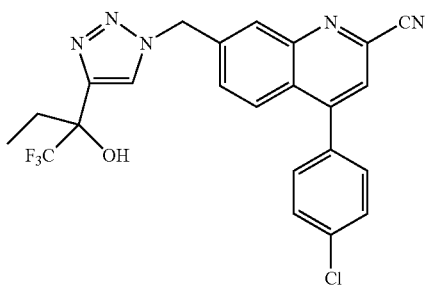

EXAMPLE 60

(S)-4-(3-chlorophenyl)-7-({4-[1-hydroxy-1-(trifluoromethyl)propyl]-1H-1,2,3-triazol-1-yl}methyl)quinoline-2-carbonitrile

MS (+ESI): 472 (M+H)+.

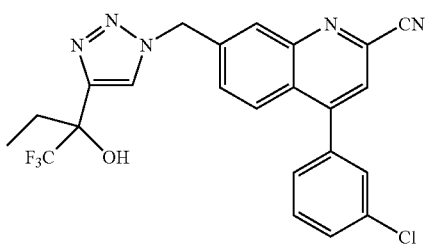

EXAMPLE 61

(S)-4-(4-fluoro-3-methylphenyl)-7-({4-[1-hydroxy-1-(trifluoromethyl)propyl]-1H-1,2,3-triazol-1-yl}methyl)quinoline-2-carbonitrile

MS (+ESI): 470 (M+H)+.

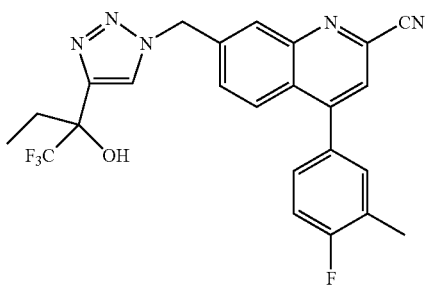

EXAMPLE 62

(S)-7-({4-[1-hydroxy-1-(trifluoromethyl)propyl]-1H-1,2,3-triazol-1-yl}methyl)-4-pyridin-3-ylquinoline-2-carbonitrile

MS (+ESI): 437 (M+H)+.

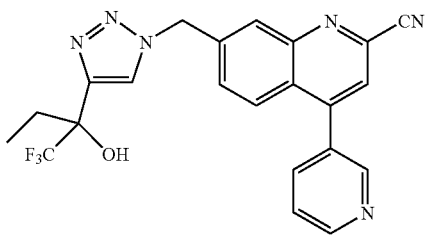

EXAMPLE 63

(S)-7-({4-[1-hydroxy-1-(trifluoromethyl)propyl]-1H-1,2,3-triazol-1-yl}methyl)-4-pyrimidin-5-ylquinoline-2-carbonitrile

MS (+ESI): 440 (M+H)+.

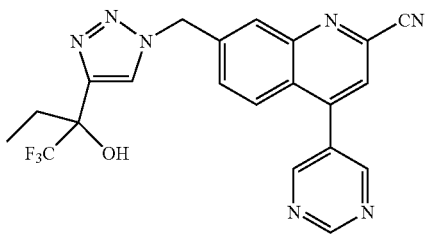

EXAMPLE 64

(S)-4-[3-(dimethylamino)phenyl]-7-({4-[1-hydroxy-1-(trifluoromethyl)propyl]-1H-1,2,3-triazol-1-yl}methyl)quinoline-2-carbonitrile;

MS (+ESI): 440 (M+H)+.

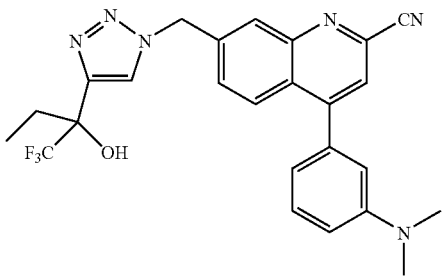

EXAMPLE 65

(S)-7-({4-[1-hydroxy-1-(trifluoromethyl)propyl]-1H-1,2,3-triazol-1-yl}methyl)-4-(4-methylphenyl)quinoline-2-carbonitrile

MS (+ESI): 452 (M+H)+.

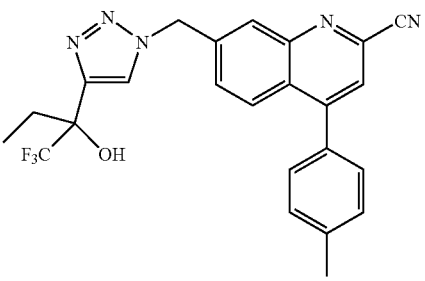

EXAMPLE 66

(S)-7-({4-[1-hydroxy-1-(trifluoromethyl)propyl]-1H-1,2,3-triazol-1-yl}methyl)-4-(3-methylphenyl)quinoline-2-carbonitrile;

MS (+ESI): 452 (M+H)+.

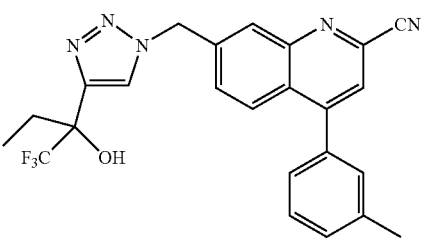

EXAMPLE 67

(S)-7-({4-[1-hydroxy-1-(trifluoromethyl)propyl]-1H-1,2,3-triazol-1-yl}methyl)-4-[3-(methylsulfonyl)phenyl]quinoline-2-carbonitrile;

MS (+ESI): 516 (M+H)+.

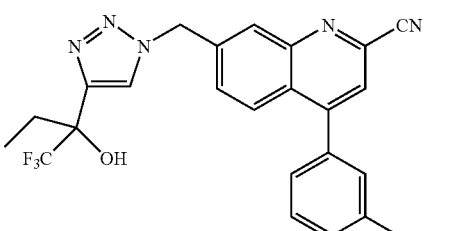

EXAMPLE 68

(S)-4-(3,5-dichlorophenyl)-7-({4-[1-hydroxy-1-(trifluoromethyl)propyl]-1H-1,2,3-triazol-1-yl}methyl)quinoline-2-carboxamide

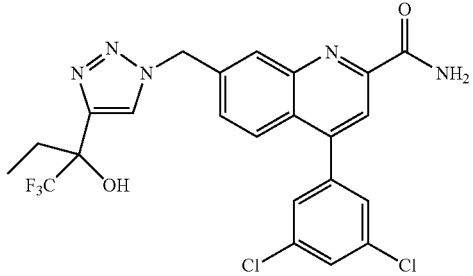

To a solution of (S)-4-(3,5-dichlorophenyl)-7-({4-[1-hydroxy-1-(trifluoromethyl)propyl]-1H-1,2,3-triazol-1-yl}methyl)quinoline-2-carbonitrile (30 mg, 0.059 mmol) in acetone (1.5 mL) and water (1 mL) was added sodium percarbonate (28 mg, 0.18 mmol). After 1.5 h at 50° C., the reaction was diluted with water and extracted with EtOAc. The combined organic layers were washed with brine, dried over $Na_2SO_4$, filtered and concentrated under reduce pressure. Purification on silica gel (eluting with acetone/dichloromethane, 2:8) gave the title compound. MS (+ESI): 524 $(M+H)^+$.

Examples 69-80 were made using the general procedure described in Example 68.

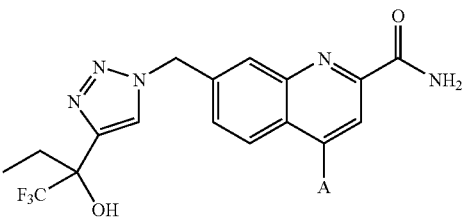

| Ex. | A | Name | MS (+ESI) (M + H)+ |
|---|---|---|---|
| 69 | Ph | (S)-7-({4-[1-hydroxy-1-(trifluoromethyl)propyl]-1H-1,2,3-triazol-1-yl}methyl)-4-phenylquinoline-2-carboxamide | 456 |
| 70 | 3-F-Ph | (S)-4-(3-fluorophenyl)-7-({4-[1-hydroxy-1-(trifluoromethyl)-propyl]-1H-1,2,3-triazol-1-yl}methyl)quinoline-2-carboxamide | * |
| 71 | 4-F-Ph | (S)-4-(4-fluorophenyl)-7-({4-[1-hydroxy-1-(trifluoromethyl)-propyl]-1H-1,2,3-triazol-1-yl}methyl)quinoline-2-carboxamide | 474 |
| 72 | 3,4-diF-Ph | (S)-4-(3,4-difluorophenyl)-7-({4-[1-hydroxy-1-(trifluoromethyl)propyl]-1H-1,2,3-triazol-1-yl}methyl)quinoline-2-carboxamide | 492 |
| 73 | 3,5-diF-Ph | (S)-4-(3,5-difluorophenyl)-7-({4-[1-hydroxy-1-(trifluoromethyl)propyl]-1H-1,2,3-triazol-1-yl}methyl)quinoline-2-carboxamide | 492 |
| 74 | 4-Cl-Ph | (S)-4-(4-chlorophenyl)-7-({4-[1-hydroxy-1-(trifluoromethyl)-propyl]-1H-1,2,3-triazol-1-yl}methyl)quinoline-2-carboxamide | 490 |
| 75 | 3-Cl-Ph | (S)-4-(3-chlorophenyl)-7-({4-[1-hydroxy-1-(trifluoromethyl)-propyl]-1H-1,2,3-triazol-1-yl}methyl)quinoline-2-carboxamide | 490 |
| 76 | 3-CH₃-4-F-Ph | (S)-4-(4-fluoro-3-methylphenyl)-7-({4-[1-hydroxy-1-(trifluoromethyl)propyl]-1H-1,2,3-triazol-1-yl}methyl)quinoline-2-carboxamide | 488 |
| 77 | 4-CH₃-Ph | (S)-7-({4-[1-hydroxy-1-(trifluoromethyl)propyl]-1H-1,2,3-triazol-1-yl}methyl)-4-(4-methylphenyl)quinoline-2-carboxamide | 470 |
| 78 | 3-CH₃-Ph | (S)-7-({4-[1-hydroxy-1-(trifluoromethyl)propyl]-1H-1,2,3-triazol-1-yl}methyl)-4-(3-methylphenyl)quinoline-2-carboxamide | 470 |
| 79 | 3-CH₃SO₂-Ph | (S)-7-({4-[1-hydroxy-1-(trifluoromethyl)propyl]-1H-1,2,3-triazol-1-yl}methyl)-4-[3-(methylsulfonyl)phenyl]quinoline-2-carboxamide | 533 |
| 80 | Cl | (S)-4-chloro-7-({4-[1-hydroxy-1-(trifluoromethyl)propyl]-1H-1,2,3-triazol-1-yl}methyl)quinoline-2-carboxamide | 414 |

*¹HNMR (400 MHz, acetone-d₆): 8.25-8.15 (m, 4H), 8.03 (d, 1H), 7.72-7.63 (m, 2H), 7.48-7.32 (m, 3H), 7.00 (s, 1H), 6.00 (s, 2H), 5.48 (s, 1H), 2.40-2.30 (m, 1H), 2.10-2.00 (m, 1H), 0.84 (t, 3H).

EXAMPLE 81

(S)-2-(1-{[2-chloro-4-(4-fluorophenyl)quinolin-7-yl]methyl}-1H-1,2,3-triazol-4-yl)-1,1,1-trifluorobutan-2-ol

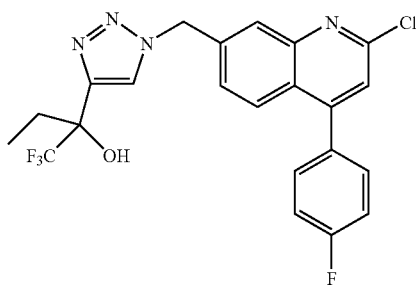

Step 1: 2-chloro-4-(4-fluorophenyl)-7-methylquinoline

A solution of 4-(4-fluorophenyl)-7-methylquinoline (3.09 g, 12.2 mmol) in phosphorus oxychloride (8 mL, 85.8 mmol) was stirred 30 min. at 90° C. The mixture was poured slowly into an aqueous saturated solution of NaHCO$_3$ and extracted with EtOAc. The combined organic layers were washed with brine, dried over Na$_2$SO$_4$, filtered and concentrated under reduce pressure. Purification on silica gel (eluting with acetone/dichloromethane/hexanes, 1:70:29) gave the title compound. MS (+ESI): 271 (M+H)$^+$.

Step 2: 7-(bromomethyl)-2-chloro-4-(4-fluorophenyl)quinoline

A solution of 2-chloro-4-(4-fluorophenyl)-7-methylquinoline (2.0 g, 7.4 mmol), N-bromo-succinimide (1.57 g, 8.8 mmol) and AIBN (30 mg, 0.18 mmol) in CCl$_4$ (40 mL) was refluxed for 16 h. The solution was then cooled to rt, filtered and concentrated. Purification on silica gel (eluting with dichloromethane/hexanes, 1:1) gave the title compound. MS (+ESI): 351 (M+H)$^+$.

Step 3: 7-(azidomethyl)-2-chloro-4-(4-fluorophenyl)quinoline

A solution of 7-(bromomethyl)-2-chloro-4-(4-fluorophenyl)quinoline (1.0 g, 2.9 mmol) and sodium azide (204 mg, 3.1 mmol) in ethanol (40 mL) was refluxed for 16 h. The solution was concentrated and dichloromethane was added. The mixture was filtered, and concentrated to give the title compound. MS (+ESI): 313 (M+H)$^+$.

Step 4: (S)-1-(1-{[2-chloro-4-(4-fluorophenyl)quinolin-7-yl]methyl}-1H-1,2,3-triazol-4-yl)-1-(trifluoromethyl)propyl 4-nitrobenzoate A mixture of 7-(azidomethyl)-2-chloro-4-(4-fluorophenyl)quinoline (500 mg, 1.60 mmol), 1-ethyl-1-(trifluoromethyl)prop-2-yn-1-yl 4-nitrobenzoate (529 mg, 1.76 mmol), copper iodide (456 mg, 2.4 mmol) and diisopropylethylamine (1.4 mL, 8.04 mmol) in THF (10 mL) was stirred at rt for 16 h. The reaction was quenched with saturated aqueous NH$_4$Cl and extracted with EtOAc. The combined organic layers were washed with brine, dried over Na$_2$SO$_4$, filtered and concentrated under reduced pressure. Purification on silica gel (eluting with EtOAc/hexanes, 4:6) gave the title compound. MS (+ESI): 614 (M+H)$^+$.

Step 5: (S)-2-(1-{[2-chloro-4-(4-fluorophenyl)quinolin-7-yl]methyl}-1H-1,2,3-triazol-4-yl)-1,1,1-trifluorobutan-2-ol A solution of 1-(1-{[2-chloro-4-(4-fluorophenyl)quinolin-7-yl]methyl}-1H-1,2,3-triazol-4-yl)-1-(trifluoromethyl)propyl 4-nitrobenzoate (300 mg, 0.49 mmol) and LiOH 2M/H$_2$O (1.25 mL, 2.5 mmol) in THF (5 mL) was stirred at rt 5 h. The reaction was quenched with saturated aqueous NH$_4$Cl and extracted with EtOAc. The combined organic layers were washed with brine, dried over Na$_2$SO$_4$, filtered and concentrated under reduce pressure. Purification on silica gel (eluting with acetone/dichloromethane, 1:9) gave the title compound. MS (+ESI): 465 (M+H)$^+$.

EXAMPLE 82

(S)-2-(1-{[2-amino-4-(4-fluorophenyl)quinolin-7-yl]methyl}-1H-1,2,3-triazol-4-yl)-1,1,1-trifluorobutan-2-ol

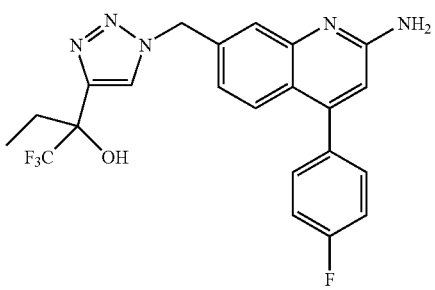

A solution of 2-(1-{[2-chloro-4-(4-fluorophenyl)quinolin-7-yl]methyl}-1H-1,2,3-triazol-4-yl)-1,1,1-trifluorobutan-2-ol (85 mg, 0.18 mmol) in NMP (1 mL) and ammonium hydroxide (15 M, 1 mL) was stirred at 175° C. in a microwave for 10 min. The reaction was quenched with saturated aqueous NaHCO$_3$ and extracted with EtOAc. The combined organic layers were washed with brine, dried over Na$_2$SO$_4$, filtered and concentrated under reduced pressure. Purification on silica gel (eluting with ethanol/dichloromethane, 1:9) gave the title compound. MS (+ESI): 445 (M+H)$^+$.

EXAMPLE 83

(S)-2-(1-{[2-(benzylamino)-4-(4-fluorophenyl)quinolin-7-yl]methyl}-1H-1,2,3-triazol-4-yl)-1,1,1-trifluorobutan-2-ol

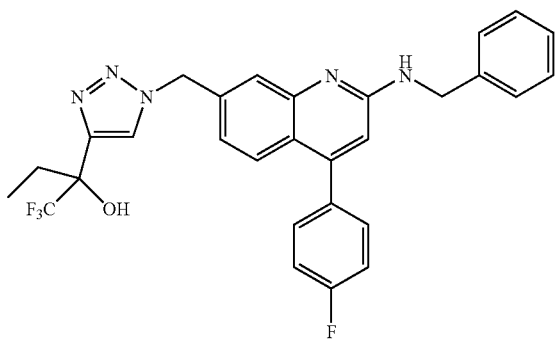

A solution of 2-(1-{[2-chloro-4-(4-fluorophenyl)quinolin-7-yl]methyl}-1H-1,2,3-triazol-4-yl)-1,1,1-trifluorobutan-2-ol (100 mg, 0.22 mmol) in benzylamine (0.3 mL) was stirred at 125° C. for 6 h. The reaction was quenched with saturated aqueous NaHCO$_3$ and extracted with EtOAc. The combined organic layers were washed with brine, dried over Na$_2$SO$_4$, filtered and concentrated under reduced pressure. Purification on silica gel (eluting with acetone/dichloromethane, 1:9) gave the title compound. MS (+ESI): 536 (M+H)$^+$.

EXAMPLE 84

(S)-1,1,1-trifluoro-2-(1-{[4-(4-fluorophenyl)-2-pyrrolidin-1-ylquinolin-7-yl]methyl}-1H-1,2,3-triazol-4-yl)butan-2-ol

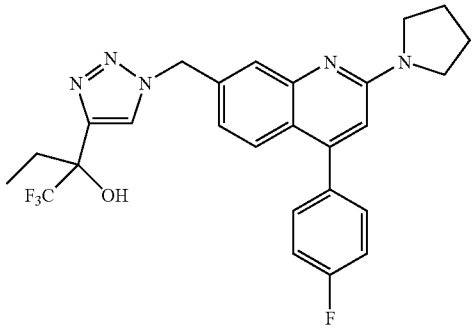

A solution of 2-(1-{[2-chloro-4-(4-fluorophenyl)quinolin-7-yl]methyl}-1H-1,2,3-triazol-4-yl)-1,1,1-trifluorobutan-2-ol (75 mg, 0.16 mmol) in NMP (0.5 mL) and pyrrolidine (0.5 mL) was stirred at 130° C. in a microwave for 20 min. The reaction was quenched with saturated aqueous $NaHCO_3$ and extracted with EtOAc. The combined organic layers were washed with brine, dried over $Na_2SO_4$, filtered and concentrated under reduce pressure. Purification on silica gel (eluting with $NH_4OH$/ethanol/dichloromethane, 1:9:90) gave the title compound. MS (+ESI): 501 (M+H)+.

EXAMPLE 85

(S)-1,1,1-trifluoro-2-(1-{[4-(4-fluorophenyl)-2-(4-methylpiperazin-1-yl)quinolin-7-yl]methyl}-1H-1,2,3-triazol-4-yl)butan-2-ol

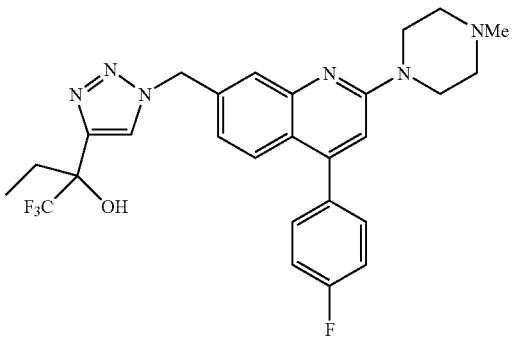

This example was prepared using the general procedure of example 84. MS (+ESI): 529 (M+H)+.

EXAMPLE 86

(S)-1,1,1-trifluoro-2-(1-{[4-(4-fluorophenyl)-2-morpholin-4-ylquinolin-7-yl]methyl}-1H-1,2,3-triazol-4-yl)butan-2-ol

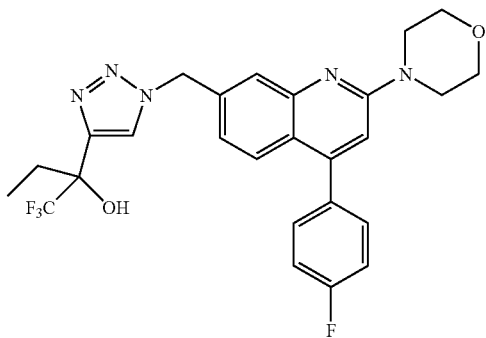

This example was prepared using the general procedure of example 84. MS (+ESI): 516 (M+H)+.

EXAMPLE 87

(S)-2-(1-{[2-(dimethylamino)-4-(4-fluorophenyl)quinolin-7-yl]methyl}-1H-1,2,3-triazol-4-yl)-1,1,1-trifluorobutan-2-ol

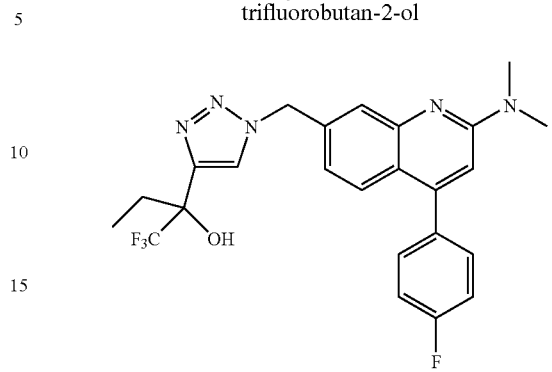

This example was prepared using the general procedure of example 84. MS (+ESI): 474 (M+H)+.

EXAMPLE 88

(S)-1,1,1-trifluoro-2-(1-{[4-(4-fluorophenyl)-2-methoxyquinolin-7-yl]methyl}-1H-1,2,3-triazol-4-yl)butan-2-ol

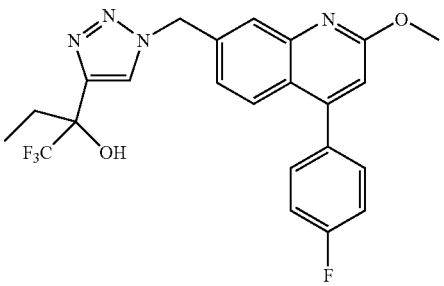

A solution of (S)-2-(1-{[2-chloro-4-(4-fluorophenyl)quinolin-7-yl]methyl}-1H-1,2,3-triazol-4-yl)-1,1,1-trifluorobutan-2-ol (250 mg, 0.54 mmol) and sodium methoxide (290 mg, 5.4 mmol) in methanol (7 mL) was refluxed for 14 h. The reaction was quenched with saturated aqueous $NH_4Cl$ and extracted with EtOAc. The combined organic layers were washed with brine, dried over $Na_2SO_4$, filtered and concentrated under reduce pressure. Purification on silica gel (eluting with acetone/dichloromethane, 1:9) gave the title compound. MS (+ESI): 461 (M+H)+.

EXAMPLE 89

(S)-1,1,1-trifluoro-2-(1-{[4-(4-fluorophenyl)-2-(2,2,2-trifluoroethoxy)quinolin-7-yl]methyl}-1H-1,2,3-triazol-4-yl)butan-2-ol

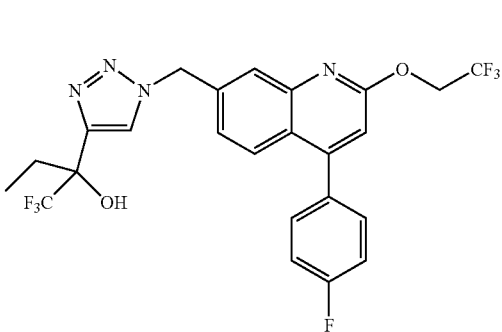

A solution of (S)-2-(1-{[2-chloro-4-(4-fluorophenyl)quinolin-7-yl]methyl}-1H-1,2,3-triazol-4-yl)-1,1,1-trifluorobutan-2-ol (60 mg, 0.13 mmol) and sodium trifluoroethoxide (79 mg, 0.65 mmol) in DMF (3 mL) was stirred at 120° C. for 1.5 h. The reaction was quenched with saturated aqueous NH₄Cl and extracted with EtOAc. The combined organic layers were washed with brine, dried over Na₂SO₄, filtered and concentrated under reduce pressure. Purification on silica gel (eluting with ethyl acetate/hexanes, 3:7) gave the title compound. MS (+ESI): 529 (M+H)⁺.

EXAMPLE 90

(S)-1,1,1-trifluoro-2-(1-{[4-(4-fluorophenyl)-2-(methylthio)quinolin-7-yl]methyl}-1H-1,2,3-triazol-4-yl)butan-2-ol

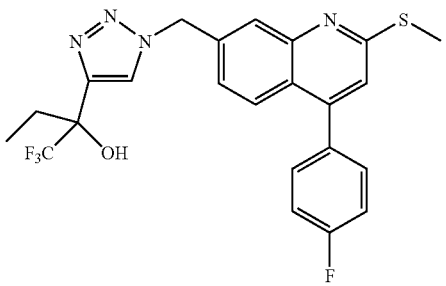

A solution of (S)-2-(1-{[2-chloro-4-(4-fluorophenyl)quinolin-7-yl]methyl}-1H-1,2,3-triazol-4-yl)-1,1,1-trifluorobutan-2-ol (85 mg, 0.18 mmol) and sodium thiomethoxide (51 mg, 0.72 mmol) in DMF (3 mL) was stirred at rt for 2 h. The reaction was quenched with saturated aqueous NH₄Cl and extracted with EtOAc. The combined organic layers were washed with brine, dried over Na₂SO₄, filtered and concentrated under reduce pressure. Purification on silica gel (eluting with ethyl acetate/hexanes, 1:9) gave the title compound. MS (+ESI): 477 (M+H)⁺.

EXAMPLE 91

(S)-1,1,1-trifluoro-2-(1-{[4-(4-fluorophenyl)-2-(methylsulfonyl)quinolin-7-yl]methyl}-1H-1,2,3-triazol-4-yl)butan-2-ol

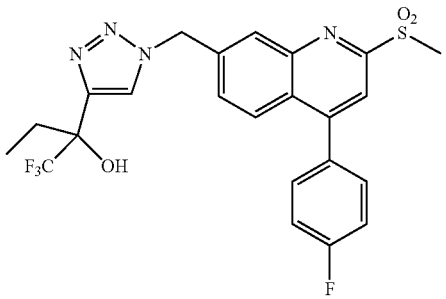

The title compound was prepared by oxidizing the sulfide of example 90 with oxone. MS (+ESI): 509 (M+H)⁺.

EXAMPLE 92

(S)-2-(1-{[2-cyclopropyl-4-(4-fluorophenyl)quinolin-7-yl]methyl}-1H-1,2,3-triazol-4-yl)-1,1,1-trifluorobutan-2-ol

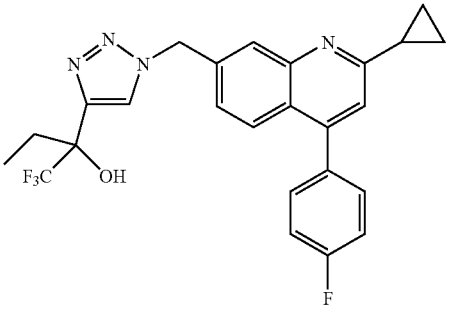

To a solution of (S)-2-(1-{[2-chloro-4-(4-fluorophenyl)quinolin-7-yl]methyl}-1H-1,2,3-triazol-4-yl)-1,1,1-trifluorobutan-2-ol (100 mg, 0.22 mmol) in THF (3 mL) was added Ni(dppp)Cl₂ (12 mg, 0.02 mmol) and cyclopropylmagnesium bromide (0.5M, 1.3 mL, 0.66 mmol). The mixture was stirred at 60° C. for 2 h. The reaction was quenched with saturated aqueous NH₄Cl and extracted with EtOAc. The combined organic layers were washed with brine, dried over Na₂SO₄, filtered and concentrated under reduce pressure. Purification on silica gel (eluting with acetone/dichloromethane, 1:9) gave the title compound MS (+ESI): 471 (M+H)⁺.

EXAMPLE 93

(S)-1,1,1-trifluoro-2-(1-{[4-(4-fluorophenyl)-2-phenylquinolin-7-yl]methyl}-1H-1,2,3-triazol-4-yl)butan-2-ol

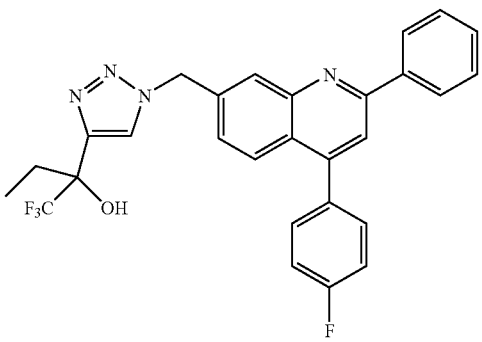

To a solution of (S)-2-(1-{[2-chloro-4-(4-fluorophenyl)quinolin-7-yl]methyl}-1H-1,2,3-triazol-4-yl)-1,1,1-trifluorobutan-2-ol (100 mg, 0.22 mmol) in DME (5 mL) was added Pd(PPh₃)₄ (12 mg, 0.01 mmol), phenylboronic acid (34 mg, 0.29 mmol) and sodium carbonate (2M, 0.2 mL, 0.44 mmol). The mixture was refluxed for 14 h. The reaction was quenched with saturated aqueous NH₄Cl and extracted with EtOAc. The combined organic layers were washed with brine, dried over Na₂SO₄, filtered and concentrated under reduced pressure. Purification on silica gel (eluting with acetone/dichloromethane, 1:9) gave the title compound. MS (+ESI): 507. (M+H)⁺.

EXAMPLE 94

(S)-1,1,1-trifluoro-2-(1-{[4-(4-fluorophenyl)-2-pyridin-3-ylquinolin-7-yl]methyl}-1H-1,2,3-triazol-4-yl)butan-2-ol

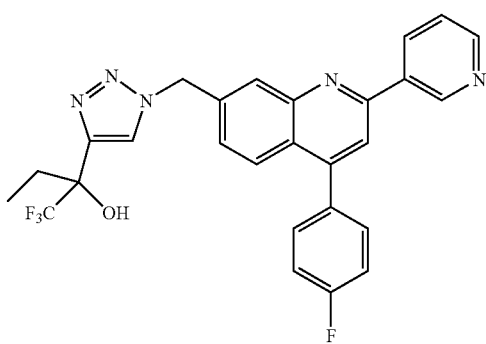

The title compound was prepared using the general procedure of example 93. MS (+ESI): 508 (M+H)$^+$.

EXAMPLE 95

(S)-1,1,1-trifluoro-2-(1-{[4-(4-fluorophenyl)-2-methylquinolin-7-yl]methyl}-1H-1,2,3-triazol-4-yl)butan-2-ol

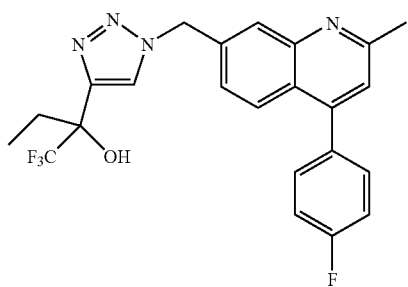

This example was prepared using the procedure of example 92. MS (+ESI): 445 (M+H)$^+$.

EXAMPLE 96

(S)-1,1,1-trifluoro-2-(1-{[4-(4-fluorophenyl)quinolin-7-yl]methyl}-1H-1,2,3-triazol-4-yl)butan-2-ol

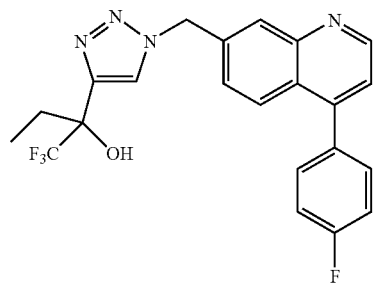

This compound was prepared using the general procedures described in example 39 using 7-methyl-4-(4-fluorophenyl)quinoline in place of 7-methyl-4-phenylquinoline, and eliminating the introduction of the 2-cyano group. MS (+ESI): 414 (M–OH)$^+$.

EXAMPLE 97

(S)-1-[4-(4-fluorophenyl)-7-({4-[1-hydroxy-1-(trifluoromethyl)propyl]-1H-1,2,3-triazol-1-yl}methyl)quinolin-2-yl]ethanone

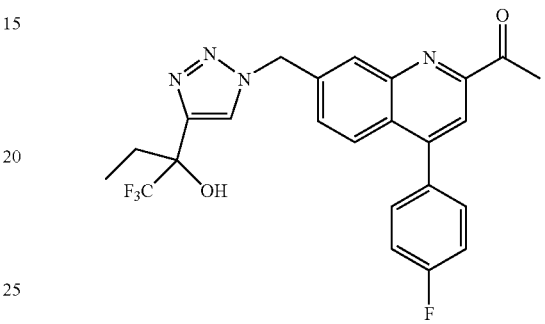

A mixture of (S)-2-(1-{[2-chloro-4-(4-fluorophenyl)quinolin-7-yl]methyl}-1H-1,2,3-triazol-4-yl)-1,1,1-trifluorobutan-2-ol (235 mg, 0.51 mmol), tributyl(1-ethoxyvinyl)tin (188 μL, 0.56 mmol), tetrakis(triphenylphosphine)palladium (30 mg, 0.025 mmol) and lithium chloride (64 mg, 1.5 mmol) was refluxed in dioxane (10 mL) overnight. An aqueous saturated solution of NaHCO$_3$ was added and the mixture extracted with EtOAc. The combined organic layers were washed with brine, dried over Na$_2$SO$_4$ and concentrated under reduce pressure. THF (5 mL) and 3M HCl (2 mL) were added, and the solution was stirred at rt for 4 h. An aqueous saturated solution of NaHCO$_3$ was added and the mixture extracted with EtOAc. The combined organic layers were washed with brine, dried over Na$_2$SO$_4$, filtered and concentrated under reduce pressure. Purification on silica gel (eluting with ethyl acetate/hexanes, 2:8) gave the title compound. MS (+ESI): 473 (M+H)$^+$.

EXAMPLE 98

(S)-1,1,1-trifluoro-2-(1-{[4-(4-fluorophenyl)-2-(1-hydroxy-1-methylethyl)quinolin-7-yl]methyl}-1H-1,2,3-triazol-4-yl)butan-2-ol

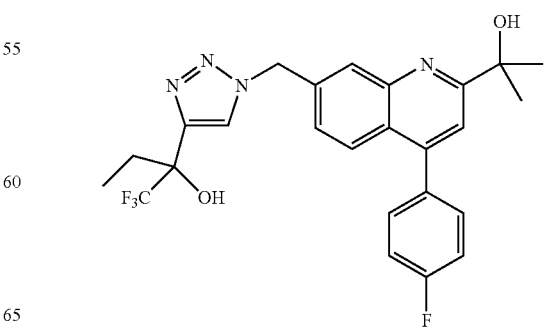

To a solution of (S)-1-[4-(4-fluorophenyl)-7-({4-[1-hydroxy-1-(trifluoromethyl)propyl]-1H-1,2,3-triazol-1-yl}methyl)quinolin-2-yl]ethanone (100 mg, 0.21 mmol) in THF (5 mL) at −78° C. was added methylmagnesium bromide 3M in ether (210 μL, 0.63 mmole). The reaction was warmed up to rt over 2 h and quenched with saturated aqueous NH4Cl and extracted with EtOAc. The combined organic layers were washed with brine, dried over Na2SO4, filtered and concentrated under reduce pressure. Purification on silica gel (eluting with acetone/dichloromethane, 2:8) gave the title compound. MS (+ESI): 490 (M+H)+.

EXAMPLE 99

(S)-1,1,1-trifluoro-2-(1-{[4-(4-fluorophenyl)-2-(1-hydroxyethyl)quinolin-7-yl]methyl}-1H-1,2,3-triazol-4-yl)butan-2-ol

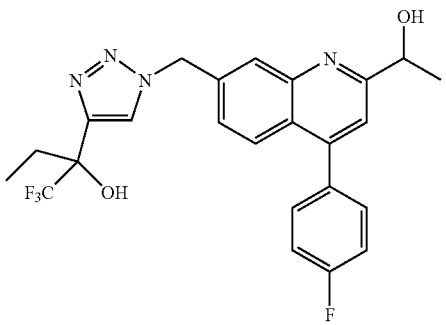

To a solution of (S)-1-[4-(4-fluorophenyl)-7-({4-[1-hydroxy-1-(trifluoromethyl)propyl]-1H-1,2,3-triazol-1-yl}methyl)quinolin-2-yl]ethanone (100 mg, 0.21 mmol) in dichloromethane (5 mL) at −78° C. was added diisobutylaluminum hydride (79 μL, 0.44 mmole). The solution was stirred 20 minutes after which a few drops of acetone were added. The reaction was warmed up to rt and sodium sulfate decahydrate (205 mg, 0.63 mmol) was added. After stirring for 30 minutes the mixture was filtered on celite and concentrated. Purification on silica gel (eluting with acetone/dichloromethane, 3:7) gave the title compound. MS (+ESI): 475 (M+H)+.

EXAMPLE 100

(S)-1,1,1-trifluoro-2-(1-{[4-(4-fluorophenyl)-2-(1-methoxyethyl)quinolin-7-yl]methyl}-1H-1,2,3-triazol-4-yl)butan-2-ol

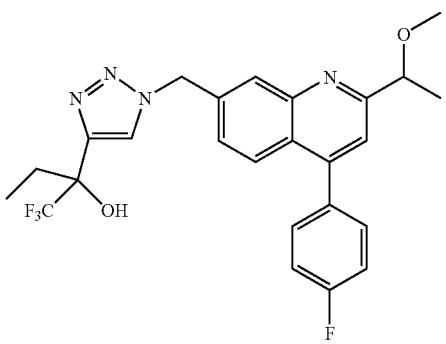

To a solution of (S)-1,1,1-trifluoro-2-(1-{[4-(4-fluorophenyl)-2-(1-hydroxyethyl)quinolin-7-yl]methyl}-1H-1,2,3-triazol-4-yl)butan-2-ol (33 mg, 0.070 mmol) in THF (1 mL) was added iodomethane (5 μL, 0.077 mmol) and sodium hydride 60% in oil (6 mg, 0.15 mmol). After 2 h at rt, the reaction was quenched with saturated aqueous NH4Cl and extracted with EtOAc. The combined organic layers were washed with brine, dried over Na2SO4, filtered and concentrated under reduce pressure. Purification on silica gel (eluting with acetone/dichloromethane, 2:8) gave the title compound. MS (+ESI): 490 (M+H)+.

EXAMPLE 101

(S)-(1Z)-1-[4-(4-fluorophenyl)-7-({4-[1-hydroxy-1-(trifluoromethyl)propyl]-1H-1,2,3-triazol-1-yl}methyl)quinolin-2-yl]ethanone oxime

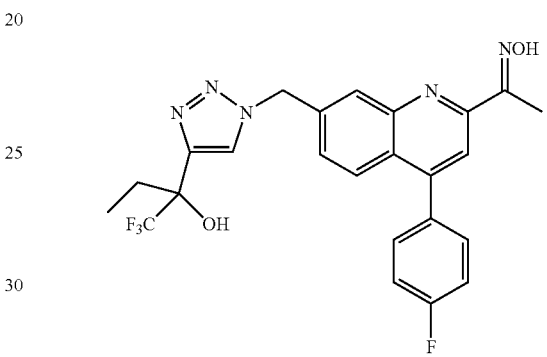

A solution of (S)-1-[4-(4-fluorophenyl)-7-({4-[1-hydroxy-1-(trifluoromethyl)propyl]-1H-1,2,3-triazol-1-yl}methyl)quinolin-2-yl]ethanone (50 mg, 0.11 mmol) and hydroxylamine hydrochloride (11 mg, 0.16 mmol) in pyridine (1 mL) was stirred at rt overnight. The solution was concentrated and purification on silica gel (eluting with acetone/dichloromethane, 2:8) gave the title compound. MS (+ESI): 488 (M+H)+.

EXAMPLE 102

(S)-(1E)-1-[4-(4-fluorophenyl)-7-({4-[1-hydroxy-1-(trifluoromethyl)propyl]-1H-1,2,3-triazol-1-yl}methyl)quinolin-2-yl]ethanone O-methyloxime

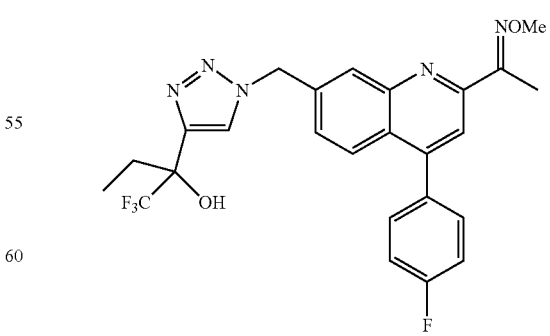

The title compound was made using the general procedure of example 101 except using NH2OMe hydrochloride in place of hydroxylamine. MS (+ESI): 502 (M+H)+.

EXAMPLE 103

7-{2-[4-(1-ethyl-1-hydroxypropyl)-1H-1,2,3-triazol-1-yl]ethyl}-4-phenylquinoline-2-carbonitrile

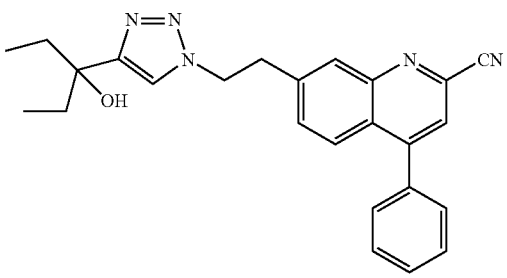

Step 1: 7-chloro-4-phenylquinoline-2-carbonitrile

A solution of 7-chloro-4-phenylquinoline (Example 39, Step 1) (3.0 g, 12.5 mmol) and m-CPBA (2.6 g, 15.0 mmol) in chloroform (50 mL) was stirred at room temperature for 3 h. The reaction was quenched with saturated aqueous $NaHCO_3$ solution and extracted twice with dichloromethane. The combined organic layers were washed with water, brine, and dried over anhydrous $MgSO_4$. The solvent was removed under reduced pressure and the resulting crude product was dissolved in chloroform (50 mL). N,N-Dimethylcarbamoyl chloride (2.4 mL, 25.0 mmol) and trimethylsilyl cyanide (3.4 mL, 25.0 mmol) were added to this solution and stirred at room temperature for 2 days. Saturated aqueous $NaHCO_3$ solution was added and the mixture stirred for 30 min. The organic layer was removed, and the aqueous layer was extracted with dichloromethane. The combined organic layers were washed with water, brine, and dried over anhydrous $MgSO_4$. The solvent was removed under reduced pressure and the resulting crude product was used in the next step without further purification.

Step 2: 7-allyl-4-phenylquinoline-2-carbonitrile

To a solution of 7-chloro-4-phenylquinoline-2-carbonitrile (3.3 g, 12.5 mmol) in dioxane (120 mL) was added tetrakistriphenylphosphine (3.6 g, 3.1 mmol) and allyltributyltin (11.5 mL, 38 mmol). The mixture was refluxed for 10 h, concentrated and purified on silica gel (eluting with dichloromethane/hexanes, 3:1) to give the title compound. MS (+ESI): 271 (M+H)$^+$.

Step 3: 7-(2-oxoethyl)-4-phenylquinoline-2-carbonitrile

Ozone was bubbled into a solution of 7-allyl-4-phenylquinoline-2-carbonitrile (1.5 g, 5.6 mmol) in ethyl acetate (100 mL) at −78° C. for 1.5 h. Nitrogen was then bubbled into the solution and methylsulfide (2.1 mL, 28 mmol) was added. The reaction was brought back to room temperature, stirred for 1 h and concentrated to give the title compound. MS (+ESI): 273 (M+H)$^+$.

Step 4: 7-(2-hydroxyethyl)-4-phenylquinoline-2-carbonitrile

To a solution of 7-(2-oxoethyl)-4-phenylquinoline-2-carbonitrile (1.5 g, 5.5 mmol) in THF (30 mL) and MeOH (10 mL) was added portionwise at 0° C. sodium borohydride (320 mg, 8.4 mmol). The mixture was stirred overnight at rt. The reaction was quenched with saturated aqueous $NH_4Cl$ and extracted with EtOAc. The combined organic layers were washed with brine, dried over $Na_2SO_4$ concentrated under reduced pressure and purified on silica gel (eluting with ethyl acetate/hexanes, 1:1) to give the title compound. MS (+ESI): 275 (M+H)$^+$.

Step 5: 7-(2-azidoethyl)-4-phenylquinoline-2-carbonitrile

To a solution of 7-(2-hydroxyethyl)-4-phenylquinoline-2-carbonitrile (180 mg, 0.66 mmol) in toluene (4 mL) was added triphenylphosphine (345 mg, 1.32 mmol), $Zn(N_3)_2$ 2 pyridine (151 mg, 0.49 mmol) and diisopropyl azodicarboxylate (260 µL, 1.32 mmol). The mixture was stirred at room temperature for 2 h, concentrated and purified on silica gel (eluting with EtOAc/hexanes, 2:8) to give the title compound. MS (+ESI): 300 (M+H)$^+$.

Step 6: 7-{2-[4-(1-ethyl-1-hydroxypropyl)-1H-1,2,3-triazol-1-yl]ethyl}-4-phenylquinoline-2-carbonitrile A mixture of 7-(2-azidoethyl)-4-phenylquinoline-2-carbonitrile (128 mg, 0.43 mmol), 3-ethylpent-1-yn-3-ol (63 mg, 0.56 mmol), copper iodide (58 mg, 0.65 mmol) and diisopropylethylamine (375 µL, 2.2 mmol) in THF (5 mL) was stirred at rt for 6 h. The reaction was quenched with saturated aqueous $NH_4Cl$ and extracted with EtOAc. The combined organic layers were washed with brine, dried over $Na_2SO_4$, filtered and concentrated under reduced pressure. Purification on silica gel (eluting with acetone/dichloromethane, 2:8) gave the title compound. MS (+ESI): 394 (M+H)$^+$.

EXAMPLE 104

(S)-7-(2-{4-[1-hydroxy-1-(trifluoromethyl)propyl]-1H-1,2,3-triazol-1-yl}ethyl)-4-phenylquinoline-2-carbonitrile

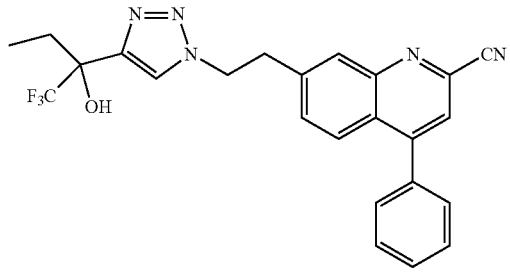

The title compound was prepared from 7-(2-azidoethyl)-4-phenylquinoline-2-carbonitrile and 3-(trifluoromethyl)-1-pent-1-yn-3-ol using the general procedure of Example 103. MS (+ESI): 452 (M+H)$^+$.

What is claimed is:

1. A compound of structural Formula I

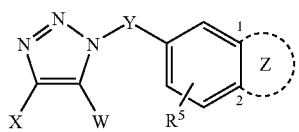

or a pharmaceutically acceptable salt thereof wherein:

is selected from the group consisting of

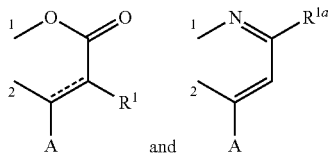

wherein the numbers "1" and "2" indicate the points of attachment within structural Formula I;

"----" is selected from a single and a double bond;

A is selected from the group consisting of:
  (a) a 5-membered heteroaryl ring containing (i) one or more carbon atoms, (ii) one heteroatom selected from oxygen and sulfur, and (iii) zero, one, two or three nitrogen atoms,
  (b) a 5-membered heteroaryl ring containing one or more carbon atoms and from one to four nitrogen atoms,
  (c) a 6-membered heteroaryl ring containing carbon atoms and one, two or three nitrogen atoms,
  (d) a bicyclic ring system selected from benzothienyl, indolyl, quinolinyl and naphthalenyl,
  (e) morpholinyl,
  (f) phenyl,
  (g) benzyl,
  (h) chloro, and
  (i) —C(O)C$_{1-3}$alkyl,
and wherein A is optionally mono-or di-substituted with a substituent independently selected at each occurrence from the group consisting of (i) fluorine, (ii) chlorine, (iii) —C$_{1-3}$ alkyl optionally substituted with one to five fluorines, (iv) —C$_{1-3}$ alkoxy optionally substituted with one to five fluorines, (v) C$_{3-6}$ cycloalkyloxy, (vi) —C$_{1-3}$alkyl-OH, (vii) —COOR$^8$, (viii) —CN, (ix) —NR$^7$R$^8$, and (x) —SO$_2$C$_{1-3}$alkyl;

W is H or methyl;

X is selected from the group consisting of pyridinyl, -Ph, and —C(R$^2$)(R$^3$)(R$^4$);

Y is selected from —CH$_2$— and —CH$_2$CH$_2$—;

R$^1$ is selected from the group consisting of —H, —C$_{1-6}$alkyl and —C$_{3-6}$cycloalkyl;

R$^{1a}$ is selected from the group consisting of: (a) —H, (b) —Cl, (c) —CN, (d) —COOR$^8$, (e) —CONR$^7$R$^8$, (f) —C(S)NR$^7$R$^8$, (g) —S(O)$_p$—C$_{1-3}$alkyl, (h) —NR$^7$R$^9$, (i) —C(=N—OH)—CH$_3$, (j) —C(=N—OCH$_3$)—CH$_3$, (k) —C(=NH)—OCH$_3$, (l) —C$_{1-6}$alkyl optionally mono-or di-substituted with a substituent independently selected at each occurrence from the group consisting of —OH and —F, (m) —C$_{1-3}$alkyl-O—C$_{1-3}$alkyl, (n) —C$_{1-3}$alkoxy optionally substituted with one to five fluorines, (o) —C$_{1-3}$alkoxy, (p) —C$_{3-6}$cycloalkyl, (q) phenyl optionally mono-or di-substituted with a substituent independently selected at each occurrence from the group consisting of —OH and —F, (r) pyridinyl optionally substituted with —C$_{1-3}$alkyl, particularly methyl, (s) 1-pyrrolidinyl, (t) 4-morpholinyl, and (u) 1-piperazinyl optionally 4N-substituted with —C$_{1-3}$alkyl particularly methyl;

p is an integer selected from zero, 1 and 2;

R$^2$ is selected from the group consisting of —H, —OH, —F, —C$_{1-3}$alkyl, —OC$_{1-3}$alkyl, —OC(O)—C$_{1-3}$alkyl, and —OC(O)-phenyl wherein phenyl is optionally substituted with a group selected from —OH and —NO$_2$; and —O-cyclic alkyl ether wherein the cyclic alkyl ether is comprised of one oxygen and 2-5 carbon atoms;

R$^3$ is selected from the group consisting of —H, —C$_{1-6}$alkyl, —C$_{1-6}$alkyl substituted with one or more of fluoro, —C$_{1-6}$alkyl substituted with R$^6$, phenyl, —C$_{2-6}$alkenyl, —C$_{3-6}$cycloalkyl, and —C$_{5-7}$cycloalkenyl;

R$^4$ is selected from the group consisting of —H, —C$_{1-6}$alkyl, —C$_{1-6}$alkyl substituted with one or more of fluoro, —C$_{1-6}$alkyl substituted with R$^6$, phenyl, —C$_{2-6}$alkenyl, —C$_{3-6}$cycloalkyl, and —C$_{5-7}$cycloalkenyl;

or R$^3$ and R$^4$ are joined together with the carbon to which they are attached to form a ring selected from —C$_{3-6}$cycloalkyl, and a 3-6 membered cyclic alkyl ether comprised of one oxygen and 2-5 carbon atoms; C$_{5-7}$ cycloalkenyl, provided that there is no double bond at the C-1 position in the ring;

or R$^2$, R$^3$ and R$^4$ are joined together with the carbon to which they are attached to form 1-cyclopentenyl or 1-cyclohexenyl;

R$^5$ is independently selected at each occurrence from the group consisting of —H, —C$_{1-6}$ alkyl and —C$_{3-6}$cycloalkyl;

R$^6$ is independently selected at each occurrence from the group consisting of —COOR$^8$, —C(O)H, —CN, —CR$^5$R$^5$OH, —OR$^5$, —S—C$_{1-6}$alkyl and —S—C$_{3-6}$cycloalkyl;

R$^7$ is selected from the group consisting of —H, —C$_{1-6}$ alkyl, —C$_{3-6}$ cycloalkyl and —COOR$^8$;

R$^8$ is selected from the group consisting of —H, —C$_{1-6}$ alkyl and —C$_{3-6}$ cycloalkyl; and R$^9$ is independently selected from the group consisting of —H, —C$_{1-6}$ alkyl, and —C$_{3-6}$ cycloalkyl, phenyl and benzyl.

2. The compound of claim 1 having structural formual Ia

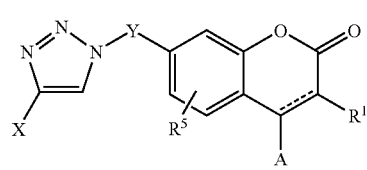

or a pharmaceutically acceptable salt thereof.

3. The compound of claim 1 having structural formual Ib

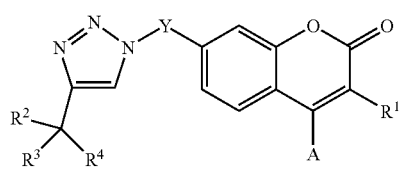

or a pharmaceutically acceptable salt thereof.

4. The compound of claim 1 having structural formual Ic

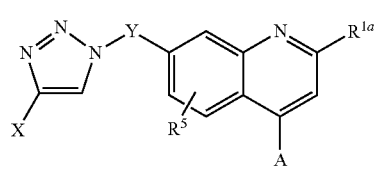

or a pharmaceutically acceptable salt thereof.

5. The compound of claim 1 having structural formual Id

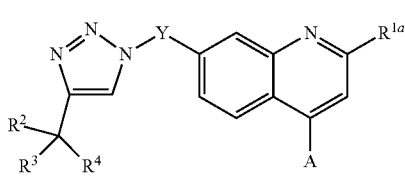

or a pharmaceutically acceptable salt thereof.

6. The compound of claim 1 wherein A is selected from (a) a 5-membered aromatic ring containing 3-4 carbon atoms and 1-2 heteroatoms selected from nitrogen, oxygen and sulfur, (b) pyridinyl, and (c) phenyl; wherein A is optionally mono-or di-substituted.

7. The compound of claim 6 wherein $R^1$ is selected from —H and —$C_{1-6}$ alkyl, and $R^{1a}$ is selected from the group consisting of —H, cyano, and —$CONR^7R^8$.

8. The compound of claim 6 wherein "- - - -" is a double bond.

9. The compound of claim 8 wherein Y is selected from —$CH_2$—.

10. The compound of claim 9 wherein X is is —$CR^2R^3R^4$.

11. The compound of claim 10 wherein $R^2$ is selected from the group consisting of —H, —OH, —F, —$C_{1-3}$alkyl, —$OCH_3$, and —$OC(O)CH_3$; $R^3$ is selected from the group consisting of —H, —$C_{1-6}$alkyl, —$C_{3-6}$cycloalkyl, phenyl and —$C_{1-6}$alkyl substituted with one or more of fluoro; and $R^4$ is selected from the group consisting of —H, —$C_{1-6}$alkyl, —$C_{3-6}$cycloalkyl, —$C_{1-6}$alkyl substituted with one or more of fluoro, and —$C_{1-6}$alkyl substituted with $R^6$.

12. The compound of claim 1 selected from the group consisting of:
- 4-(3-fluorophenyl)-7-({4-[1-hydroxy-1-(trifluoromethyl) propyl]-1H-1,2,3-triazol-1-yl}methyl)-2H-chromen-2-one;
- 4-(4-Fluorophenyl)-7-[4-(1-hydroxy-1-trifluoromethyl-propyl)-[1,2,3]triazol-1-ylmethyl]-chromen-2-one;
- 4-(2-Fluoro-phenyl)-7-[4-(1-hydroxy-1-trifluoromethyl-propyl)-[1,2,3]triazol-1-ylmethyl]-chromen-2-one;
- 4-(3,5-Difluoro-phenyl)-7-[4-(1-hydroxy-1-trifluoromethyl-propyl)-[1,2,3]triazol-1-ylmethyl]-chromen-2-one;
- 7-[4-(1-Hydroxy-1-trifluoromethyl-propyl)-[1,2,3]triazol-1-ylmethyl]-4-phenyl-chromen-2-one;
- 4-(3-Chlorophenyl)-7-[4-(1-hydroxy-1-trifluoromethyl-propyl)-[1,2,3]triazol-1-ylmethyl]-chromen-2-one;
- 4-(4-Chlorophenyl)-7-[4-(1-hydroxy-1-trifluoromethyl-propyl)-[1,2,3]triazol-1-ylmethyl]-chromen-2-one;
- 7-[4-(1-Hydroxy-1-trifluoromethyl-propyl)-[1,2,3]triazol-1-ylmethyl]-4-thiophen-3-yl-chromen-2-one;
- 4-(3-Ethoxy-phenyl)-7-[4-(1-hydroxy-1-trifluoromethyl-propyl)-[1,2,3]triazol-1-ylmethyl]-chromen-2-one;
- 7-[4-(1-Hydroxy-1-trifluoromethyl-propyl)-[1,2,3]triazol-1-ylmethyl]-4-(3-trifluoromethoxy-phenyl)-chromen-2-one;
- 7-[4-(1-Hydroxy-1-trifluoromethyl-propyl)-[1,2,3]triazol-1-ylmethyl]-4-(3-methoxy-phenyl)-chromen-2-one;
- 7-[4-(1-Ethyl-1-hydroxy-propyl)-[1,2,3]triazol-1-ylmethyl]-4-(3-fluoro-phenyl)-chromen-2-one;
- 7-[4-(1-Ethyl-1-hydroxy-propyl)-[1,2,3]triazol-1-ylmethyl]-4-(3-methoxy-phenyl)-chromen-2-one;
- 7-[4-(1-Ethyl-1-hydroxy-propyl)-[1,2,3]triazol-1-ylmethyl]-4-(4-methoxy-phenyl)-chromen-2-one;
- 7-[4-(1-Ethyl-1-hydroxy-propyl)-[1,2,3]triazol-1-ylmethyl]-4-phenyl-chromen-2-one;
- 7-[4-(1-Ethyl-1-hydroxy-propyl)-[1,2,3]triazol-1-ylmethyl]-4-(4-fluoro-phenyl)-chromen-2-one;
- 4-(4-Fluoro-phenyl)-7-[4-(tetrahydro-pyran-2-yloxymethyl)-[1,2,3]triazol-1-ylmethyl]chromen-2-one;
- 4-(4-Fluoro-phenyl)-7-[4-(1-hydroxy-1-phenyl-ethyl)-[1,2,3]triazol-1-ylmethyl]-chromen-2-one;
- 4-(4-Fluoro-phenyl)-7-[4-(4-hydroxy-tetrahydro-pyran-4-yl)-[1,2,3]triazol-1-ylmethyl]-chromen-2-one;
- 4-(4-Fluoro-phenyl)-7-[4-(4-methoxy-tetrahydro-pyran-4-yl)-[1,2,3]triazol-1-ylmethyl]-chromen-2-one;
- 4-(3-fluorophenyl)-7-[(4-phenyl-1H-1,2,3-triazol-1-yl) methyl]-2H-chromen-2-one;
- 7-[(4-benzyl-1H-1,2,3-triazol-1-yl)methyl]-4-(3-fluorophenyl)-2H-chromen-2-one;
- 4-(4-Fluorophenyl)-7-[4-(1-oxy-pyridin-2-yl)-[1,2,3]triazol-1-ylmethyl]-chromen-2-one;
- 7-[4-(Dicyclopropyl-hydroxy-methyl)-[1,2,3]triazol-1-ylmethyl]-4-(3-fluoro-phenyl)-chromen-2-one;
- 7[4-(Dicyclopropyl-hydroxy-methyl)-[1,2,3]triazol-1-ylmethyl]-4-(4-fluoro-phenyl)-chromen-2-one;
- 4-(3-fluorophenyl)-7-{[4-(1-hydroxy-1-(trifluoromethyl) propyl)-5-methyl-1H-1,2,3-triazol-1-yl]methyl]-2H-chromen-2-one;
- 4-(4-Fluorophenyl)-7-[({5-[1-hydroxy-1-(trifluoromethyl)propyl]-1,3,4-oxadiazol-2-yl}-amino)methyl]-6-methyl-2H-chromen-2-one;
- 7-{[4-(1-Cyclopropyl-2,2,2-trifluoro-1-hydroxyethyl)-1H-1,2,3-triazol-1-yl]methyl}-4-(3-fluorophenyl)-2H-chromen-2-one;
- 4-(3-Fluorophenyl)-7-({4-[1-hydroxy-1-(trifluoromethyl) butyl]-1H-1,2,3-triazol-1-yl}methyl)-2H-chromen-2-one;
- 4-(3-Methylphenyl)-7-({4-[1-ethyl-1-hydroxypropyl]-1H-1,2,3-triazol-1-yl}methyl)-2H-chromen-2-one;
- 7-[4-(1-Ethyl-1-hydroxy-propyl)-[1,2,3]triazol-1-ylmethyl]-4-pyridin-3-yl-chromen-2-one;
- 7({4[1-hydroxy-1-(trifluoromethyl)propyl]-1H-1,2,3-triazol-1-yl}methyl)-4-(5-methylisoxazol-3-yl)-2H-chromen-2-one;
- 7-({4-[1-hydroxy-1-(trifluoromethyl)propyl]-1H-1,2,3-triazol-1-yl}methyl)-4-(1,3-thiazol-2-yl)-2H-chromen-2-one;
- 7-({4-[1-hydroxy-1-(trifluoromethyl)propyl]-1H-1,2,3-triazol-1-yl}methyl)-4-(3-methoxyisoxazol-5-yl)-2H-chromen-2-one;
- 7-[4-(1-Hydroxy-1-trifluoromethyl-propyl)-[1,2,3]triazol-1-ylmethyl]-4-isothiazol-5-yl-chromen-2-one;
- 7-({4-[1-hydroxy-1-(trifluoromethyl)propyl]-1H-1,2,3-triazol-1-yl}methyl)-4-(2-methyl-1,3-oxazol-4-yl)-2H-chromen-2-one;
- 7-({4-[1-hydroxy-1-(trifluoromethyl)propyl]-1H-1,2,3-triazol-1-yl}methyl)-4-(2-methyl-1,3-thiazol-4-yl)-2H-chromen-2-one;
- 7-({4-[1-hydroxy-1-(trifluoromethyl)propyl]-1H-1,2,3-triazol-1-yl}methyl)-4-phenylquinoline-2-carbonitrile;
- 4-(3-fluorophenyl)-7-({4-[1-hydroxy-1-(trifluoromethyl) propyl]-1H-1,2,3-triazol-1-yl}methyl)quinoline-2-carbonitrile;
- 4-(4-fluorophenyl)-7-({4-[1-hydroxy-1-(trifluoromethyl) propyl]-1H-1,2,3-triazol-1-yl}methyl)quinoline-2-carbonitrile;

7-({4-[1-hydroxy-1-(trifluoromethyl)propyl]-1H-1,2,3-triazol-1-yl}methyl)-4-phenylquinoline -2-carboxylic acid;

7-{[4-(1-ethyl-1-hydroxypropyl)-1H-1,2,3-triazol-1-yl]methyl}-4-phenylquinoline-2-carbonitrile;

7-{[4-(1-ethyl-1-hydroxypropyl)-1H-1,2,3-triazol-1-yl]methyl}-4-(4-fluorophenyl)quinoline-2-carbonitrile;

7-{[4-(1-ethyl-1-hydroxypropyl)-1H-1,2,3-triazol-1-yl]methyl}-4-(3-fluoro-phenyl)quinoline -2-carbonitrile;

7-({4-[dicyclopropyl(hydroxy)methyl]-1H-1,2,3-triazol-1-yl}methyl)-4-(4-fluorophenyl)quinoline-2-carbonitrile;

7-({4-[dicyclopropyl(hydroxy)methyl]-1H-1,2,3-triazol-1-yl}methyl)-4-(3-fluorophenyl)quinoline-2-carbonitrile;

7-({4-[dicyclopropyl(hydroxy)methyl]-1H-1,2,3-triazol-1-yl}methyl)-4-phenylquinoline-2-carbonitrile;

7-{[4-(1-hydroxycyclopentyl)-1H-1,2,3-triazol-1-yl]methyl}-4-phenylquinoline-2-carbonitrile;

7-{[4-(1-methoxycyclopentyl)-1H-1,2,3-triazol-1-yl]methyl}-4-phenylquinoline-2-carbonitrile;

4-chloro-7-({4-[(1S)-1-hydroxy-1-(trifluoromethyl)propyl]-1H-1,2,3-triazol-1-yl}methyl)quinoline-2-carbonitrile 7-({4-[1-hydroxy-1-(trifluoromethyl)propyl]-1H-1,2,3-triazol-1-yl}methyl)-4-(2-methyl-1,3-oxazol-4-yl)quinoline-2-carbonitrile;

7-({4-[(1S)-1-hydroxy-1-(trifluoromethyl)propyl]-1H-1,2,3-triazol-1-yl }methyl)-4-(2-methyl-1,3-thiazol-4-yl)quinoline-2-carbonitrile;

4-acetyl-7-({4-[1-hydroxy-1-(trifluoromethyl)propyl]-1H-1,2,3-triazol-1-yl}methyl)quinoline-2-carbonitrile;

7-({4-[(1S)-1-hydroxy-1-(trifluoromethyl)propyl]-1H-1,2,3-triazol-1-yl}methyl)-4-(1,3-thiazol-4-yl)quinoline-2-carbonitrile;

4-(3,4-difluorophenyl)-7-({4-[1-hydroxy-1-(trifluoromethyl)propyl]-1H-1,2,3-triazol-1-yl}methyl)quinoline-2-carbonitrile;

4-(3,5-dichlorophenyl)-7-({4-[1-hydroxy-1-(trifluoromethyl)propyl]-1H-1,2,3-triazol-1-yl}methyl)quinoline-2-carbonitrile;

4-(3,5-difluorophenyl)-7-({4-[1-hydroxy-1-(trifluoromethyl)propyl]-1H-1,2,3-triazol-1-yl}methyl)quinoline-2-carbonitrile;

4-(4-chlorophenyl)-7-({4-[1-hydroxy-1-(trifluoromethyl)propyl]-1H-1,2,3-triazol-1-yl}methyl)quinoline-2-carbonitrile;

4-(3-chlorophenyl)-7-({4-[1-hydroxy-1-(trifluoromethyl)propyl]-1H-1,2,3-triazol-1-yl}methyl)quinoline-2-carbonitrile;

4-(4-fluoro-3-methylphenyl)-7-({4-[1-hydroxy-1-(trifluoromethyl)propyl]-1H-1,2,3-triazol-1-yl}methyl)quinoline-2-carbonitrile;

7-({4-[1-hydroxy-1-(trifluoromethyl)propyl]-1H-1,2,3-triazol-1-yl}methyl)-4-pyridin-3-ylquinoline-2-carbonitrile;

7-({4-[1-hydroxy-1-(trifluoromethyl)propyl]-1H-1,2,3-triazol-1-yl}methyl)-4-pyrimidin-5-ylquinoline-2-carbonitrile;

4-[3-(dimethylamino)phenyl]-7-({4-[1-hydroxy-1-(trifluoromethyl)propyl]-1H-1,2,3-triazol-1-yl}methyl)quinoline-2-carbonitrile;

7-({4-[1-hydroxy-1-(trifluoromethyl)propyl]-1H-1,2,3-triazol-1-yl}methyl)-4-(4-methylphenyl)quinoline-2-carbonitrile;

7-({4-[1-hydroxy-1-(trifluoromethyl)propyl]-1H-1,2,3-triazol-1-yl}methyl)-4-(3-methylphenyl)quinoline-2-carbonitrile;

7-({4-[1-hydroxy-1-(trifluoromethyl)propyl]-1H-1,2,3-triazol-1-yl}methyl)-4-[3-(methylsulfonyl)phenyl]quinoline-2-carbonitrile;

4-(3,5-dichlorophenyl)-7-({4-[1-hydroxy-1-(trifluoromethyl)propyl]-1H-1,2,3-triazol-1-yl}methyl)quinoline-2-carboxamide;

7-({4-[1-hydroxy-1-(trifluoromethyl)propyl]-1H-1,2,3-triazol-1-yl}methyl)-4-phenylquinoline-2-carboxamide;

4-(3-fluorophenyl)-7-({4-[1-hydroxy-1-(trifluoromethyl)propyl]-1H-1,2,3-triazol-1-yl}methyl)quinoline-2-carboxamide;

4-(4-fluorophenyl)-7-({4-[1-hydroxy-1-(trifluoromethyl)propyl]-1H-1,2,3-triazol-1-yl}methyl)quinoline-2-carboxamide;

4-(3,4-difluorophenyl)-7-({4-[1-hydroxy-1-(trifluoromethyl)propyl]-1H-1,2,3-triazol-1-yl}methyl)quinoline-2-carboxamide;

4-(3,5-difluorophenyl)-7-({4-[1-hydroxy-1-(trifluoromethyl)propyl]-1H-1,2,3-triazol-1-yl}methyl)quinoline-2-carboxamide;

4-(4-chlorophenyl)-7-({4-[1-hydroxy-1-(trifluoromethyl)propyl]-1H-1,2,3-triazol-1-yl}methyl)quinoline-2-carboxamide;

4-(3-chlorophenyl)-7-({4-[1-hydroxy-1-(trifluoromethyl)propyl]-1H-1,2,3-triazol-1-yl}methyl)quinoline-2-carboxamide;

4-(4-fluoro-3-methylphenyl)-7-({4-[1-hydroxy-1-(trifluoromethyl)propyl]-1H-1,2,3-triazol-1-yl}methyl)quinoline-2-carboxamide;

7-({4-[1-hydroxy-1-(trifluoromethyl)propyl]-1H-1,2,3-triazol-1-yl}methyl)-4-(4-methylphenyl)quinoline-2-carboxamide;

7-({4-[1-hydroxy-1-(trifluoromethyl)propyl]-1H-1,2,3-triazol-1-yl }methyl)-4-(3-methylphenyl)quinoline-2-carboxamide;

7-({4-[1-hydroxy-1-(trifluoromethyl)propyl]-1H-1,2,3-triazol-1-yl}methyl)-4-[3-(methylsulfonyl)phenyl]quinoline-2-carboxamide;

4-chloro-7-({4-[1-hydroxy-1-(trifluoromethyl)propyl]-1H-1,2,3-triazol-1-yl}methyl)quinoline-2-carboxamide;

2-(1-{[2-chloro-4-(4-fluorophenyl)quinolin-7-yl]methyl}-1H-1,2,3-triazol-4-yl)-1,1,1-trifluorobutan-2-ol;

2-(1-{[2-amino-4-(4-fluorophenyl)quinolin-7-yl]methyl}-1H-1,2,3-triazol-4-yl)-1,1,1-trifluorobutan-2-ol;

2-(1-{[2-(benzylamino)-4-(4-fluorophenyl)quinolin-7-yl]methyl}-1H-1,2,3-triazol-4-yl)-1,1,1-trifluorobutan-2-ol;

1,1,1-trifluoro-2-(1-{[4-(4-fluorophenyl)-2-pyrrolidin-1-ylquinolin-7-yl]methyl}-1H-1,2,3-triazol-4-yl)butan-2-ol;

1,1,1-trifluoro-2-(1-{[4-(4-fluorophenyl)-2-(4-methylpiperazin-1-yl) quinolin-7-yl]methyl}-1H-1,2,3-triazol-4-yl)butan-2-ol;

1,1,1-trifluoro-2-(1-{[4-(4-fluorophenyl)-2-morpholin-4-ylquinolin-7-yl]methyl}-1H-1,2,3-triazol-4-yl)butan-2-ol;

2-(1-{[2-(dimethylamino)-4-(4-fluorophenyl)quinolin-7-yl]methyl}-1H-1,2,3-triazol-4-yl)-1,1,1-trifluorobutan-2-ol;

1,1,1-trifluoro-2-(1-{[4-(4-fluorophenyl)-2-methoxyquinolin-7-yl]methyl}-1H-1,2,3-triazol-4-yl)butan-2-ol;

1,1,1-trifluoro-2-(1-{[4-(4-fluorophenyl)-2-(2,2,2-trifluoroethoxy)quinolin-7-yl]methyl}-1H-1,2,3-triazol-4-yl)butan-2-ol;
1,1,1-trifluoro-2-(1-{[4-(4-fluorophenyl)-2-(methylthio)quinolin-7-yl]methyl}-1H-1,2,3-triazol-4-yl)butan-2-ol;
1,1,1-trifluoro-2-(1-{[4-(4-fluorophenyl)-2-(methylsulfonyl)quinolin-7-yl]methyl}-1H-1,2,3-triazol-4-yl)butan-2-ol;
2-(1-{[2-cyclopropyl-4-(4-fluorophenyl)quinolin-7-yl]methyl}-1H-1,2,3-triazol-4-yl)-1,1,1-trifluorobutan-2-ol;
1,1,1-trifluoro-2-(1-{[4-(4-fluorophenyl)-2-phenylquinolin-7-yl]methyl}-1H-1,2,3-triazol-4-yl)butan-2-ol;
1,1,1-trifluoro-2-(1-{[4-(4-fluorophenyl)-2-pyridin-3-ylquinolin-7-yl]methyl}-1H-1,2,3-triazol-4-yl)butan-2-ol;
1,1,1-trifluoro-2-(1-{[4-(4-fluorophenyl)-2-methylquinolin-7-yl]methyl}-1H-1,2,3-triazol-4-yl)butan-2-ol;
1,1,1-trifluoro-2-(1-{[4-(4-fluorophenyl)quinolin-7-yl]methyl}-1H-1,2,3-triazol-4-yl)butan-2-ol;
1-[4-(4-fluorophenyl)-7-({4-[1-hydroxy-1-(trifluoromethyl)propyl]-1H-1,2,3-triazol-1-yl}methyl)quinolin-2-yl]ethanone;
1,1,1-trifluoro-2-(1-{[4-(4-fluorophenyl)-2-(1-hydroxy-1-methylethyl)quinolin-7-yl]methyl}-1H-1,2,3-triazol-4-yl)butan-2-ol;
1,1,1-trifluoro-2-(1-{[4-(4-fluorophenyl)-2-(1-hydroxyethyl)quinolin-7-yl]methyl}-1H-1,2,3-triazol-4-yl)butan-2-ol;
1,1,1-trifluoro-2-(1-{[4-(4-fluorophenyl)-2-(1-methoxyethyl)quinolin-7-yl]methyl}-1H-1,2,3-triazol-4-yl)butan-2-ol;
(1Z)-1-[4-(4-fluorophenyl)-7-({4-[1-hydroxy-1-(trifluoromethyl)propyl]-1H-1,2,3-triazol-1-yl}methyl)quinolin-2-yl]ethanone oxime;
(1E)-1-[4-(4-fluorophenyl)-7-({4-[1-hydroxy-1-(trifluoromethyl)propyl]-1H-1,2,3-triazol-1-yl}methyl)quinolin-2-yl]ethanone O-methyloxime;
7-{2-[4-(1-ethyl-1-hydroxypropyl)-1H-1,2,3-triazol-1-yl]ethyl}-4-phenylquinoline-2-carbonitrile; and
7-(2-{4-[1-hydroxy-1-(trifluoromethyl)propyl]-1H-1,2,3-triazol-1-yl}ethyl)-4-phenylquinoline-2-carbonitrile ;
or a pharmaceutically acceptable salt thereof.

13. The compound of claim 1 selected from the group consisting of:
4-(3-chlorophenyl)-7-[4(1-hydroxy-1-trifluoromethyl-propyl)-[1,2,3]triazol-1-ylmethyl]-chromen-2-one;
4-(4-chlorophenyl)-7-[4-(1-hydroxy-1-trifluoromethyl-propyl)-[1,2,3]triazol-1-ylmethyl]-chromen-2-one
7-[4-(1-hydroxy-1-trifluoromethyl-propyl)-[1,2,3]triazol-1-ylmethyl]-4-thiophen-3-yl-chromen-2-one;
7-[4-(dicyclopropyl-hydroxy-methyl)-[1,2,3]triazol-1-ylmethyl]-4-(3-fluoro-phenyl)-chromen-2-one;
7-{[4-(1-cyclopropyl-2,2,2-trifluoro-1-hydroxyethyl)-1H-1,2,3-triazol-1-yl]methyl}-4-(3-fluorophenyl)-2H-chromen-2-one;
7-({4-[1-hydroxy-1-(trifluoromethyl)propyl]-1H-1,2,3-triazol-1-yl}methyl)-4-(2-methyl-1,3-thiazol-4-yl)-2H-chromen-2-one;
4-(4-fluorophenyl)-7-({4-[1-hydroxy-1-(trifluoromethyl)propyl]-1H-1,2,3-triazol-1-yl}methyl)quinoline-2-carbonitrile;
7-{[4-(1-ethyl-1-hydroxypropyl)-1H-1,2,3-triazol-1-yl]methyl}-4-(4-fluorophenyl)quinoline-2-carbonitrile;
7-{[4-(1-ethyl-1-hydroxypropyl)-1H-1,2,3-triazol-1-yl]methyl}-4-(3-fluoro-phenyl)quinoline-2-carbonitrile; and
7-({4-[1-hydroxy-1-(trifluoromethyl)propyl]-1H-1,2,3-triazol-1-yl}methyl)-4-pyridin-3-ylquinoline-2-carbonitrile;
or a pharmaceutically acceptable salt thereof.

14. The compound of claim 1 selected from the group consisting of:
4-(3-fluorophenyl)-7-({4-[1-hydroxy-1-(trifluoromethyl)propyl]-1H-1,2,3-triazol-1-yl}methyl)-2H-chromen-2-one;
4-(4-fluorophenyl)-7-[4-(1-hydroxy-1-trifluoromethyl-propyl)-[1,2,3]triazol-1-ylmethyl]-chromen-2-one;
7-[4-(1-hydroxy-1-trifluoromethyl-propyl)[1,2,3]triazol-1-ylmethyl]-4-phenyl-chromen-2-one
7-({4[1-hydroxy-1-(trifluoromethyl)propyl]-1H-1,2,3-triazol-1-yl}methyl)-4-phenylquinoline-2-carbonitrile;
4-(3-fluorophenyl)-7-({4-[1-hydroxy-1-(trifluoromethyl)propyl]-1H-1,2,3-triazol-1-yl}methyl)quinoline-2-carbonitrile;
7-({4-[1-hydroxy-1-(trifluoromethyl)propyl]-1H-1,2,3-triazol-1-yl}methyl)-4-phenylquinoline-2-carboxamide; and
4-(4-fluorophenyl)-7-({4-[1-hydroxy-1-(trifluoromethyl)propyl]-1H-1,2,3-triazol-1-yl}methyl)quinoline-2-carboxamide;
or a pharmaceutically acceptable salt thereof.

15. A compound of claim 1 which is (S)-4-(3-fluorophenyl)-7-({4-[1-hydroxy-1-(trifluoromethyl)propyl]-1H-1,2,3-triazol-1-yl}methyl)-2H-chromen-2-one or a pharmaceutically acceptable salt thereof.

16. A compound of claim 1 which is (S)-4-(4-fluorophenyl)-7-({4-[1-hydroxy-1-(trifluoromethyl)propyl]-1H-1,2,3-triazol-1-yl}methyl)-2H-chromen-2-one or a pharmaceutically acceptable salt thereof.

17. A compound of claim 1 which is (S)-7-({4-[1-hydroxy-1-(trifluoromethyl)propyl]-1H-1,2,3-triazol-1-yl}methyl)-4-phenyl-2H-chromen-2-one or a pharmaceutically acceptable salt thereof.

18. A compound of claim 1 which is (S)-7-({4[1-hydroxy-1-(trifluoromethyl)propyl]-1H-1,2,3-triazol-1-yl}methyl)-4-phenylquinoline-2-carbonitrile or a pharmaceutically acceptable salt thereof.

19. A compound of claim 1 which is (S)-7-({4[1-hydroxy-1-(trifluoromethyl)propyl]-1H-1,2,3-triazol-1-yl}methyl)-4-phenylquinoline-2-carboxamide or a pharmaceutically acceptable salt thereof.

20. A pharmaceutical composition comprised of a therapeutically effective amount of a compound of claim 1 and a pharmaceutically acceptable carrier.

* * * * *